(12) United States Patent
Ahmed et al.

(10) Patent No.: US 9,795,616 B2
(45) Date of Patent: Oct. 24, 2017

(54) ORAL TRANSMUCOSAL DRUG DELIVERY SYSTEM

(71) Applicant: ABON PHARMACEUTICALS, LLC, Northvale, NJ (US)

(72) Inventors: Salah U. Ahmed, New City, NY (US); Yanming Zu, Tenafly, NJ (US); Karunakar Neelam, New Milford, NJ (US); Saad Muntazim, New York, NY (US); Tahseen A. Chowdhury, Washington-Township, NJ (US); Shiying Tian, Suffern, NY (US)

(73) Assignee: Abon Pharmaceuticals LLC, Northvale, NJ (US)

( * ) Notice: Subject to any disclaimer, the term of this patent is extended or adjusted under 35 U.S.C. 154(b) by 0 days.

(21) Appl. No.: 15/143,059

(22) Filed: Apr. 29, 2016

(65) Prior Publication Data

US 2016/0235764 A1    Aug. 18, 2016

Related U.S. Application Data

(63) Continuation of application No. 14/080,505, filed on Nov. 14, 2013, now Pat. No. 9,352,047.

(Continued)

(51) Int. Cl.
| | | |
|---|---|---|
| *A61K 31/566* | (2006.01) | |
| *A61K 31/568* | (2006.01) | |
| *A61K 47/44* | (2017.01) | |
| *A61K 31/565* | (2006.01) | |
| *A61K 47/10* | (2017.01) | |
| *A61K 47/22* | (2006.01) | |
| *A61K 47/26* | (2006.01) | |
| *A61K 9/00* | (2006.01) | |
| *A61K 9/20* | (2006.01) | |
| *A61J 3/06* | (2006.01) | |
| *A61K 45/06* | (2006.01) | |
| *B65D 75/36* | (2006.01) | |

(Continued)

(52) U.S. Cl.
CPC ............ *A61K 31/568* (2013.01); *A61J 3/06* (2013.01); *A61K 9/006* (2013.01); *A61K 9/0056* (2013.01); *A61K 9/205* (2013.01); *A61K 9/2013* (2013.01); *A61K 9/2018* (2013.01); *A61K 9/2031* (2013.01); *A61K 31/565* (2013.01); *A61K 31/566* (2013.01); *A61K 45/06* (2013.01); *A61K 47/10* (2013.01); *A61K 47/22* (2013.01); *A61K 47/26* (2013.01); *A61K 47/44* (2013.01); *B65D 75/36* (2013.01); *A61K 47/14* (2013.01); *A61K 47/36* (2013.01)

(58) Field of Classification Search
None
See application file for complete search history.

(56) References Cited

U.S. PATENT DOCUMENTS 9,352,047 B2 *    5/2016    Ahmed ................. A61K 47/44

* cited by examiner

*Primary Examiner* — Theodore R West
(74) *Attorney, Agent, or Firm* — Medler Ferro Woodhouse & Mills PLLC

(57) ABSTRACT

This invention relates to dosage forms for the delivery of drugs across the oral mucosa having improved transmucosal permeability. More specifically, the invention relates to an oral transmucosal dosage form comprising a primary vehicle comprising a crystallization inhibition agent (CIA) system and a drug, and a secondary vehicle. It also relates to methods of designing and making this dosage form, methods of administering this dosage form and methods of packaging the dosage forms.

19 Claims, 43 Drawing Sheets

Related U.S. Application Data

(60) Provisional application No. 61/726,475, filed on Nov. 14, 2012.

(51) Int. Cl.
*A61K 47/14* (2017.01)
*A61K 47/36* (2006.01)

Two-Theta

A = PEG 8000
B = Oleic Acid
C = Vit E TPGS

A = PEG 8000

B = Vit E TPGS

C = Lauroyl polyoxyl-32 glycerides

A = Polyethylene glycol 8000
B = Vitamin E-TPGS
C = Lauroyl polyoxyl-32 glycerides A = Polyethylene glycol 8000;
B = Oleic Acid;
C = Vitamin E TPGS A = Polyethylene glycol 8000
B = Lauric Acid
C = Vitamin E TPGS A = Polyethylene glycol 8000
B = Oleic Acid
C = Lauroyl polyoxyl-32 glycerides A = Polyethylene glycol 8000
B = Lauric Acid
C = Lauroyl polyoxyl-32 glycerides A = Polyethylene glycol 8000
B = Oleic Acid
C = Lecithin A = Polyethylene glycol 8000
B = Lauric Acid
C = Lecithin A = Polyethylene glycol 8000
B = Lauroyl polyoxyl-32 glycerides
C = Hydrogenated vegetable oil A = Polyethylene glycol 8000
B = Lauroyl polyoxyl-32 glycerides
C = Cocoa butter A = Polyethylene glycol 8000
B = Vitamin E TPGS
C = Cocoa butter A = Polyethylene glycol 8000
B = Lauroyl polyoxyl-32 glycerides
C = Lauroyl macrogol-6 glycerides A = Polyethylene glycol 8000
B = Sucrose esters
C = Cocoa butter A= Polyethylene glycol 8000
B = Lauroyl macrogol-6 glycerides
C =Hydrogenated vegetable oil

ORAL TRANSMUCOSAL DRUG DELIVERY SYSTEM

This invention claims the benefit of the filing date of U.S. Application No. 61/726,475, filed Nov. 14, 2012, the contents of which are hereby incorporated by reference in its entirety.

FIELD OF INVENTION

This invention relates to dosage forms for the delivery of drugs across the oral mucosa having improved transmucosal permeability. More specifically, the invention relates to an oral transmucosal dosage form comprising a primary vehicle comprising a crystallization inhibition agent (CIA) system and a drug, and a secondary vehicle. It also relates to methods of making the dosage forms, methods of administering the dosage forms, and methods of packaging the dosage forms.

BACKGROUND OF THE INVENTION

When administered orally, by swallowing a tablet or capsule, for example, some drugs undergo significant hepatic first-pass metabolism. Hepatic first-pass metabolism is sometimes undesirable. It is a phenomenon of drug metabolism whereby the concentration of a drug is greatly reduced before systemic blood circulation and delivery to the target tissue. In effect, hepatic first-pass metabolism reduces the amount of drug that reaches the target tissue. Thus oral delivery of drugs affected by hepatic first-pass metabolism is inefficient and results in poor bioavailability. In addition, first-pass metabolism may result in fluctuations in plasma drug level and high plasma levels of drug metabolites, which can be undesirable for various reasons.

Another challenge of oral administration is that some drugs may be sensitive to the acidic pH or digestive enzymes found in the stomach or other parts of the gastrointestinal tract. Thus, oral administration of these drugs for absorption in the gastrointestinal tract is not optimal.

Non-oral routes, such as intravenous or intramuscular injection, can bypass the gastrointestinal tract, and hepatic first-pass metabolism. However, these methods of administration often result in poor patient compliance due to patient aversions to injections. In addition, many injectable dosage forms must be administered by a healthcare professional, requiring additional costs and the inconvenience of scheduling and traveling to the healthcare professional.

Other non-oral routes, such as transdermal administration using an ointment or patch, or nasal routes, can result in incomplete absorption and irritation at the site of administration.

The administration of drugs orally in a dosage form that releases the drug in the mouth and allows the drug to absorbed across the oral mucosa (i.e., the oral transmucosal route), circumvents the gastrointestinal tract and hepatic first-pass metabolism. However, the design and making of oral transmucosal formulations faces challenges, particularly for drugs that are poorly soluble in water.

In typical oral transmucosal formulations, the drug particle is in crystalline or particulate form embedded in a matrix in the dosage form. The absorption of a drug from such a dosage form, particularly of drugs that are poorly soluble in water, is inefficient for several reasons.

First, the crystalline drug requires a significant amount of energy from the mouth fluid (saliva) to break the bonds between its molecules to get dissolved.

Second, compared to the gastrointestinal tract, the mouth has limited fluid (saliva) to break the crystal bonds between the drug molecules, transform the drug from particulate matter into molecular form, and/or dissolve the drug, a prerequisite for permeation and absorption.

Third, compared to the gastrointestinal tract, the mouth has limited surface area (oral mucosa) for the dissolved drug to be permeated and absorbed.

Forth, compared to the gastrointestinal tract, the oral mucosa is less permeable.

Fifth, compared to the gastrointestinal tract, the mouth has limited residence time for the drug to be dissolved from the dosage form and to be permeated and absorbed through the oral mucosa.

In addition, currently available oral transmucosal buccal adhesive dosage forms are typically small tablets, having little surface area in contact with the oral mucosa. Thus, the drug is not well exposed to the entire oral mucosal surface resulting in only a small area over which the drug may diffuse after it dissolves. This feature can limit uptake of the drug.

For these reasons, many drug molecules cannot be delivered efficiently via the oral transmucosal route using currently known means, despite the advantages of using this route.

Oral transmucosal dosage forms face the challenges of reducing the energy required to break the crystal bonds between molecules of a drug, identifying an agent to reduce and maintain the reduced crystal bonds between molecules of a drug, and using a mathematical model to calculate a composition of a system comprising a drug having a desired extent or magnitude of the reduced crystal bonds between the molecules or a desired degree of the reduced crystallinity. Oral transmucosal dosage forms also face challenges of completely reducing the energy required to break the crystal bonds between molecules of a drug, and identifying an agent to maintain the completely or substantially decrystallized form of a drug.

In addition, oral transmucosal dosage forms face challenges of overcoming the physical barrier of the oral mucosal membrane, increasing the drug permeability across the oral mucosal membrane and delivering the drug with sufficient bioavailability.

The making of oral transmucosal dose forms faces challenges of creating the reduced crystal bonds between molecules of a drug, achieving a dosage form comprising a drug having the reduced bonds between molecules, and maintaining the physic-chemical stability of the dosage form comprising a drug having the reduced bonds between molecules throughout its shelf life.

The making of oral transmucosal dose forms also faces challenges of achieving a dosage form comprising a drug having a completely or substantially decrystallized form, and maintaining the physico-chemical stability of the dosage form comprising a drug having a completely or substantially decrystallized form throughout its shelf life.

In addition, the administering of oral transmucosal dose forms faces challenges of achieving ease of administration of such a dosage form, achieving a desired dosing frequency of such a dosage form and achieving patient compliance for such a dosage form.

Some drugs for which transmucosal delivery would be highly beneficial include testosterone administered to testosterone-deficient men, and bioidentical hormones used for hormone replacement therapy in perimenopausal and menopausal women.

Transdermal and transmucosal testosterone containing dosage forms are available on the market, but are not optimal.

Some men using testosterone gel or transdermal patches experience skin irritation at the application site. (See prescribing information for ANDROGEL® testosterone gel, FORTESTA® testosterone gel, TESTIM® testosterone gel, and ANDRODERM® testosterone transdermal system).

Another concern with testosterone gel is direct skin-to-skin transfer, or clothing-to-skin transfer of this drug to another person who does not require testosterone therapy (e.g., a partner or a child) and who could suffer significant adverse events from testosterone exposure. In addition, there is the possibility of contamination of clothing or bed sheets contacted after application of the gel. (See prescribing information for ANDROGEL® testosterone gel, FORTESTA® testosterone gel, TESTIM® testosterone gel). If clothing or bed sheets are contaminated they could contaminate the clothes of women and children in the same household if these items are washed together. The product labeling for these products contain warnings about the potential for secondary exposure to testosterone. For example, labels state that "cases of secondary exposure resulting in virilization of children have been reported in post marketing surveillance of testosterone gel products." (Id.) These product labels also contain extensive instructions about proper methods of administration to decrease the chance of this occurring. (Id.)

The available testosterone gel formulations are not bioequivalent to each other. They vary in bioavailability, with differing peak serum concentrations of testosterone (total testosterone, free testosterone, and dihydrotestosterone), as well as other pharmacokinetic differences.

A buccal bioadhesive testosterone tablet is also available, and provides transmucosal delivery. However, in one trial, 16% of hypogonadal men using the buccal bioadhesive tablet reported gum-related adverse events, including edema, gingivitis, inflammation, and blistering. (See prescribing information for STRIANT® testosterone tablet). Moreover, this buccal bioadhesive tablet provides only a limited contact area for drug absorption.

Other suitable drugs for oral transmucosal delivery are hormones used in Hormone Replacement Therapy (HRT) for menopausal women. These drugs include estrogens (e.g., 17 β-estradiol, estradiol acetate, and estradiol hemihydrates) and progestins (e.g., progesterone, and norgestimate, and levonorgestrel) and combinations of these drugs. These drugs are given in various types of dosage forms, including oral tablets; vaginal rings, creams, gels or tablets; and transdermal cream, gels, or patches. There are disadvantages to each of these dosage forms. The disadvantages of oral tablets include that administration of these hormones orally may induce nausea. Disadvantages of current vaginal creams, gels, pills and rings are that they are limited to the treatment of vaginal symptoms, and are not very effective for other effects of menopause, such as bone loss, and hot flashes.

Other disadvantages of gels and creams are that they can be messy, and require attention that the correct amount is applied to ensure appropriate dosing. For creams administered to the thigh, skin must be dry and the cream must be massaged deeply into the skin. It is easier to ensure that a patient administer a complete dose if the drug is delivered in an oral solid dosage form, such as a pill or lozenge. Also dermal application of dosage form suffers from variable and unpredictable absorption due to location applied, variation in body hair, sweating, hygiene, dryness, wetness etc.

Administration of these "bioidentical hormones" by the oral transmucosal route could avoid the first pass effect, and may reduce the incidence of nausea, a common side effect of orally administered HRT, could provide systemic effects for complaints other than vaginal dryness and thinning, and could avoid the potential for incorrect dosing of creams and gels.

BRIEF SUMMARY OF THE INVENTION

The present invention can be directed to an oral transmucosal dosage form comprising (a) a primary vehicle comprising (i) a crystallization inhibition agent (CIA) system, and (ii) a drug, wherein the drug is selected from the group consisting of a practically insoluble drug, very slightly soluble drug, slightly soluble drug, or sparingly soluble drug; and (b) a secondary vehicle comprising (i) a hydrophilic water soluble component, and (ii) a texturizing agent, wherein said oral transmucosal dosage form weighs about 250 mg to about 5000 mg, said oral transmucosal dosage form erodes in about 5 to about 60 minutes, but does not disintegrate, and said oral transmucosal dosage form is solid at 37° C.

In some embodiments, the invention is directed to an oral transmucosal dosage form comprising (a) a primary vehicle comprising (i) a CIA system, and (ii) a drug, wherein the drug is selected from the group consisting of a practically insoluble drug, very slightly soluble drug, slightly soluble drug, or sparingly soluble drug; and (b) a secondary vehicle comprising (i) a hydrophilic water soluble component, and (ii) a texturizing agent, wherein said oral transmucosal dosage form comprises the drug at least a 50% reduction in crystallinity as measured by a DSC thermogram relative to a dosage form not comprising a CIA.

In some embodiments, the invention is directed to an oral transmucosal dosage form comprising (a) a primary vehicle comprising (i) a CIA system, and (ii) a drug, wherein the drug is selected from the group consisting of a practically insoluble drug, very slightly soluble drug, slightly soluble drug, or sparingly soluble drug; and (b) a secondary vehicle comprising (i) a hydrophilic water soluble component, and (ii) a texturizing agent, wherein said oral transmucosal dosage form comprises the drug having at least a 95% reduction in crystallinity as measured by a DSC thermogram relative to a dosage from not comprising the primary vehicle.

In some embodiments, the invention is directed to an oral transmucosal dosage form comprising (a) a primary vehicle comprising (i) a CIA system, and (ii) a drug, wherein the drug is selected from the group consisting of a practically insoluble drug, very slightly soluble drug, slightly soluble drug, or sparingly soluble drug; and (b) a secondary vehicle comprising (i) a hydrophilic water soluble component, and (ii) a texturizing agent, wherein the drug in said oral transmucosal dosage form has increased permeability across a polysulfone membrane relative to a drug in a dosage form not comprising the CIA.

In some embodiments, the invention is directed to an oral transmucosal dosage form comprising (a) a primary vehicle comprising (i) a CIA system, and (ii) a drug, wherein the drug is selected from the group consisting of a practically insoluble drug, very slightly soluble drug, slightly soluble drug, or sparingly soluble drug; and (b) a secondary vehicle comprising (i) a hydrophilic water soluble component, and (ii) a texturizing agent, wherein the drug in said oral transmucosal dosage form has increased permeability across a transmucosal membrane relative to a drug in a dosage form not comprising the CIA.

In some embodiments, the primary vehicle comprises at least 2 CIAs. In some embodiments, the primary vehicle comprises at least 2 CIAs, wherein the CIAs are selected from the group consisting of: (i) hydrophilic crystallization inhibition agent; (ii) a lipophilic crystallization inhibition agent; and (iii) an amphiphilic crystallization inhibition agent. In some embodiments, the primary vehicle comprises a binary crystallization inhibition agent system, wherein the binary crystallization inhibition agent system is monophasic. In some embodiments, the primary vehicle comprises a ternary crystallization inhibition agent system, wherein the ternary crystallization inhibition agent system is monophasic.

In some embodiments, the dosage form erodes at a rate of about 5 mg/min to about 500 mg/min. In some embodiments, at least 40% of the drug is released from said dosage form within 5 minutes, as measured using the glass bead rotating bottle method with 150 ml SSF. In some embodiments, at least 50% of the drug is released from said dosage form within 15 minutes, as measured using the glass bead rotating bottle method with 150 ml SSF. In some embodiments, the dosage form weighs about 1000 mg to about 3000 mg. In some embodiments, the dosage form weighs about 250 mg to about 2000 mg. In some embodiments, the dosage form erodes in about 10 to about 30 minutes.

In some embodiments, the crystallization inhibition agent is vitamin E-TPGS. In some embodiments, the crystallization inhibition agent is a PEG having a molecular weight greater than or equal to about 1450. In some embodiments, the crystallization inhibition agent is PEG-8000. In some embodiments, the crystallization inhibition agent is selected from the group consisting of hydrogenated vegetable oil, cocoa butter, carnauba wax, beeswax, and combinations thereof. In some embodiments, the crystallization inhibition agent is selected from the group consisting of a lauroyl macrogolglyceride, a stearoyl macrogolglyceride, a linoleoyl macrogol-6 glyceride, an oleoyl polyoxyl-6 glyceride, a lauroyl macrogol-6 glyceride, vitamin E-TPGS, a sucrose ester, lecithin, oleic acid, xylitol, mannitol, sorbitol, galactilol, vloemitol, isomalt, erythriol, and combinations thereof. In some embodiments, the oral transmucosal dosage form comprises a crystallization inhibition agent selected from the group consisting of xylitol, mannitol, sorbitol, galactilol, vloemitol, isomalt, erythriol, and combinations thereof. In some embodiments, the crystallization inhibition agent is selected from a group consisting of a polyvinylpyrrolidone polymer having a molecular weight greater than or equal to 1000, a vinylpyrrolidone-vinyl acetate co-polymer or a polyvinyl caprolactum-polyvinyl acetate-polyethylene glycol graft co-polymer.

In some embodiments, the secondary vehicle comprises isomalt, mannitol, sucrose and sorbitol. In some embodiments, texturizing agent is one or more of xanthan gum, lecithin, xylitol and sodium alginate. In some embodiments, the drug is testosterone.

In some embodiments, the oral transmucosal dosage form comprises a texturizing agent selected from the group consisting of xanthan gum, lecithin, hydroxypropyl cellulose (HPC), hydroxyethyl cellulose (HEC), hydroxypropylmethylcellulose (HPMC), polycarbophil, carbomer and sodium alginate.

In some embodiments, the drug comprises 0.1-20% of the weight of said primary vehicle.

In some embodiments, the drug is a practically insoluble drug or a very slightly soluble drug.

In some embodiments, the drug is in free base form. In some embodiments, the drug is selected from the group consisting of a drug subject to high first pass effect, a drug sensitive to low pH, and a drug unstable in the presence of digestive enzymes. In some embodiments, the drug is selected from the group consisting of a bioidentical or synthetic hormone, a nonsteroidal anti-inflammatory drug, an antispasmodic agent, an anti-hypertensive, an anxiolytic or hypnotic agent, a corticosteroid, an antipsychotic, a calcium channel blocker, an alpha-agonist, a central nervous system stimulant, an antiemetic, a monoamine oxidase inhibitor, an antidementia agent, a dopamine agonist, a prostaglandin, an opiate, a narcotic, or a muscarinic antagonist tropane alkaloid, and combinations thereof.

In some embodiments, the invention is directed to a transmucosal dosage form comprising (a) a primary vehicle comprising (i) a hydrophilic crystallization inhibition agent, (ii) a lipophilic crystallization inhibition agent, (iii) an amphiphilic crystallization inhibition agent, and (iv) testosterone; and (b) a secondary vehicle comprising (i) a hydrophilic water soluble component, and (ii) a texturizing agent, wherein said oral transmucosal dosage form weighs about 250 mg to about 5000 mg, said transmucosal dosage form erodes in about 5 to about 60 minutes, but does not disintegrate, and said oral transmucosal dosage form is solid at 37° C.

In some embodiments, the primary vehicle is monophasic. In some embodiments, the dosage form erodes at a rate of about 5 mg/min to about 500 mg/min. In some embodiments, at least 40% of the drug is released from said dosage form within 5 minutes, as measured using the glass bead rotating bottle method with 150 ml SSF. In some embodiments, at least 50% of the drug is released from said dosage form within 15 minutes, as measured using the glass bead rotating bottle method with 150 ml SSF.

In some embodiments, the dosage form weighs about 1000 mg to about 3000 mg. In some embodiments, the dosage form erodes in about 10 to about 30 minutes.

In some embodiments, the invention is directed to a transmucosal dosage form comprising a drug, polyethylene glycol having a molecular weight of about 1450 or above, and a secondary vehicle wherein said oral transmucosal dosage form weighs about 250 mg to about 5000 mg, said oral transmucosal dosage form erodes in about 10 to about 30 minutes, but does not disintegrate, and said oral transmucosal dosage form is solid at 37° C.

In some embodiments, the invention is directed to an oral transmucosal dosage form comprising: (a) a primary vehicle comprising a crystallization inhibition agent and testosterone; and (b) a secondary vehicle comprising (i) a hydrophilic water soluble component, and (ii) a texturizing agent, wherein said oral transmucosal dosage form weighs about 250 mg to about 5000 mg, said oral transmucosal dosage form erodes in about 5 to about 60 minutes, but does not disintegrate, and said oral transmucosal dosage form is solid at 37° C.

In some embodiments, the invention is directed to a method of providing a drug to someone in need thereof, comprising administering any of the dosage forms described herein.

In some embodiments, the invention is directed to a method of making an oral transmucosal dosage form comprising (i) providing a crystallization inhibition agent selected from the group consisting of a hydrophilic crystallization inhibition agent, an amphiphilic crystallization inhibition agent, or a lipophilic crystallization inhibition agent; (ii) applying heat to melt said crystallization inhibition agent, and mixing to create a molten mixture; (iii) adding a drug to said molten mixture, and mixing said drug and said molten mixture; (iv) cooling said molten mixture and milling said molten mixture to form a powder primary vehicle; (v) adding a secondary vehicle to said powder primary vehicle and mixing; and (vi) compressing said secondary vehicle and powder primary vehicle into an oral transmucosal dosage form, wherein said transmucosal dosage form is about 250 mg to about 5000 mg, erodes in about 5 to about 60 minutes, but does not disintegrate, and is solid at 37° C.

In some embodiments, the invention is directed to a method of making an oral transmucosal dosage form comprising: (i) melting a single or a mixture of one or more crystallization inhibition agents selected from the group consisting of hydrophilic crystallization inhibition agents, lipophilic crystallization inhibition agents, amphiphilic crystallization inhibition agents, or combinations thereof; (ii) adding appropriate stabilizing agent(s) if necessary; (iii) adding drug or active pharmaceutical ingredient to molten crystallization inhibition agent(s), and mixing; (iv) mixing appropriate components of the secondary vehicle with the molten mixture in either elevated or room temperature; (v) cooling the resultant mixture if necessary; (vi) milling the resultant mixture through a mill to form a powder, which serves as the primary vehicle; (vii) mixing the remaining portion of the secondary vehicle with the primary vehicle; (viii) compressing said secondary vehicle and powder primary vehicle into an oral transmucosal dosage form; wherein said transmucosal dosage form is about 250 mg to about 5000 mg, erodes in about 5 to 60 minutes, but does not disintegrate and is solid at 37° C.

In some embodiments, the invention is directed to a method of making an oral transmucosal dosage form comprising the steps of: (i) mixing drug or active pharmaceutical ingredient with one or more hydrophilic crystallization inhibition agent(s); (ii) solubilizing this mixture in an appropriate solvent or a mixture of solvents; (iii) mixing the solution with the hydrophilic water soluble component(s) of the secondary vehicle; (iv) evaporating the solvent(s) using oven, obtaining a dispersion of the drug in hydrophilic crystallization inhibition agent(s) mixed uniformly with hydrophilic water soluble portion of the secondary vehicle, which will act as the primary vehicle; (v) milling the primary vehicle using a mill to form a powder; (vi) mixing the powder from the previous step with the remaining portion of the secondary vehicle; and (vii) compressing said secondary vehicle and powder primary vehicle into an oral transmucosal dosage form; wherein said transmucosal dosage form is about 250 mg to about 5000 mg, erodes in about 5 to 60 minutes, but does not disintegrate and is solid at 37° C.

In some embodiments, the invention is directed to an oral transmucosal dosage form comprising: (a) a primary vehicle comprising (i) a crystallization inhibition agent, and (ii) a drug, wherein the drug is selected from the group consisting of a practically insoluble drug, very slightly soluble drug, slightly soluble drug, or sparingly soluble drug; and (b) a secondary vehicle comprising (i) a hydrophilic water soluble component, and (ii) a texturizing agent, wherein said oral transmucosal dosage form weighs about 250 mg to about 5000 mg and is solid at 37° C., and wherein said crystallization inhibition agent facilitates decrystallization of said drug, and during dissolution of said oral transmucosal dosage form said crystallization inhibition agent prevents recrystallization of said drug.

In some embodiments, the transmucosal dosage form as described herein can be packaged in moisture and/or oxygen barrier polymer film as blister package, e.g., to improve its stability as well as patient compliance and ease of administration.

DETAILED DESCRIPTION OF THE INVENTION

Figure 1:
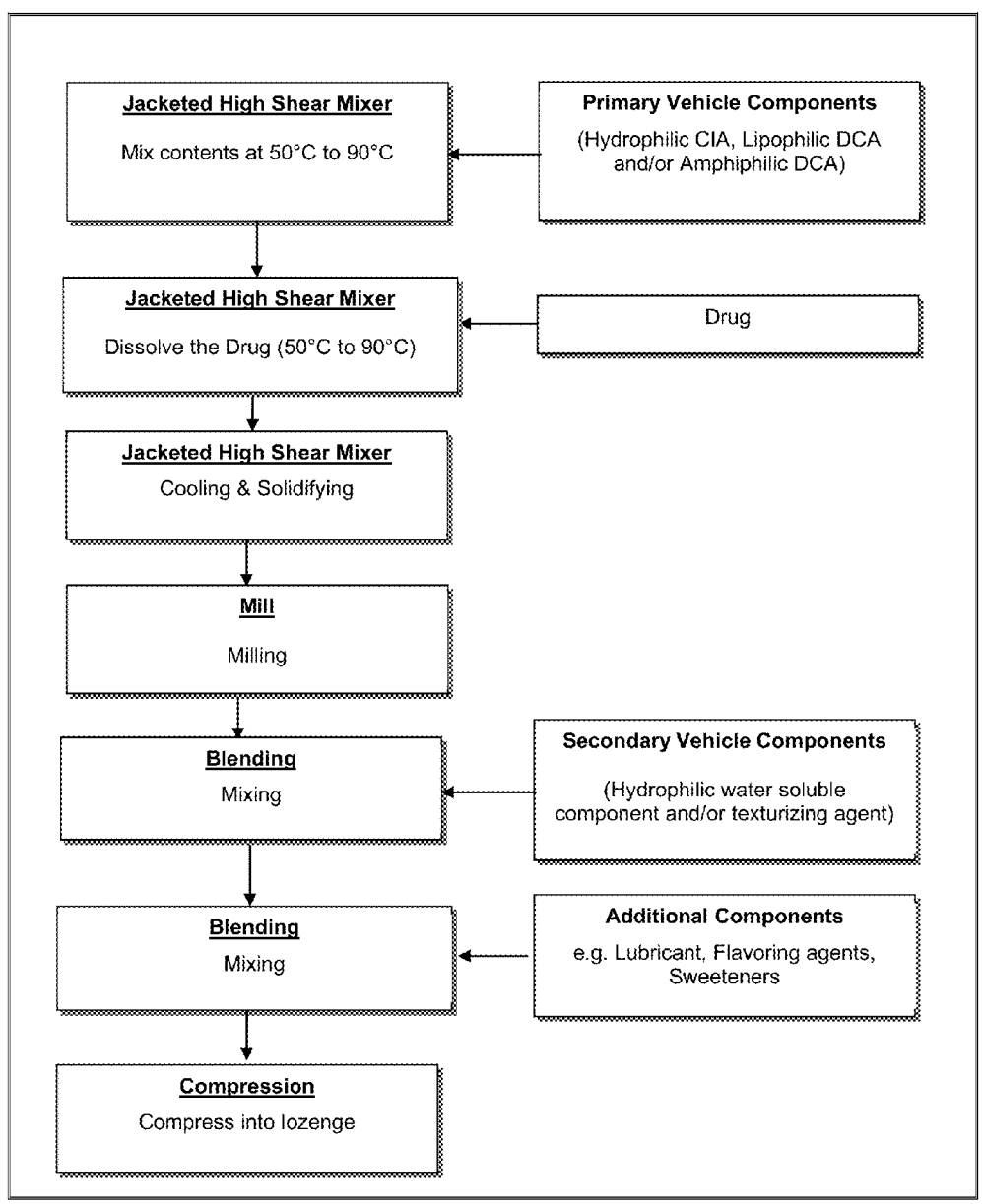
FIG. 1 depicts a manufacturing process flow chart for a process of manufacturing some embodiments of the invention using melt dispersion.

The present invention offers a unique solution to the challenges of administering certain drugs by providing a novel oral transmucosal dosage form. This drug delivery system is designed to deliver poorly soluble crystalline drugs with a desired extent or magnitude of the reduced bonds between the molecules or the reduced crystallinity, thereby capable of achieving a tailored and improved in-vivo permeation and absorption.

When the oral transmucosal dosage form of the invention is administered, the entire surface of the oral cavity is utilized to achieve rapid and superior drug absorption compared to buccal patches. The dosage form of the present invention allows increased solubility, dissolution and permeation or absorption of a drug in the oral cavity via the oral mucosa, and decreased passage of the drug in the gastrointestinal tract whereby absorbed drugs enters into the hepatic portal system, contributing to significant first pass metabolism and liver toxicity.

Absorption via the oral mucosa increases the bioavailability of transmucosally administered drugs that are subject to first-pass metabolism. In addition, the drug is protected from degradation due to pH or to digestive enzymes of the gastrointestinal tract.

The oral transmucosal dosage form of the invention also causes less irritation of gum tissue as compared to buccal bioadhesive tablets, and due to slow erosion and longer duration can provide more reliable and reproducible absorption compared to sublingual dosage forms. In addition, the dosage form of the current invention is designed not to adhere to a specific location in the buccal area, rather gradually erode to deliver drug throughout the buccal mucosa for a period of up to 5 to 30 minutes providing more efficient drug absorption compared to buccal patch. The lozenge, troche or lollipop dosage form is easy to take and more convenient than transdermal or injectable dosage forms.

Moreover, this oral transmucosal dosage form of the invention offers administration benefits, such as ease of administration, desired dosing frequency and improved patient compliance. This novel technology also offers clinical benefits, such as diminished blood drug peak or trough ratio and reduced drug pharmacokinetic variability.

Most Active Pharmaceutical Ingredients (API) or drugs are crystalline solids. A crystal is a unique arrangement of atoms or molecules in a repeating orderly pattern extending in three spatial dimensions, held together through force stabilizing the structure as a group of molecules. A crystal structure is composed of a pattern, a set of atoms arranged in an orderly way, and a lattice exhibiting long-range order and symmetry. Patterns are located upon the points of a lattice, which is an array of points repeating periodically in three dimensions. The points can be thought of as forming identical tiny boxes, called unit cells, that fill the space of the lattice. The lengths of the edges of a unit cell and the angles between them are called the lattice parameters. The symmetry properties of the crystal are embodied in its space group.

Unlike other solids, crystals have molecules or ions arranged in a well-defined array. All crystals are held together by attraction between molecules. A crystal's structure and symmetry play a role in determining many of its physical properties, such as cleavage, electronic band structure, and optical transparency. Crystalline solids show a definite melting point, passing rather sharply from solid to liquid state. The amount of heat required to convert a unit mass of a crystalline solid at its melting point into a liquid without an increase in temperature is defined as heat of fusion or 4 Hr. The physical properties of melting point and solubility are related to the strength of attractive or intermolecular forces between molecules. Due to the highly organized, lattice-like structures of crystalline solids, they typically require a significant amount of energy for melting or solubilization. The energy required for a drug molecule to escape from a crystal, for example, is greater than is required for the same drug molecule to escape from a non-crystalline, amorphous form.

Heat of fusion (ΔHf) of a sample is thus also a measure of the amount of heat that must be introduced to convert its crystalline fraction to the disordered state. It is thus uniquely dependent upon the degree of crystallinity of the sample and the theoretical heat of fusion of a 100% crystalline sample. For a decrystallized sample, the lower the value of heat of fusion, the less crystalline the sample is. A completely decrystallized sample has a negligible amount of heat of fusion. The crystallization inhibition agent (CIA) is an agent, which reduces the crystal bonds between the molecules of a drug or API, and thereby lowering the heat of fusion of the drug or API in the dosage form of the invention. In some embodiments, the crystallization inhibition agent is a decrystallizing agent, i.e., it reduces the number/amount of crystals that exist in a formulation. In some embodiments, the crystallization inhibition agent prevents formation of crystals in a formulation. In the oral transmucosal dosage form of the invention, the CIA system is a single CIA or a combination of at least two CIAs.

The present invention offers a unique way to identify and further evaluate the crystallization inhibition ability of a CIA system via the measurement of the heat of fusion of the drug. Moreover, the present invention provides an innovative mathematic model to predict or calculate a composition of a CIA containing system comprising a drug having a desired extent or magnitude of the reduced crystal bonds between the molecules or a desired degree of the reduced crystallinity. Thus, the present invention offers a novel way of designing an oral transmucosal dosage form of a pre-calculated formulation composition comprising a drug having a desired degree of the reduced crystallinity and subsequently tailored and improved in-vivo permeation and absorption.

In some embodiments, an oral transmucosal dosage form comprises a CIA system and a drug, wherein the CIA completely or substantially reduces the crystal bonds between the drug molecules i.e., decrystallize the drug. Thus, the drug and CIA exist in non-separable form. They are not covalently bonded, but are mixed at a molecular level. During dissolution of the drug from the solid pharmaceutical composition, e.g., in the oral cavity, both the drug and the CIA (s) dissolve simultaneously and are released into the surrounding fluid. In this fluid in the vicinity of the dissolving surface there will be a gradient of CIA and drug saturation with the region adjacent to the surface of the solid undissolved pharmaceutical composition having the highest concentration of dissolved CIA and drug. Per diffusion layer theory, the concentration of CIA is at or close to saturation level at the interface between the solid dosage form and the solvent (saliva). The presence of a high concentration of CIA in the vicinity of the dissolving dosage form helps maintain the drug in solution at a relatively higher concentration and prevents drug recrystallization or precipitation in the oral cavity. Thus, the CIA keeps the drug in its molecular form in vivo, and the presence of the CIA in the formulation improves oral mucosa permeability and hence enhances drug bioavailability.

In addition, the present invention offers a unique way of making or manufacturing by first creating a reduced crystal bonds between molecules of the drug, then achieving a dosage form comprising the drug having the reduced bonds between molecules, and finally maintain the physic-chemical stability of the dosage form comprising the drug having the reduced bonds between molecules throughout its shelf life.

The present invention also offers a unique way of making or manufacturing by first creating a completely or substantially decrystallized drug, then achieving a dosage form comprising a completely or substantially decrystallized drug, and finally maintaining the physico-chemical stability of the dosage form comprising a completely or substantially decrystallized drug throughout its shelf life.

In some embodiments, the invention is directed to an oral transmucosal dosage form comprising (a) a primary vehicle comprising (i) a CIA system, and (ii) a drug; and (b) a secondary vehicle comprising (i) a hydrophilic water soluble component, and (ii) a texturizing agent, wherein said oral transmucosal dosage form comprises the drug having a desired extent or magnitude of the reduced crystal bonds between the molecules or a desired degree of the reduced crystallinity.

In some embodiments, the invention is directed to an oral transmucosal dosage form comprising (a) a primary vehicle comprising (i) a CIA system, and (ii) a drug; and (b) a secondary vehicle comprising (i) a hydrophilic water soluble component, and (ii) a texturizing agent, wherein said oral transmucosal dosage form comprises the drug having a completely or substantially decrystallized form. In some embodiments, the dosage form comprises a drug having at least a 50% reduction in crystallinity as measured by AUC using a DSC thermogram relative to a dosage form not comprising a CIA. In some embodiments, the dosage form comprises a drug having at least a 55%, at least 60%, at least 65%, at least 70%, at least 75%, at least 80%, at least 85%, at least 90%, at least 95%, at least 96%, at least 97%, at least 98%, at least 99%, at least 99.5% reduction in crystallinity as measured by AUC using a DSC thermogram relative to a dosage form not comprising a CIA.

In some embodiments, the reduction in crystallinity of the drug is dependent on the ratio of drug to CIA. In some embodiments, the drug/CIA ratio is 1:1, 1:2, 1:3, 1:4, 1:5, 1:6, 1:7, 1:8, 1:9, 1:10, 1:12, 1:14, 1:16, 1:20, 1:25, 1:30, 1:35, 1:40, 1:50, 1:60, 1:70, 1:80, 1:90, 1:100, 1:150, 1:200, 1:250, 1:300, 1:400, 1:500, 1:750, or 1:1000.

In some embodiments, the invention is directed to an oral transmucosal dosage form comprising (a) a primary vehicle comprising (i) a CIA system, and (ii) a drug; and (b) a secondary vehicle comprising (i) a hydrophilic water soluble component, and (ii) a texturizing agent, wherein said oral transmucosal dosage form comprises the primary vehicle showing increased permeability across the mouth mucosa. For example, in some embodiments, improved permeability is measured by increased permeability across a polysulfone membrane relative to a dosage form not comprising a CIA. See, e.g., Example 12 and 13. In some embodiments, there is greater than 10%, greater than 20%, greater than 30%, greater than 40%, greater than 50%, greater than 60%, greater than 70%, greater than 80%, greater than 90%, greater than 100%, greater than 120%, greater than 150%, greater than 200%, greater than 300% or greater than 500% increase in permeability across a polysulfone membrane. In some embodiments, the permeability across a polysulfone membrane is proportional to the permeability of the mouth mucosa. Thus, in some embodiments, addition of the CIA as described herein provides for increased permeability across the mouth mucosa as demonstrated by increased permeability across a polysulfone membrane.

In some embodiments, the invention is directed to an oral transmucosal dosage form comprising (a) a primary vehicle comprising (i) a CIA system, and (ii) a drug; and (b) a secondary vehicle comprising (i) a hydrophilic water soluble component, and (ii) a texturizing agent, wherein said oral transmucosal dosage form comprises the primary vehicle showing increased permeability across a transmucosal mucosal membrane relative to a dosage form not comprising a CIA. In some embodiments, the increased permeability across a transmucosal membrane can be measure using a NHu-3D oral buccal epithelial mucosal tissue model system. See, e.g., 13. In some embodiments, there is greater than 10%, greater than 20%, greater than 30%, greater than 40%, greater than 50%, greater than 60%, greater than 70%, greater than 80%, greater than 90%, greater than 100%, greater than 120%, greater than 150%, greater than 200%, greater than 300% or greater than 500% increase in permeability across a transmucosal membrane. In some embodiments, the permeability across a transmucosal membrane model system is proportional to the permeability of the mouth mucosa In some embodiments, the invention is directed to method of designing an oral transmucosal dosage form comprising (a) a primary vehicle comprising (i) a CIA system, and (ii) a drug; and (b) a secondary vehicle comprising (i) a hydrophilic water soluble component, and (ii) a texturizing agent, wherein said oral transmucosal dosage form weighs about 250 mg to about 5000 mg, said oral transmucosal dosage form erodes in about 5 to about 60 minutes, but does not disintegrate, and said oral transmucosal dosage form is solid at 37° C.

In some embodiments, the invention is directed to method of designing an oral transmucosal dosage form comprising (a) a primary vehicle comprising (i) a CIA system, and (ii) a drug; and (b) a secondary vehicle comprising (i) a hydrophilic water soluble component, and (ii) a texturizing agent, wherein said oral transmucosal dosage form comprises the drug having a desired extent or magnitude of the reduced crystal bonds between the molecules or a desired degree of the reduced crystallinity.

In some embodiments, the invention is directed to method of designing an oral transmucosal dosage form comprising (a) a primary vehicle comprising (i) a CIA system, and (ii) a drug; and (b) a secondary vehicle comprising (i) a hydrophilic water soluble component, and (ii) a texturizing agent, wherein said oral transmucosal dosage form comprises the drug the drug having a completely or substantially decrystallized form.

In some embodiments, the invention is directed to method of designing an oral transmucosal dosage form comprising (a) a primary vehicle comprising (i) a CIA system, and (ii) a drug; and (b) a secondary vehicle comprising (i) a hydrophilic water soluble component, and (ii) a texturizing agent, wherein said oral transmucosal dosage form comprises the primary vehicle showing increased permeability across the mouth mucosa.

In some embodiments, the invention is directed to a method of making an oral transmucosal dosage form comprising (a) a primary vehicle comprising (i) a CIA system, and (ii) a drug; and (b) a secondary vehicle comprising (i) a hydrophilic water soluble component, and (ii) a texturizing agent, wherein said oral transmucosal dosage form weighs about 250 mg to about 5000 mg, said oral transmucosal dosage form erodes in about 5 to about 60 minutes, but does not disintegrate, and said oral transmucosal dosage form is solid at 37° C.

In some embodiments, the invention is directed to a method of making an oral transmucosal dosage form comprising (a) a primary vehicle comprising (i) a CIA system, and (ii) a drug; and (b) a secondary vehicle comprising (i) a hydrophilic water soluble component, and (ii) a texturizing agent, wherein said oral transmucosal dosage form comprises the drug having a desired extent or magnitude of the reduced crystal bonds between the molecules or a desired degree of the reduced crystallinity.

In some embodiments, the invention is directed to a method of making an oral transmucosal dosage form comprising (a) a primary vehicle comprising (i) a CIA system, and (ii) a drug; and (b) a secondary vehicle comprising (i) a hydrophilic water soluble component, and (ii) a texturizing agent, wherein said oral transmucosal dosage form comprises the drug the drug having a completely or substantially decrystallized form.

The present invention can be directed to a method of making an oral transmucosal dosage form comprising (a) a primary vehicle comprising (i) a CIA system, and (ii) a drug; and (b) a secondary vehicle comprising (i) a hydrophilic water soluble component, and (ii) a texturizing agent, wherein said oral transmucosal dosage form comprises the primary vehicle showing improved, i.e., increased, permeability across the mouth mucosa.

In some embodiments, the invention is directed to a method of administering an oral transmucosal dosage form comprising (a) a primary vehicle comprising (i) a CIA system, and (ii) a drug; and (b) a secondary vehicle comprising (i) a hydrophilic water soluble component, and (ii) a texturizing agent, wherein said oral transmucosal dosage form weighs about 250 mg to about 5000 mg, said oral transmucosal dosage form erodes in about 5 to about 60 minutes, but does not disintegrate, and said oral transmucosal dosage form is solid at 37° C.

In some embodiments, the invention is directed to a method of administering an oral transmucosal dosage form comprising (a) a primary vehicle comprising (i) a CIA system, and (ii) a drug; and (b) a secondary vehicle comprising (i) a hydrophilic water soluble component, and (ii) a texturizing agent, wherein said oral transmucosal dosage form comprises the drug having a desired extent or magnitude of the reduced crystal bonds between the molecules or a desired degree of the reduced crystallinity.

In some embodiments, the invention is directed to a method of administering an oral transmucosal dosage form comprising (a) a primary vehicle comprising (i) a CIA system, and (ii) a drug; and (b) a secondary vehicle comprising (i) a hydrophilic water soluble component, and (ii) a texturizing agent, wherein said oral transmucosal dosage form comprises the drug having a completely or substantially decrystallized form.

In some embodiments, the invention is directed to a method of administering an oral transmucosal dosage form comprising (a) a primary vehicle comprising (i) a CIA system, and (ii) a drug; and (b) a secondary vehicle comprising (i) a hydrophilic water soluble component, and (ii) a texturizing agent, wherein said oral transmucosal dosage form comprises the primary vehicle showing increased permeability across the mouth mucosa.

In some embodiments, the invention is directed to an oral transmucosal dosage form comprising (a) a primary vehicle comprising (i) a CIA system, and (ii) a drug; and (b) a secondary vehicle comprising (i) a hydrophilic water soluble component, and (ii) a texturizing agent, wherein said oral transmucosal dosage form comprises a CIA system of a single CIA or a combination of CIAs selected from at least two of the following: (1) a hydrophilic CIA; 2) a lipophilic CIA; and (3) an amphiphilic CIA.

In some embodiments, the invention is directed to an oral transmucosal dosage form comprising (a) a primary vehicle comprising (i) a CIA system, and (ii) a drug; and (b) a secondary vehicle comprising (i) a hydrophilic water soluble component, and (ii) a texturizing agent, wherein the drug in the said oral transmucosal dosage form is testosterone.

In some embodiments, the invention is directed to an oral transmucosal dosage form comprising (a) a primary vehicle comprising (i) a CIA system, and (ii) a drug; and (b) a secondary vehicle comprising (i) a hydrophilic water soluble component, and (ii) a texturizing agent, wherein the drug in the said oral transmucosal dosage form is 17β-estradiol.

In some embodiments, the invention is directed to a method of making an oral transmucosal dosage form comprising the steps of i) providing a CIA selected from the group consisting of a hydrophilic CIA, an amphiphilic CIA, or a lipophilic CIA; ii) apply heat to melt said CIA, and mixing to create a molten mixture; iii) adding a drug to said molten mixture, and mixing said drug and said molten mixture; iv) cooling said molten mixture to solidify and milling said molten mixture to form a powder primary vehicle; v) adding a secondary vehicle to said powder primary vehicle and mixing; and vi) compressing said secondary vehicle and powder primary vehicle into an oral transmucosal dosage form, wherein said transmucosal dosage form is about 250 mg to about 5000 mg, erodes in about 5 to about 60 minutes, but does not disintegrate, and is solid at 37° C.

In some embodiments, the invention is directed to a method of making an oral transmucosal dosage form comprising the steps of i) providing a CIA or multiple CIAs selected from the group consisting of hydrophilic, amphiphilic or lipophilic CIAs; ii) applying heat to melt said CIA(s) and mixing to create a molten mixture; iii) adding and solubilizing a drug to said molten mixture; iv) mixing specific components of the secondary vehicle with said molten mixture in either elevated or room temperature; v) cooling the resultant mixture if necessary; vi) milling the resultant mixture to form a powder primary vehicle; vii) adding the remaining portion of the secondary vehicle to said powder primary vehicle and mixing to form an uniform blend; viii) compacting the said uniform blend into an oral transmucosal dosage form, wherein said transmucosal dosage form is about 250 mg to about 5000 mg, erodes in about 5 to 60 minutes and is solid at 37° C.

In some embodiments, the invention is directed to a method of making an oral transmucosal dosage form comprising the steps of i) selecting of one or multiple hydrophilic CIAs; ii) preparing a physical mixture of a drug or active pharmaceutical ingredient with said CIA(s); iii) solubilizing the mixture in a common solvent or a mixture of multiple solvents; iv) mixing this solution with the hydrophilic water soluble component or components of the secondary vehicle; v) evaporating the solvent(s) and milling the mixture to form a powder primary vehicle; vi) adding the remaining portion of secondary vehicle to said powder primary vehicle and mixing; vii) compressing said mixture of primary and secondary vehicles into an oral transmucosal dosage form, wherein said transmucosal dosage form is about 250 mg to about 5000 mg, erodes in about 5 to 60 minutes, but does not disintegrate, and is solid at 37° C.

In some embodiments, the invention is directed to a method of making an oral transmucosal dosage form packaged in high density polyethylene (HDPE) or glass bottles with or without desiccant or in blisters coated with moisture and/or oxygen barrier polymer film.

In some embodiments, the invention is directed to a method of making an oral transmucosal dosage form having an extended shelf life, such as two years when stored at room temperature.

In some embodiments, the invention is directed to a method of providing a drug to someone in need thereof, comprising administering any of the dosage forms described herein.

In some embodiments, the invention is directed to a method of administering of an oral transmucosal dose form with ease of administration.

In some embodiments, the invention is directed to a method of administering of an oral transmucosal dose form with a desired dosing frequency, such as less than or equal to three times a day.

In some embodiments, the invention is directed to a method of administering of an oral transmucosal dose form to someone in need with compliance.

In some embodiments, the invention is an oral transmucosal dosage form that is solid at 37° C. and comprises a hydrophilic crystallization inhibition agent (CIA); a lipophilic CIA; and/or an amphiphilic CIA capable of forming a solid solution, solid emulsion, or solid microemulsion.

The terms "a" or "an" when used to describe embodiments of the invention, means one or more.

Drug refers to the active pharmaceutical ingredient (API) in the dosage form. There may be one or more drugs in the dosage form of the invention.

Hydrophilic means high affinity for water and is used herein to refer to the tendency of a chemical compound to interact with polar solvents, in particular with water, or with other polar groups, and to be soluble, miscible or dispersible in water.

Lipophilic means high affinity for lipid and is used herein to refer to a chemical compound having a tendency to dissolve in lipid-like (e.g. hydrocarbon) solvents. Lipophilic compounds are generally hydrophobic.

Amphiphilic means a chemical compound having distinct polar (hydrophilic) and nonpolar (lipophilic) regions in the same molecule, and exhibit both hydrophilic and lipophilic properties.

In a preferred embodiment of the invention the oral transmucosal dosage form comprises a primary vehicle comprising a drug, a hydrophilic CIA polyethylene glycol, and a secondary vehicle wherein said transmucosal dosage form is about 250 to about 5000 mg, erodes between about 5 to about 60 minutes, and is solid at 37° C.

The present invention can be directed to an oral transmucosal dosage form comprising (a) a primary vehicle comprising (i) a CIA, (ii) optionally a stabilizing agent and (iii) a drug; and (b) a secondary vehicle comprising (i) a hydrophilic water soluble component, and (ii) a texturizing agent, wherein said oral transmucosal dosage form weighs about 250 mg to about 5000 mg, said oral transmucosal dosage form erodes in about 5 to about 60 minutes, but does not disintegrate, and said oral transmucosal dosage form is solid at 37° C.

In some embodiments, the invention is directed to an oral transmucosal dosage form comprising (a) a primary vehicle comprising (i) at least two CIAs, (ii) optionally a stabilizing agent and (iii) a drug; and (b) a secondary vehicle comprising (i) a hydrophilic water soluble component, and (ii) a texturizing agent, wherein said oral transmucosal dosage form weighs about 250 mg to about 5000 mg said oral transmucosal dosage form erodes in about 5 to about 60 minutes but does not disintegrate, and said oral transmucosal dosage form is solid at 37° C.

In some embodiments, the invention is directed to an oral transmucosal dosage form comprising (a) a primary vehicle comprising (i) a combination of CIAs selected from at least two of the following: (1) a hydrophilic CIA; (2) a lipophilic CIA and (3) an amphiphilic CIA; (ii) a stabilizing agent if necessary and (iii) a drug; and (b) a secondary vehicle comprising (i) a hydrophilic water soluble component, and (ii) a texturizing agent, wherein said oral transmucosal dosage form weighs about 250 mg to about 5000 mg, said oral transmucosal dosage form erodes in about 5 to about 60 minutes, but does not disintegrate, and said oral transmucosal dosage form is solid at 37° C.

In some embodiments, the invention is directed to an oral transmucosal dosage form comprising (a) a primary vehicle comprising (i) a binary CIA system, wherein the binary CIA system is monophasic; (ii) optionally a stabilizing agent and (iii) a drug; and (b) a secondary vehicle comprising (i) a hydrophilic water soluble component, and (ii) a texturizing agent, wherein said oral transmucosal dosage form weighs about 250 mg to about 5000 mg, said oral transmucosal dosage form erodes in about 5 to about 60 minutes but does not disintegrate, and said oral transmucosal dosage form is solid at 37° C.

In some embodiments, the invention is directed to an oral transmucosal dosage form comprising (a) a primary vehicle comprising (i) a ternary CIA system, wherein the ternary CIA system is monophasic; (ii) a stabilizing agent if necessary and (iii) a drug; and (b) a secondary vehicle comprising (i) a hydrophilic water soluble component, and (ii) a texturizing agent, wherein said oral transmucosal dosage form weighs about 250 mg to about 5000 mg, said oral transmucosal dosage form erodes in about 5 to about 60 minutes but does not disintegrate, and said oral transmucosal dosage form is solid at 37° C.

The transmucosal dosage form in the current invention can be packaged in high density polyethylene (HDPE) or glass bottles with or without desiccant or can be blister packaged in moisture and/or oxygen barrier polymer film. The polymers used for this purpose may include but not limited to polyvinyl chloride (PVC), Polyvinylidene chloride (PVDC), Polychlorotrifluoroethylene (PCTFE), Cyclic olefin copolymers or polymers (COC or COP)

In some embodiments, the primary vehicle is monophasic.

In some embodiments, the dosage form erodes slowly without disintegration, at a rate of about 5 mg/min to about 500 mg/min. In some embodiments, at least 40% of the drug is released from said dosage form within 5 minutes, or alternatively 10 minutes, as measured using the glass bead rotating bottle method with 150 ml SSF. In some embodiments, at least 50% of the drug is released from said dosage form within 15 minutes, as measured using the glass bead rotating bottle method with 150 ml SSF. In some embodiments, the dosage form erodes in about 10 to about 30 minutes.

In some embodiments, the dosage form weighs about 2000 mg to about 3000 mg.

In some embodiments, the CIA is vitamin E-TPGS. In some embodiments, the CIA is a PEG having a molecular weight greater than or equal to about 1450. In some embodiments, the CIA is PEG-8000. In some embodiments, the CIA is selected from the group consisting of hydrogenated vegetable oil, cocoa butter, carnauba wax, beeswax, and combinations thereof. In some embodiments, the CIA is selected from the group consisting of a lauroyl macrogolglyceride, a stearoyl macrogolglyceride, a linoleoyl macrogol-6 glyceride, an oleoyl polyoxyl-6 glyceride, a lauroyl macrogol-6 glyceride, oleic acid, vitamin E-TPGS, a sucrose ester, lecithin, and combinations thereof. In some embodiments, the CIA is Polyvinylpyrrolidone (PVP) having a molecular weight greater than or equal to 1000. In some embodiments, the CIA is a vinylpyrrolidone-vinyl acetate co-polymer. In some embodiments the CIA is a polyvinyl caprolactum-polyvinyl acetate-polyethylene glycol graft co-polymer.

In some embodiments, the secondary vehicle comprises one or more of isomalt, mannitol, sucrose, xylitol, mannitol, sorbitol or combinations thereof. In some embodiments, the secondary vehicle comprises sorbitol, xylitol and/or mannitol. In some embodiments, the texturizing agent is one or more of xanthan gum, lecithin and/or sodium alginate.

In some embodiments, the dosage form of the present invention is suitable for administering any drug across the oral mucosa, including, but not limited to very soluble drugs, freely soluble drugs, soluble drugs, sparingly soluble drugs, slightly soluble drugs, very slightly soluble drugs, and/or practically insoluble drugs. Definitions of each type of drug are as follows:

| Solubility Definition | Parts of water required for one part of drug | Solubility range (mg/ml) |
|---|---|---|
| Very soluble | <1 | >1,000 |
| Freely soluble | From 1 to <10 | 100-1,000 |
| Soluble | From 10 to <30 | 33-100 |
| Sparingly soluble | From 30 to <100 | 10-33 |
| Slightly soluble | From 100 to <1,000 | 1-10 |
| Very slightly soluble | From 1,000 to <10,000 | 0.1-1 |
| Practically insoluble | ≥10,000 | <0.1 |

In some embodiments, the drug is a practically insoluble, very slightly soluble, slightly soluble, sparingly soluble, soluble, freely soluble, or very soluble drug. In some embodiments, the drug is a practically insoluble, very slightly soluble, slightly soluble, sparingly soluble, soluble, or freely soluble drug. In some embodiments, the drug is a practically insoluble, very slightly soluble, slightly soluble, sparingly soluble, or soluble drug. In some embodiments, the drug is a practically insoluble, very slightly soluble, slightly soluble, or sparingly soluble drug. In some embodiments, the drug is a practically insoluble, very slightly soluble, or slightly soluble drug. In some embodiments, the drug is a practically insoluble, or very slightly soluble drug. In some embodiments, the drug is a practically insoluble drug. In some embodiments, the drug is a very slightly soluble drug. In some embodiments, the drug is a slightly soluble drug. In some embodiments, the drug is a sparingly soluble drug. In some embodiments, the drug is a soluble drug. In some embodiments, the drug is a freely soluble drug. In some embodiments, the drug is a very soluble drug. In some embodiments, the drug of the present invention having lower solubility (e.g., practically insoluble, very slightly soluble, slightly soluble drug) has improved transmucosal permeability when formulated as provided herein.

In some embodiments, the drug is testosterone. In some embodiments, the drug comprises 0.1-20% of the weight of said primary vehicle.

In some embodiments, the drug is 17β-estradiol hemihydrate. In some embodiments, the drug comprises 0.01-20% of the weight of said primary vehicle.

In some embodiments, the invention is directed to an oral transmucosal dosage form comprising (a) a primary vehicle comprising (i) a hydrophilic CIA, (ii) a lipophilic CIA, (iii) an amphiphilic CIA, and (iv) testosterone; and (b) a secondary vehicle comprising (i) a hydrophilic water soluble component, and (ii) a texturizing agent, wherein said oral transmucosal dosage form weighs about 250 mg to about 5000 mg, said oral transmucosal dosage form erodes in about 5 to about 60 minutes, but does not disintegrate, and said oral transmucosal dosage form is solid at 37° C.

In some embodiment, the invention is directed to an oral transmucosal dosage form comprising a drug, polyethylene glycol having a molecular weight of about 1450 or above, or 3000 or above, and a secondary vehicle wherein said oral transmucosal dosage form weighs about 250 mg to about 5000 mg, said oral transmucosal dosage form erodes in about 10 to about 30 minutes, but does not disintegrate, and said oral transmucosal dosage form is solid at 37° C.

A drug must be in molecular form in the transmucosal fluid to cross a biological membrane, such as the transmucosal membrane. The invention is a dosage form designed to have the drug component exist as a micron, sub-micron or molecular form to provide increasing potential of being absorbed upon discharge from the dosage form.

In some embodiments, the drug is present in the oral transmucosal formulation with completely or substantially reduced crystallinity, while the CIAs may form a monophasic system such as a solid solution, solid microemulsion, or solid emulsion, depending on their properties and proportions. Because the oral transmucosal dosage form of the invention delivers the drug of completely or substantially reduced crystallinity, transmucosal permeability and systemic bioavailability is immediate and improved.

The dosage form containing the solid solution in a hydrophilic CIA serves as a drug reservoir. Drug release rate can be controlled or tailored via varying the composition. Selection of CIAs to form an emulsion, or microemulsion, solid at 37° C., instead of a solid solution, may be used to optimize release of the drug.

The primary vehicle comprising the solid (at 37° C.) solution, emulsion, or microemulsion of the drug is embedded in a secondary vehicle.

The dosage form of the invention may be in any form that can dissolve in saliva and be held in the oral cavity while it dissolves, e.g., a lozenge, troche, tablet or a lollipop. This lozenge, troche, tablet or lollipop can be palatable, and preferably erodes slowly without disintegration, at a rate of about 5 mg/min to about 500 mg/min, e.g. it may erode at about 150 mg/min, in the oral cavity, reaching complete erosion in 5 to 60 minutes, e.g., in 20 minutes.

Erosion is slow dissolution of the dosage form upon contact with a solvent and occurs at the surface of the dosage form until the dosage form gradually dissolves from the outside in.

Disintegration is when a dosage form breaks into small particles upon contact with a solvent, before significant dissolution occurs.

When the drug molecule is released from the oral transmucosal dosage form of the invention, it is ready to penetrate the oral transmucosal membrane. Drug release is managed via controlled erosion. The erosion is controlled by the formulation of the dosage form.

Some drugs suitable for use in the oral transmucosal dosage forms of the invention are drugs for which the dose each time the drug is administered is a low dose (below 100 mg per dose, preferably below 50 mg, below 20 mg, or below 10 mg, below 1 mg, or below 0.5 mg). Note that administration may be more than once per day). In addition, suitable drugs will have a melting point of greater than 37° C. They also have a low solubility in water. These drugs are class II or class IV drugs according to the Biopharmaceutics Classification System (BCS) Guidance published by the U.S. Food and Drug Administration. Suitable drugs may also be subject to a high first pass effect, or are pH sensitive, and/or may degrade in the presence of digestive enzymes. Thus, in some embodiments, the drug is selected from the group consisting of a drug subject to high first pass effect, a drug sensitive to low pH, and a drug unstable in the presence of digestive enzymes. In some embodiments, the drug is a crystalline drug, i.e., the drug can exist in one or more crystal structures before being formulated as described herein.

Suitable drugs for the oral transmucosal dosage form of the invention include, but are not limited to the following drugs. The drugs may be in free base or free acid form, or as a pharmaceutical salt or ester. Thus, in some embodiments, the drug is in free base form. One of ordinary skill in the art will be able to select the appropriate form for use in the dosage form of the invention.

Bioidentical or synthetic hormones, including those used for hormone replacement or as oral contraceptives, such as testosterone, methyltestosterone, testosterone enanthate, fluoxymesterone, tibolone, drospirenone, estradiol, estradiol valerate levonorgestrel, ethinyl estradiol, desogestrel, dieogest etonogestrel, norethindrone acetate, nomegestrol acetate, norelgestromin, norgestimate, calcitonin, medroxyprogesterone acetate, conjugated estrogens etc.

Nonsteroidal anti-inflammatory drug (NSAID) like meloxicam.

High first pass effect drugs such as imipramine, morphine, buprenorphine, midazolam, meperidine hydrochloride.

Antispasmodic agents like oxybutynin, tolterodine tartrate, solifenacin succinate, darifenacin, trospium chloride, fesoterodine fumarate, dicyclomine, hyoscyamine Anti-hypertensives such as carvedilol.

Anxiolytics & hypnotics such as diazepam, alprazolam, triazolam, ramelteon and buspirone, Corticosteroids such as budesonide.

Antipsychotics such as pimozide

Calcium channel blockers such as felodipine, amlodipine and nefedipine

Alpha-agonist agent such as clonidine, silodosin etc.

Central nervous system (CNS) stimulants such as methylphenidate and dexmethylphenidate Antiemetics such as scopolamine and granisetron Monoamine oxidase inhibitors such as selegiline Antidementia agents such as rivastigmine Dopamine agonist such as rotigotine Prostaglandins such as treprostinil sodium Opiates, narcotics and their agonists, and antagonist, such as hydrocodone, hydromorphone, oxycodone, oxymorphone, naltrexone and methylnaltrexone.

Muscarinic antagonist tropane alkaloids i.e. atropine and hyoscyamine.

Thus, in some embodiments, the drug is selected from the group consisting of a bioidentical or synthetic hormone, a nonsteroidal anti-inflammatory drug, an antispasmodic agent, an anti-hypertensive, an anxiolytic or hypnotic agent, a corticosteroid, an antipsychotic, a calcium channel blocker, an alpha-agonist, a central nervous system stimulant, an antiemetic, a monoamine oxidase inhibitor, an antidementia agent, a dopamine agonist, a prostaglandin, an opiate, a narcotic, or a muscarinic antagonist tropane alkaloid, and combinations thereof.

The oral transmucosal dosage form comprises two vehicles, a primary vehicle and a secondary vehicle. These vehicles comprise various components as described below.

1. Primary Vehicle

The primary vehicle comprises of a CIA system of single or multiple CIAs and when required a single or multiple stabilizing agents. In the finished dosage form, the primary vehicle carries the drug as a solid state molecular dispersion, solid microemulsion or solid emulsion. In the oral transmucosal dosage form, the CIA can carry the drug as a solid state molecular dispersion. In the primary vehicle, the drug can be non-crystalline, as can be determined by analyzing the primary vehicle of dosage form of the invention using methods such as x-ray crystallography, particularly x-ray powder diffraction. The drug concentration in the primary vehicle is typically less than about 70% calculated as a percentage of the total weight of the primary vehicle, and is preferably less than about 50%, and is more preferably less than about 30% or less than about 20%, and is most preferably about 0.1-15%, or about 0.5-10%, by weight, of the primary vehicle. The melting point or the glass transition temperature (Tg) of the primary vehicle can be >25° C. The primary vehicle can be soluble or dispersible in saliva or other aqueous systems. The primary vehicle comprises of one or more of the following crystallization inhibition agents (CIA):

a) A Hydrophilic CIA

A hydrophilic CIA is a CIA that is hydrophilic. A CIA is an agent that reduces crystallinity of the active ingredient in the dosage form, partially to a desired degree of crystallinity or completely to a decrystallized form. Examples of hydrophilic CIAs that can be used in the dosage forms of the invention include one or more polyethylene glycols (PEG) having a molecular weight ≥2000 which is solid at room temperature. The hydrophilic CIA is preferably a PEG having a molecular weight ≥3500, and is most preferably PEG 8000.

The hydrophilic CIA can also include polyvinylpyrrolidone (PVP), vinylpyrrolidone-vinyl acetate co-polymers, polyvinyl caprolactum-polyvinyl acetate-polyethylene glycol graft co-polymers, synthetic copolymers of ethylene oxide and propylene oxide, hydroxyl propyl cellulose, hydroxyl propyl methyl cellulose, hydroxyl propyl methyl cellulose acetyl succinate, polyethylene oxide, acrylic and methacrylic acids and their esters and polymethacrylates.

In some embodiments, the hydrophilic CIA can also comprise disaccharide derived from glucose and fructose, such as sucrose; trioses such as ketotriose (dihydroxyacetone), or aldotriose (glyceraldehyde); tetroses such as ketotetrose (erythulose), aldotetroses (erythrose, threose), or ketohexose (fructose); disaccharides or sugar, lactose, maltose, trehalose, turanose, cellobiose; trisaccharides such as raffinose, melezitose, or maltotriose; tetrasaccharides such as stachyose; oligosaccharides such as fructooligosaccharides (FOS), or galactooligosaccharides (GOS); polysaccharides such as glucose/glucan such as glycogen, starch (amylose, amylopectin), cellulose, dextrin/dextran, beta-glucan (zymosan, lentinan, sizofiran), maltodextrin, fructose/fructan such as inulin, mannose, galactose; polyols such as sugar alcohol or polyols or polyhydric alcohols which are of hydrogenated form of carbohydrate, whose carbonyl group (aldehyde or ketone, reducing sugar) has been reduced to a primary or secondary hydroxyl group; or mixtures thereof. Examples of these can include but are not limited to: xylitol, mannitol, sorbitol, galactilol, volemitol, isomalt, maltitol, and erythritol etc.

b) A Lipophilic CIA

The primary vehicle can also, or alternatively, comprise a lipophilic CIA. Examples of a lipophilic CIA that can be used in the dosage forms of the invention include oleic acid, a hydrogenated vegetable oil, which is mixture of triglycerides of fatty acids (e.g., hydrogenated vegetable oil, one suitable type is sold under the name Lubritab®, JRS Pharma, Germany); cocoa butter, which is a fat of natural origin and comprises a mixture of the triglycerides of saturated and unsaturated fatty acids, in which unsaturated acid is preferentially situated on the 2-position of the triglyceride; carnauba wax; beeswax; or mixtures thereof.

c) An Amphiphilic CIA

The primary vehicle may also, or alternatively, comprise an amphiphilic CIA. Examples of an amphiphilic CIA that may be used in the dosage forms of the invention include polyethylene glycol glycerides composed of mono-, di- and triglycerides and mono- and diesters of polyethylene glycol (PEG), e.g. lauroyl macrogolglycerides, stearoyl macrogolglycerides, linoleoyl macrogol-6 glycerides, oleoyl polyoxyl-6 glycerides, and lauroyl macrogol-6 glycerides, such as those sold under the names Gelucire® or Labrafil®. Additional examples of an amphiphilic CIA include vitamin E-TPGS (d-alpha tocopherol polyethylene glycol 1000 succinate), mono-, di- and tri-esters of sucrose with food fatty acids, prepared from sucrose and methyl and ethyl esters of food fatty acids or by extraction from sucroglycerides such as sucrose esters; lecithin or mixtures thereof.

In some embodiments, the pharmaceutical dosage form of the present invention comprises a stabilizing agent. A "stabilizing agent" refers to a substance that assists the dosage form to maintain its integrity throughout its shelf life. The stabilizing agent(s), when used will be physically integrated as a part of the primary vehicle. A stabilizing agent for instance may refer to preservatives, acidifier, alkanizing agents, anti-oxidants, photoprotectants, chelating agents, preservatives etc. Examples of suitable antioxidants can include butylated hydroxyanisole (BHA), sodium ascorbate, butylated hydroxytoluene (BHT), sodium sulfite, propyl gallate, DL-α-tocopherol, citric acid, malic acid, ascorbic acid or mixtures thereof. The antioxidants can be present at concentrations of, for example, from about 0.01% to about 5% by weight. Examples of chelating agents can include disodium EDTA, edetic acid, citric acid, and combinations thereof. The chelating agents can be present at a concentration of up to approximately 10% by weight of the composition, for example, from about 0.01 to about 5% by weight. The term "photoprotectant" as used herein means an agent for protection from the chemical or physical effects of light on a statin formulation. Examples can include metal oxides such as titanium oxide, ferric oxide or zinc oxide. The photoprotectant can be present at a concentration of up to approximately 10% by weight of the composition, for example, from about 0.01 to about 5% by weight. The alkanizing agents as used herein can include alkali metal salt additives or alkaline earth metal salt additives. Alkali metal salt additives can be, for example, sodium carbonate, sodium hydroxide, sodium silicate, disodium hydrogen orthophosphate, sodium aluminate and other suitable alkali metal salts. In particular, the alkali metal salt additive can be sodium carbonate or disodium hydrogen orthophosphate. Alkaline earth metal salt additives can include, for example, calcium carbonate, calcium hydroxide, magnesium carbonate, magnesium hydroxide, magnesium silicate, magnesium aluminate, or aluminum magnesium hydroxide. The amount of alkanizing agent may vary from about 1 to about 10% by weight of the composition.

In some embodiments the stabilizing agent used in an anti-oxidant in a concentration of about 0.01%-about 5%, about 0.01%-about 4%, about 0.01%-about 3%, about 0.01%-about 2%, about 0.01%-about 1% or less than about 1%, by the weight of the dosage form. In some embodiments, the anti-oxidant DL-α-tocopherol is present in the dosage forms of the present invention in a concentration of about 0.01%-about 5%, about 0.01%-about 4%, about 0.01%-about 3%, about 0.01%-about 2%, about 0.01%-about 1% or less than about 1%, by the weight of the dosage form.

In some embodiments, the dosage form can comprise a single CIA. In some embodiments, the dosage form can comprise multiple CIAs. In some embodiments, the combination of CIAs is selected from at least two of the following: a hydrophilic CIA, a lipophilic CIA, and an amphiphilic CIA. For example, in some embodiments, the primary vehicle comprises a hydrophilic CIA and a lipophilic CIA. In some embodiments, the primary vehicle comprises a hydrophilic CIA and an amphiphilic CIA. In some embodiments, the primary vehicle comprises a lipophilic CIA and an amphiphilic CIA. In some embodiments, the primary vehicle can comprise more than one hydrophilic CIA, more than one lipophilic CIA, and/or more than one amphiphilic CIA. In some embodiments, the dosage form can comprise three CIAs, or greater than three CIAs. In some embodiments, the primary vehicle comprises at least three CIAs, wherein at least one CIA is selected from each of the following groups: a hydrophilic CIA, a lipophilic CIA, and an amphiphilic CIA. In some embodiments, the one CIA, at least two CIAs, at least three CIAs, at least four CIA, or at least five CIAs are monophasic.

In some embodiments, the primary vehicle comprises two CIAs, wherein the CIAs are selected from at least two of the following: a hydrophilic CIA, a lipophilic CIA, and an amphiphilic CIA, wherein the binary CIA system (i.e., the two CIAs) is monophasic. In some embodiments, the primary vehicle comprises three CIAs, wherein the CIAs in the ternary CIA system (i.e., the three CIAs) are selected from at least three of the following: a hydrophilic CIA, a lipophilic CIA, and an amphiphilic CIA. In some embodiments, the three CIAs are monophasic, and can be in any ratio suitable for forming a monophasic system. Suitable ratios that can be used to create a monophasic CIA system can be determined by following Example 14, and illustrated in the phase diagrams found in FIGS. 23-35. In some embodiments, the CIAs are present in a ratio of 1 to 5 hydrophilic CIA: 0.5 to 3 lipophilic CIA: 2 to 8 amphiphilic CIA. In some embodiments, the CIAs are present in a ratio of about 4 hydrophilic CIAs: about 1 lipophilic CIA: about 5 amphiphilic CIAs.

2. Secondary Vehicle

The primary vehicle containing the drug dispersed in a single or multiple CIAs can further be dispersed in a diluent or bulking agent called the Secondary Vehicle. The Secondary Vehicle can be predominantly a hydrophilic mass. The Secondary Vehicle comprises one or both of a hydrophilic water soluble component and a texturizing agent. Preferably, the secondary vehicle is compressible. The secondary vehicle can also comprise additional excipients such as lubricants and flavoring and sweetening agents. The secondary vehicle can be composed of at least about 50%, preferably at least about 80%, and most preferably, at least about 90% of a hydrophilic water soluble component.

a) A Hydrophilic Water Soluble Component

The hydrophilic water soluble component is typically a bulking agent, and where compression is used to prepare the oral transmucosal dosage form, it may be compressible. Examples of a hydrophilic water soluble component that may be used in the dosage forms of the invention include disaccharide derived from glucose and fructose, such as sucrose; trioses such as ketotriose (dihydroxyactone), or aldotriose (glyceraldehyde); tetroses such as ketotetrose (erythulose), aldotetroses (erythrose, threose), or ketohexose (fructose); disaccharides or sugar, lactose, maltose, trehalose, turanose, cellobiose; trisaccharides such as raffinose, melezitose, or maltotriose; tetrasaccharides such as stachyose; oligosaccharides such as fructooligosaccharides (FOS), or galactooligosaccharides (GOS); polysaccharides such as glucose/glucan such as glycogen, starch (amylose, amylopectin), cellulose, dextrin/dextran, beta-glucan (zymosan, lentinan, sizofiran), maltodextrin, fructose/fructan such as inulin, mannose, galactose; polyols such as sugar alcohol or polyols or polyhydric alcohols which are of hydrogenated form of carbohydrate, whose carbonyl group (aldehyde or ketone, reducing sugar) has been reduced to a primary or secondary hydroxyl group; or mixtures thereof. Examples of these may include, but are not limited to, xylitol, mannitol, sorbitol, galactilol, volemitol, isomalt, erythriol, and combinations thereof.

b) A Texturizing Agent:

The texturizing agent is polymer that provides a smooth and pleasing texture to the oral transmucosal dosage form. The polymers can also help provide the erodible characteristic of the dosage form. In addition, they can act as a binder in oral transmucosal dosage forms of the invention that are prepared by compression. In addition, these polymers may provide a smooth and pleasing texture to the oral dosage form. Examples of a texturizing agent that can be used in the dosage forms of the invention include one or more polysaccharides of natural origin, capable of causing an increase in viscosity of solution, even at small concentrations. The texturizing agents can include gums such as acacia, tragacanth, xanthan gum and alginates (e.g., alginic acid and sodium alginate). The texturizing agents also can include agar, carrageenan, gum ghatti, karaya gum, guar gum, locust bean gum, beta-glucan, chicle gum, dammar gum, glucomannan, mastic gum, psyllium seed husks, spruce gum, tara gum, and gellan gum. Additional examples of texturizing agents include polycarbophil, calcium polycarbophil, hydroxypropyl methyl cellulose, methylcellulose, hydroxypropyl cellulose, hydroxyethyl cellulose and carboxymethylcellulose sodium, carbomer, lecithin, carboxymethyl cellulose (CMC) or cellulose gum. Cocoa butter, which is a fat of natural origin and comprises a mixture of the triglycerides of saturated and unsaturated fatty acids, in which unsaturated acid is preferentially situated on the 2-position of the triglyceride. These texturizing agents may also have bioadhesive properties such as polycarbophil or calcium polycarbophil. Mixtures of texturizing agents can also be used.

One of skill in the art will recognize that additional pharmaceutically acceptable excipients can be used in the present invention including those listed in The Handbook of Pharmaceutical Excipients, 5th Ed., The Pharmaceutical Press and American Pharmacists Association, London, UK and Washington, D.C. (2006) and Remington: The Science and Practice of Pharmacy, Lippincott Williams & Wilkins, 21st Ed. (2005), which are incorporated herein by reference in their entirety.

The dosage form comprises a primary vehicle and a secondary vehicle. The ratio of the primary to secondary vehicles can vary, e.g., the ratio can be between about 1:5 to about 1:100, and preferably may be about 0.5:1, 1:1, 1:10, 1:25, or 1:50. In some embodiments, the secondary vehicle is not in a homogeneous solution with the primary vehicle. For example, the dosage form can comprise the primary vehicle in a monophasic powder homogeneously dispersed, but not in solution with, the secondary vehicle.

The oral transmucosal dosage form of the invention can have the following physical attributes.

In some embodiments, the dosage form is an erosion controlled solid dosage form. It erodes rather than disintegrates, as defined earlier. Complete erosion of the oral transmucosal dosage form in the mouth may take up to one hour. In some embodiments, the erosion time is more than about 5 minutes but less than about 60 minutes. In some embodiments, the erosion time is about 10 to about 30 minutes or about 15 to about 30 minutes.

The oral transmucosal dosage form of the invention can be between about 250 to about 5000 mg, about 1000 mg to about 4000 mg, about 1000 to about 3000 mg, about 1500 mg to about 2500 mg, about 2000 mg or about 2500 mg. In some embodiments, the dosage form of the invention can be between about 250 to about 5000 mg, about 250 mg to about 2500 mg, about 250 mg to about 2000 mg, about 250 mg to about 1500 mg, or about 250 mg to about 1000 mg.

In some embodiments, the oral transmucosal dosage form of the invention is a solid mass with a suitable dimension that has a hardness of >10 Kp, preferably about 15 to about 50 Kp. Pharmaceutical dosage forms of the present invention can have a hardness which makes them stable during preparation, packaging and storage. As used herein, "hardness" refers to the degree of force required to break, crumble or crack the pharmaceutical dosage forms. Hardness can be described in units of kilograms/mm$^2$ (kg/mm$^2$), pounds/in$^2$ pounds/in$^2$ (psi), Pascals (Pa), Newtons/m$^2$ (N/m$^2$), kilopounds (kp). The hardness of the pharmaceutical dosage forms can be measured, for example, using a tablet hardness tester.

The oral transmucosal dosage form of the invention can have a calculated density greater than or equal to about 1 g/cc, greater than or equal to about 1.2 g/cc, greater than or equal to about 1.5 g/cc, or greater than or equal to about 2.0 g/cc.

The specific surface area of the oral transmucosal dosage form of the invention can be greater than or equal to about 2 cm$^2$/gm. greater than or equal to about 4 cm$^2$/gm, or greater than or equal to about 6 cm$^2$/gm.

The following process, which is depicted in FIG. 1, can be used to manufacture embodiments of the invention:
1. Apply heat to melt the mixture of hydrophilic CIA, amphiphilic CIA and lipophilic CIA.
2. Mix the molten mixture.
3. Disperse the drug in the molten mixture.
4. Once the entire molten mixture is mixed well, stop heating and start cooling.
5. Mill the solidified mixture through a mill, e.g., Fitzmill, to form a powder.
6. Mix the powdered dry emulsion with the secondary vehicle.
7. Add any additional excipients, e.g., lubricant, glidant, flavorant, and sweetener and mix well.
8. Compress into a lozenge, troche, tablet or lollipop.

Alternatively another process can be applied to prepare some embodiments of the invention is described below:
1. Melt a single or a mixture of CIAs selected from hydrophilic, lipophilic and amphiphilic CIAs.
2. Add appropriate stabilizing agent if necessary.
3. Add drug or active pharmaceutical ingredient to molten CIA(s) and mixing.
4. Mix an appropriate portion of the secondary vehicle with the molten mixture at either elevated or at room temperature.
5. Cool the resultant mixture if necessary.
6. Mill the resultant mixture through a mill, e.g., Fitzmill, to form a powder, this will serve as the primary vehicle.
7. Mix the remaining portion of the secondary vehicle with the primary vehicle.
8. Add any additional excipients e.g. lubricant, glidant, flavorant, sweetener etc. and mix well.
9. Compress into lozenge, troche, tablet or lollipop.

Another separate process which may also be used in manufacturing some embodiments of the invention is explained below:
1. Mix drug or active pharmaceutical ingredient with one or more hydrophilic CIA(s).
2. Solubilize this mixture in an appropriate solvent or a mixture of solvents.
3. Mix the solution with the hydrophilic water soluble component(s) of the secondary vehicle.
4. Evaporate the solvent(s) using an oven, obtaining a dispersion of the drug in hydrophilic CIA(s) mixed uniformly with a hydrophilic water soluble component, which will act as the primary vehicle.
5. Mill the primary vehicle using a mill, e.g., Fitzmill, to form a powder.
6. Mix the powder from the previous step with the secondary vehicle.
7. Add any additional excipients e.g. lubricant, glidant, flavorant and sweetener and mix well.
8. Compress into lozenge, troche, tablet or lollipop.

In some embodiments, if compression is used in the preparation of the oral transmucosal dosage form of the invention, the secondary vehicle will be crystalline in nature, while the drug in the primary vehicle will not be. In addition, if compression is used, the components selected for the secondary vehicle can exhibit thixotropic behavior (shear thinning property) in aqueous media at the low shear rates typically found in the human mouth. Thixotropy is a property exhibited by certain semisolids of becoming fluid when stirred or shaken and returning to the semisolid state upon standing.

Alternatively, in some embodiments, the oral transmucosal dosage form of the invention can be prepared using a hot melt extrusion process. Where such a process is used, the secondary vehicle can be modified to select suitable components. For example, the texturizing agent can be omitted.

Additional useful pharmaceutically acceptable excipients include those that impart good flow and compression characteristics to a composition that is to be compressed. Pharmaceutically acceptable excipients and additives suitable for use with the present invention include, but are not limited to, binders, lubricants, glidants, sweeteners, flavorants, stabilizers and combinations thereof.

In some embodiments, the pharmaceutical dosage form of the present invention comprises a lubricant. As used herein, a "lubricant" refers to an excipient that improves powder flow thereby preventing adhesion of a compact mass to a surface (e.g., a surface of compression die and/or punch). A lubricant reduces inter particle friction within a substantially homogeneous powder and aid in the ejection of a compressed dosage form from a die cavity after compression. Lubricants suitable for use with the present invention include, but are not limited to, magnesium stearate, calcium stearate, zinc stearate, sodium stearate, stearic acid, aluminum stearate, leucine, glyceryl behenate, sodium lauryl sulfate, sodium stearyl fumarate (e.g., PRUV®, Sohne GmbH & Co., Rosenberg, Germany), colloidal silicon dioxide, calcium silicate, hydrogenated vegetable oil, and combinations thereof. In some embodiments, the lubricant is magnesium stearate, sodium stearyl fumarate, or a combination thereof. In some embodiments the lubricant is colloidal silicon dioxide, calcium silicate, or a combination thereof.

In some embodiments, a lubricant is present in the dosage forms of the present invention in a concentration of about 0.1% to about 10%, about 0.1% to about 6%, about 0.1% to about 5%, about 0.1% to about 4%, about 0.1% to about 3%, about 0.1% to about 2%, or less than about 2% by weight of the dosage form. In some embodiments, magnesium stearate is present in the dosage forms of the present invention in a concentration of about 0.1% to about 3%, about 0.2% to about 2%, about 0.3% to about 3%, about 0.3% to about 1.5%, about 0.6%, about 0.7%, about 0.75%, about 0.8%, about 1%, or about 1.5% by weight of the dosage form. In some embodiments, sodium stearyl fumarate is present in the dosage forms of the present invention in a concentration of about 0.1% to about 10%, about 0.2% to about 5%, about 0.5% to about 3%, about 0.6%, about 0.7%, about 0.75%, about 0.8%, about 1%, about 1.5%, or about 2% by weight of the dosage form. In some embodiments, colloidal silicon dioxide is present in the dosage forms of the present invention in a concentration of about 0.1% to about 2%, about 0.1% to about 1.75%, about 0.1% to about 1.5%, about 0.1% to about 1.25% or about 0.1% to about 1%, by the weight of the dosage form.

In some embodiments of the pharmaceutical dosage form of the present invention, the hydrophilic water soluble component of the Secondary Vehicle is a sweetener. In other embodiments, it is not, but the dosage form further comprises a sweetener. Sweeteners suitable for use with the present invention can have a sweet taste and can be soluble in water (e.g., at least 1 part sweetener can be dissolved in about 10 parts water). Non-limiting examples of natural and artificial sweeteners suitable for use with the present invention can include saccharin sodium, acesulfame potassium, altitame, aspartame, cyclamic acid and its salts (e.g., sodium cyclamate), dihydrochalcones, fructose, glucose, glycerrhizinate, lactose, maltodextrin, monellin, neotame, paratinose, rebulose, stevioside, sucralose, sucrose, thaumatin, and combinations thereof.

In some embodiments, the pharmaceutical dosage form of the present invention comprises a sweetener, but is substantially free of sugar (i.e., "sugar-free"). "Sugar-free" can also refer to a pharmaceutical dosage form that is substantially free of complex carbohydrates and/or polysaccharides that can be readily converted to sugars in the oral cavity. A sugar-free pharmaceutical dosage form can offer reduced caloric value, reduced dental caries and other dental hygienic issues, and can be preferable for administering to subjects seeking to control sugar intake (i.e., diabetic subjects). Sugar-free sweeteners suitable for use with the present invention include, but are not limited to, saccharin and salts thereof (e.g., saccharin sodium), acesulfame potassium, altitame, aspartame, cyclamic acid and its salts (e.g., sodium cyclamate), dihydrochalcones, glycerrhizinate, monellin, neotame, saccharin, stevioside, sucralose, thaumatin and combinations thereof.

In some embodiments, a sweetener is present in the pharmaceutical dosage forms of the present invention in a concentration of 0.0005% to about 10%, 0.0005% to about 10%, about 0.001% to about 10%, about 0.1% to about 10%, or about 0.1% to about 5% by weight of the dosage forms. In some embodiments, the sweetener is present in the pharmaceutical dosage forms of the present invention in a concentration of 0.05% to about 5%, about 0.1% to about 2%, about 0.25% to about 1% or about 0.4% to about 0.6% by weight of the dosage form. In some embodiments, the pharmaceutical dosage forms comprises aspartame in a concentration of about 1% to about 10%, about 2% to about 6%, about 2%, about 3%, about 4%, about 5%, or about 6% by weight of the dosage form.

In some embodiments, the pharmaceutical dosage form of the present invention comprises a flavorant. As used herein, a "flavorant" refers to a natural or artificial flavoring that can be added to the pharmaceutical dosage forms to improve their taste, or to mask an unpleasant taste. Flavorants can be combined, as desired, to produce a particular flavor mixture which is compatible with a particular medication. Flavorants suitable for use with the present invention include, but are not limited to, raspberry, strawberry, cherry, almond, citrus fruit, vanilla, vanilla cream, menthol, mint, peppermint, spearmint, wintergreen, grape, coconut, chocolate, menthol, licorice, butterscotch and combinations thereof. Citrus fruit flavorings suitable for use with the present invention include, but are not limited to, orange, tangerine, lemon, lime, lemon-lime, and combinations thereof. A flavorant can be present in the pharmaceutical dosage forms of the present invention in a concentration of about 0.01% to about 10%, about 0.05% to about 5%, about 0.1% to about 5%, by weight of the dosage form. In some embodiments, the flavorant does not exceed 5%.

In some embodiments, the pharmaceutical dosage form of the present invention comprises a colorant. A "colorant" refers to a substance that can be added to the pharmaceutical dosage forms to enhance or modify their color or appearance. A colorant can also be added to the pharmaceutical dosage forms as a code or identifier (i.e., to indicate the manufacturer or dosage). Any type of colorant (i.e., "natural color" and/or "artificial color" such as F.D.&C. dyes) known to be "generally regarded as safe" by the U.S. Food and Drug Administration ("the FDA"), and thus generally used in the confectionary trade, or otherwise approved by the FDA for use in pharmaceutical preparations, can be used with the present invention.

In some embodiments, to promote saliva secretion thereby promoting drug solubility and absorption the dosage form of the present invention comprises an excipient having a —CHCOOH functional group selected from the group consisting of: tartaric acid, citric acid, malic acid, succinic acid, sodium and potassium salts thereof, and combinations thereof. In some embodiments, an excipient having a —CHCOOH functional group is present in the dosage forms of the present invention in a concentration of about 0.1% to about 5% by weight of the dosage forms.

In some embodiments, the pharmaceutical dosage form of the present invention comprises a glidant to improve the flow properties of the mixture. Suitable glidants include silicas (such as SILOID® and SILOX®, and AEROSIL®), and talc.

In some embodiments, the concentration of excipients in the secondary vehicle can be selected to optimize the physical integrity of the dosage forms of the present invention. Not being bound by any particular theory, the durability and robustness of the compressed dosage forms of the present invention can be estimated using the compaction index of the excipients used to prepare the dosage forms. As used herein, "compaction index" refers to the force in kilopounds (kp) required to fracture a solid mass prepared by compaction of 500 mg of powder with 1000 lbs. to 5000 lbs. pressure using a $^{16}\!/_{32}$" die and flat face punches. Not being bound by any particular theory, the compaction index can be used as an indicator of particle interactions in a compressed solid dosage form. For example, the compression of a dry mixture usually has a significant effect on the inter-particle interactions within the mixture, and can involve combinations of: (i) closer contact between particles and the exclusion of air; (ii) alignment and interlocking of particles; (iii) the development of stresses and shearing forces that result in fracture and the generation of smaller particles; (iv) elastic and plastic deformations of particles that can change particle shape; and (v) chemical bonding between adjacent particles, especially during long-term storage.

As used herein, "administering to" refers to placing a pharmaceutical dosage form of the present invention in physical contact with the buccal cavity (i.e., the tongue, the buccal mucosa, the sublingual mucosa, etc.) of a subject in need thereof.

The oral transmucosal dosage form of the invention may be in any form that is suitable for oral transmucosal delivery. Examples of such dosage forms include a lozenge, lollipop, tablet or troche.

If the oral transmucosal dosage form is a lollipop, the lollipop may be prepared, and/or the handle attached, in accordance with methods disclosed in U.S. Publ. Nos. 2007/0107200 or 2006/0280792.

EXAMPLES

Example 1

An oral transmucosal dosage form comprising 7 mg of testosterone having the following composition as shown in Table 1 was prepared according to the process described in Table 1 and depicted in FIG. 1.

TABLE 1

| Item # | Ingredients | mg per dose |
|---|---|---|
| | Primary Vehicle with a Synergistic Ternary CIA system | |
| 1 | Testosterone, USP | 7 |
| 2 | Polyethylene Glycol 8000 | 80 |
| 3 | Hydrogenated Vegetable Oil | 20 |
| 4 | Lauroyl polyoxyl-32 glycerides | 100 |
| | Secondary Vehicle | |
| 5 | Sucrose | 805 |
| 6 | Sorbitol | 805 |
| 7 | Xanthan Gum | 180 |
| | Lubricant | |
| 8 | Magnesium Stearate, NF | 3 |
| | Total | 2000 |

In a jacketed high shear mixer, polyethylene glycol 8000, hydrogenated vegetable oil and lauroyl polyoxyl-32 glycerides were heated to about 80° C. and mixed to obtain a monophasic molten mass. The testosterone was added to the molten mass and allowed to dissolve. The molten mass was then cooled and solidified. The solidified mixture was milled through a Fitzmill. The milled granules of the primary vehicle were blended with the secondary vehicle of sucrose, sorbitol and xanthan gum, and then lubricated with magnesium stearate using a V-Blender. The final blend was compressed into a lozenge using 0.68" round flat tooling with a target weight of 2 g.

Figure 2:
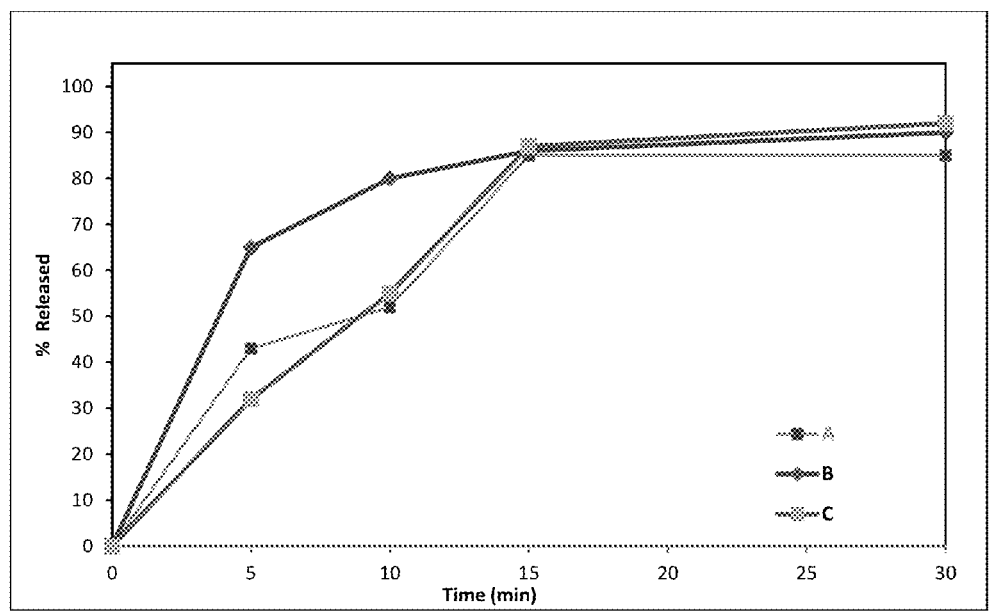
FIG. 2 depicts the dissolution profile of the oral transmucosal dosage form described in Example 1.

The dissolution of this oral transmucosal dosage form containing 7 mg of testosterone was tested using a Glass Bead Rotating Bottle Method described as follows. Two hundred (200) grams of 8 mm glass beads were added to a 450 mL cylindrical bottle with a plastic cap. The desired amount of dissolution media (90 mL, 150 mL or 250 mL of Simulated Saliva Fluid (SSF) (12 mM $KH_2PO_4$, 40 mM NaCl, 1.5 mM, NaOH to pH 6.2) was added to the glass bottle and equilibrated to 37±0.5° C. The lozenge was added to the bottle, and the bottle rotated at 18 rpm on a rotating bottle apparatus. Samples were withdrawn at 5, 10, 15, and 30 minutes and analyzed. Data generated beyond 30 minutes is not presented since the dosage form is designed to deliver the drug predominantly within 30 minutes. Furthermore, the drug release from most of the system reached steady state and avoidance of the additional data point do not have any impact on the outcome or conclusion from this study. The results of this analysis are as follows in Table 2, and are represented in graphic form in FIG. 2. As can be seen in Table 2, below, Curve A in FIG. 2 corresponds to dissolution over time in 90 mL of dissolution medium, Curve B corresponds to dissolution over time in 150 mL of dissolution medium, and Curve C corresponds to dissolution over time in 250 mL of dissolution medium.

TABLE 2

DISSOLUTION DATA
Percent Dissolved

| Time (min) | 90 mL Curve A | 150 mL Curve B | 250 mL Curve C |
|---|---|---|---|
| 0 | 0 | 0 | 0 |
| 5 | 43 | 65 | 32 |
| 10 | 52 | 80 | 55 |
| 15 | 85 | 86 | 87 |
| 30 | 85 | 90 | 92 |

Example 2

An oral transmucosal dosage form comprising 7 mg of testosterone having the following composition as shown in Table 3 was prepared according to the process described in Table 3.

TABLE 3

| Item # | Ingredients | mg per dose |
|---|---|---|
| | Primary Vehicle with one CIA | |
| 1 | Testosterone, USP | 7 |
| 2 | Polyethylene Glycol 8000 | 80 |
| | Secondary Vehicle | |
| 3 | Sucrose | 860 |
| 4 | Sorbitol | 860 |
| 5 | Xanthan Gum | 190 |
| | LUBRICANT | |
| 6 | Magnesium Stearate, NF | 3 |
| | Total | 2000 |

In a jacketed high shear mixer, polyethylene glycol 8000 was heated to about 80° C. to obtain a molten form. The testosterone was added to the molten mass and allowed to dissolve with mixing. The melt dispersion was then cooled and solidified. The solidified mixture was milled through a Fitzmill. The milled granules of the primary vehicle were blended with the secondary vehicle of sucrose, sorbitol and xanthan gum, and then lubricated with magnesium stearate using a V-Blender. The final blend was compressed into a lozenge using 0.68" round flat tooling with a target weight of 2 g.

Figure 3:
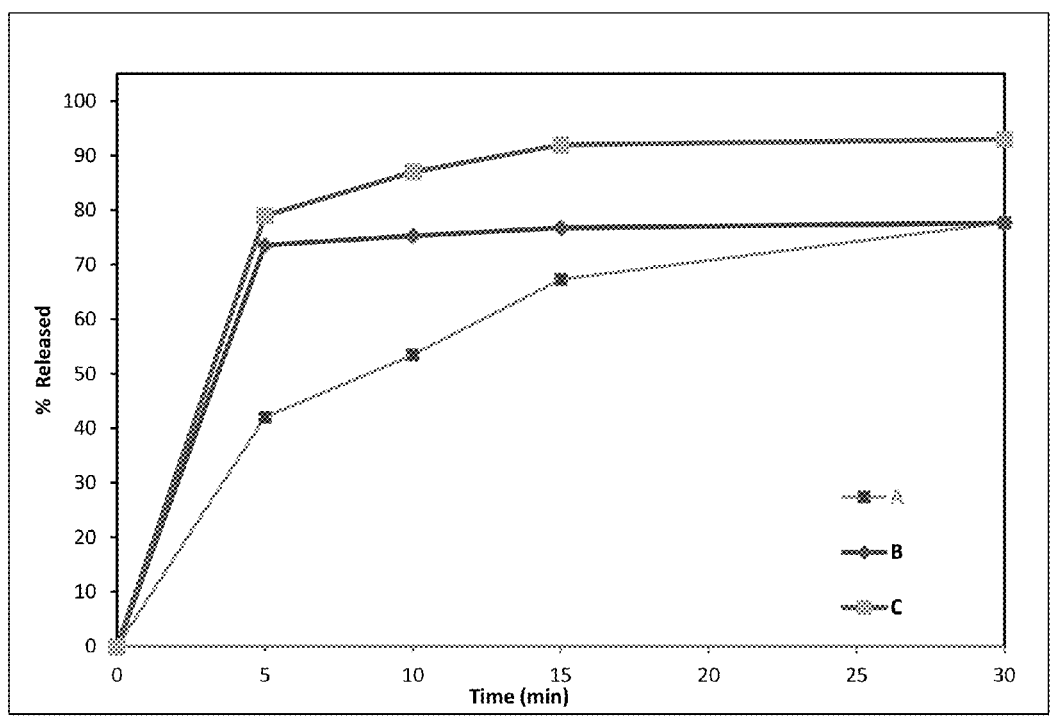
FIG. 3 depicts the dissolution profile of the oral transmucosal dosage form described in Example 2.

The dissolution of this oral transmucosal dosage form containing 7 mg of testosterone was tested using the Glass Bead Rotating Bottle Method, as described above. The results of this analysis are as follows in Table 4. The release profiles have been depicted in FIG. 3.

TABLE 4

| | DISSOLUTION DATA<br>Percent Dissolved | | |
|---|---|---|---|
| Time<br>(min) | 90 mL<br>Curve A | 150 mL<br>Curve B | 250 mL<br>Curve C |
| 0 | 0 | 0 | 0 |
| 5 | 42 | 74 | 79 |
| 10 | 53 | 75 | 87 |
| 15 | 67 | 77 | 92 |
| 30 | 78 | 78 | 93 |

Example 3

Figure 4:
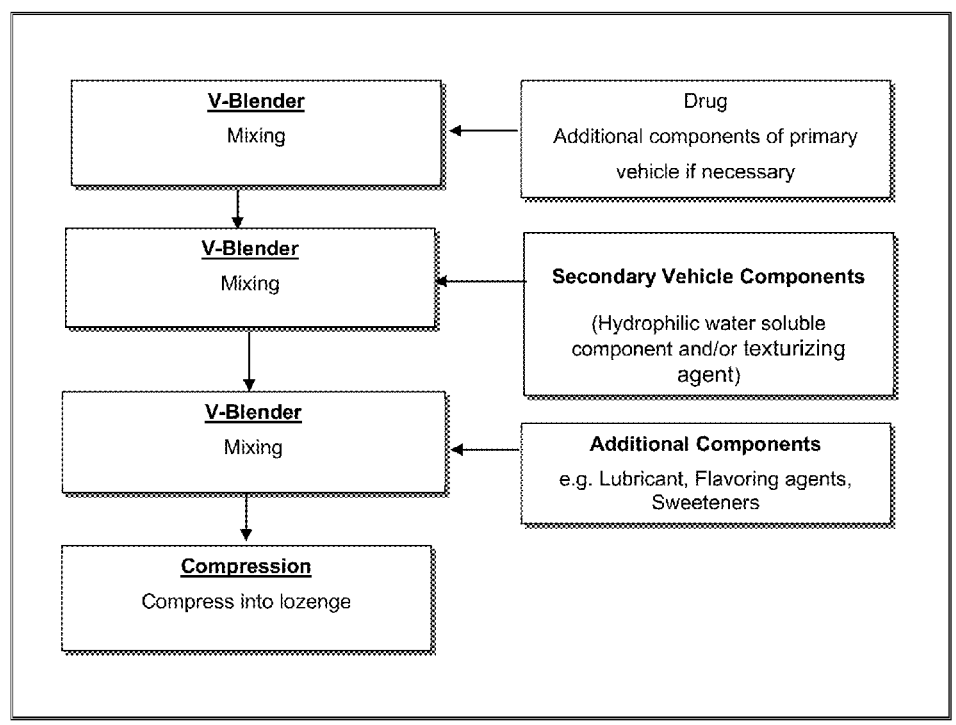
FIG. 4 depicts a manufacturing process flow chart for the oral transmucosal dosage form using physical mixtures.

A conventional dosage form comprising 7 mg of testosterone having the following composition was prepared according to the process described in FIG. 4. This composition as described in Table 3, lacks a CIA, was prepared for drug release comparison with embodiments of the oral transmucosal dosage forms of the invention, which contain one or more CIAs.

TABLE 5

| S. No | Ingredients | mg per Dose |
|---|---|---|
| | BLENDING | |
| 1 | Testosterone, USP | 7 |
| 2 | Sucrose | 895 |
| 3 | Sorbitol | 895 |
| 4 | Xanthan Gum | 200 |
| | LUBRICANT | |
| 5 | Magnesium Stearate, NF | 3 |
| | Total | 2000 |

In a V-blender, testosterone was blended with sucrose, sorbitol and xanthan gum, and then lubricated with magnesium stearate. The final blend was compressed into a lozenge using 0.68" round flat tooling with a target weight of 2 g.

Figure 5:
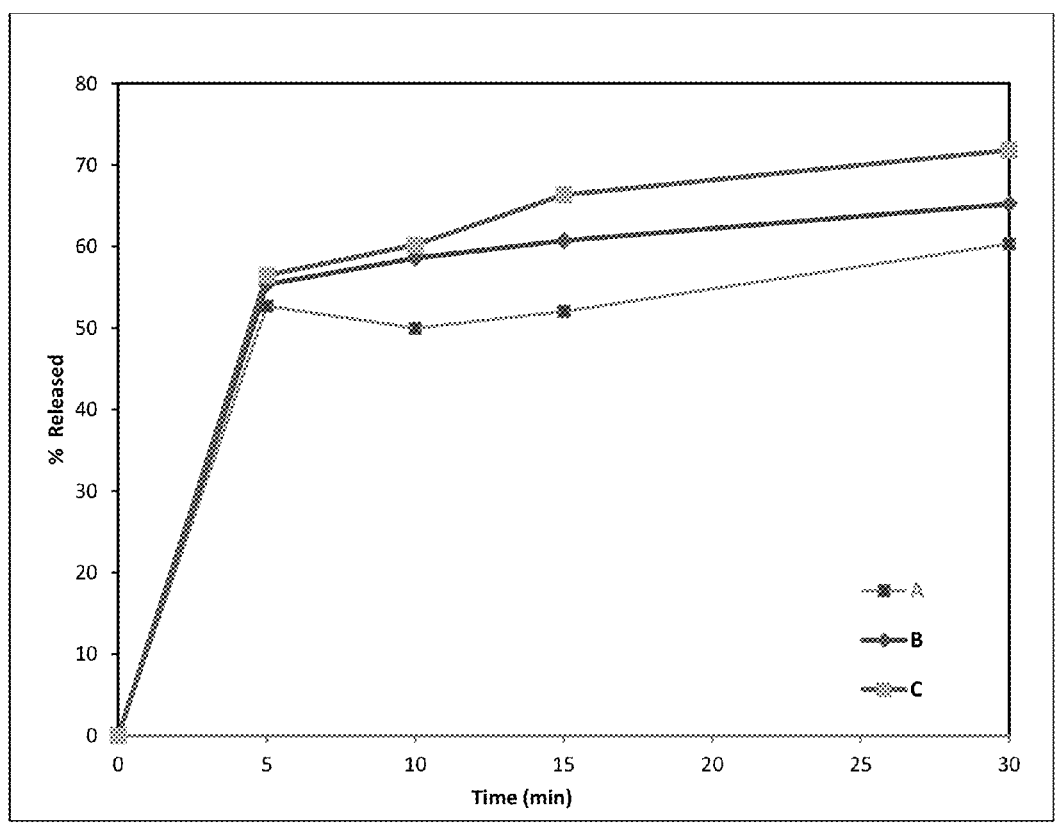
FIG. 5 depicts the dissolution profile of the oral transmucosal dosage form described in Example 3.

The dissolution data of this oral transmucosal dosage form containing 7 mg of testosterone was tested using the Glass Bead Rotating Bottle Method, as described above. The results of this analysis are as follows in Table 6. The release profiles are shown in FIG. 5.

TABLE 6

| | DISSOLUTION DATA<br>Percent Dissolved | | |
|---|---|---|---|
| Time<br>(min) | 90 mL<br>Curve A | 150 mL<br>Curve B | 250 mL<br>Curve C |
| 0 | 0 | 0 | 0 |
| 5 | 53 | 55 | 57 |
| 10 | 50 | 59 | 60 |
| 15 | 52 | 61 | 66 |
| 30 | 60 | 65 | 72 |

Example 4

A conventional dosage form comprising 7 mg of testosterone having the following composition was prepared according to the process described below. This composition, which has a non-CIA of talc, was prepared for dissolution comparison with embodiments of the oral transmucosal dosage forms of the invention, which contain one or more CIAs. So the talc was treated in the same manner as a CIA during processing.

TABLE 7

| Ingredients | Mg Per Dose |
|---|---|
| Primary Vehicle with a Non-CIA | |
| Testosterone, USP | 7 |
| Talc | 200 |
| Secondary Vehicle | |
| Sucrose | 805 |
| Sorbitol | 805 |
| Xanthan Gum | 180 |
| Lubricant | |
| Magnesium Stearate, NF | 3 |
| Total | 2000 |

In a jacketed high shear mixer, talc was heated to about 80° C. and mixed to obtain a homogenous heated mass. Testosterone was added to the heated mass and mixed. The homogenous mixture was cooled and blended with the secondary vehicle of sucrose, sorbitol and xanthan gum. The blend was lubricated with magnesium stearate using a V-Blender and the final blend was compressed into a lozenge using 0.68" round flat tooling with a target weight of 2 g.

Figure 6:
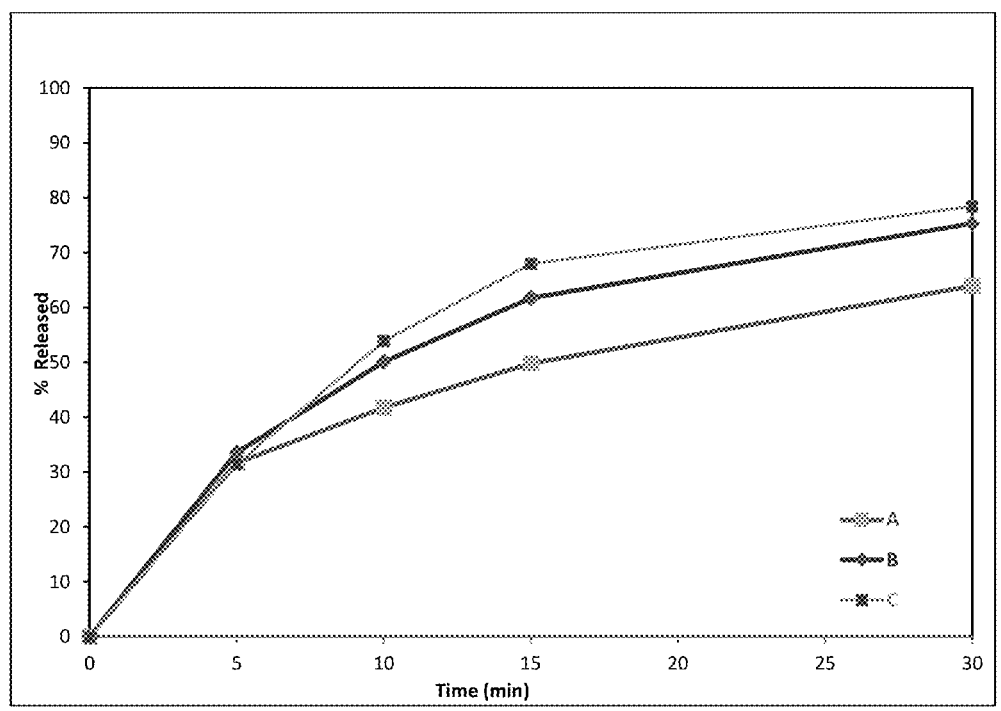
FIG. 6 depicts the dissolution profile of the oral transmucosal dosage form described in Example 4.

The dissolution of this oral transmucosal dosage form containing 7 mg of testosterone was tested using the Glass Bead Rotating Bottle Method, as described above. The results of this analysis are as follows in Table 8. They are shown in graphic form in FIG. 6.

TABLE 8

| | DISSOLUTION DATA<br>Percent Dissolved | | |
|---|---|---|---|
| Time<br>(min) | 90 mL<br>Curve A | 150 mL<br>Curve B | 250 mL<br>Curve C |
| 0 | 0 | 0 | 0 |
| 5 | 32 | 34 | 31 |
| 10 | 42 | 50 | 54 |
| 15 | 50 | 62 | 68 |
| 30 | 64 | 75 | 78 |

Example 5

A conventional dosage form comprising 7 mg of testosterone having the following composition was prepared according to the process described in FIG. 4. This composition, which contains a primary vehicle of three CIAs, was prepared by a dry mix technique that does not produce a solid solution of the drug in the primary vehicle, to provide analytical comparison with embodiments of the oral transmucosal dosage forms of the invention that were prepared using a technique that dissolves the drug in the primary vehicle CIAs.

TABLE 9

| S. No | Ingredients | mg per Dose |
|---|---|---|
| | Blending with Primary Vehicle without melting | |
| 1 | Testosterone, USP | 7 |
| 2 | Polyethylene Glycol 8000 | 80 |

TABLE 9-continued

| S. No | Ingredients | mg per Dose |
|---|---|---|
| 3 | Hydrogenated Vegetable Oil | 20 |
| 4 | Lauroyl polyoxyl-32 glycerides | 100 |
| | Blending with Secondary Vehicle | |
| 5 | Sucrose | 805 |
| 6 | Sorbitol | 805 |
| 7 | Xanthan Gum | 180 |
| | LUBRICANT | |
| 8 | Magnesium Stearate, NF | 3 |
| | Total | 2000 |

In a V-blender, testosterone was blended with the primary vehicle components, polyethylene glycol 8000, hydrogenated vegetable oil, and lauroyl polyoxyl-32 glycerides, and further blended with the secondary vehicle components, sucrose, sorbitol and xanthan gum, and then lubricated with magnesium stearate. The final blend was compressed into a lozenge using 0.68" round flat tooling with a target weight of 2 g.

Figure 7:
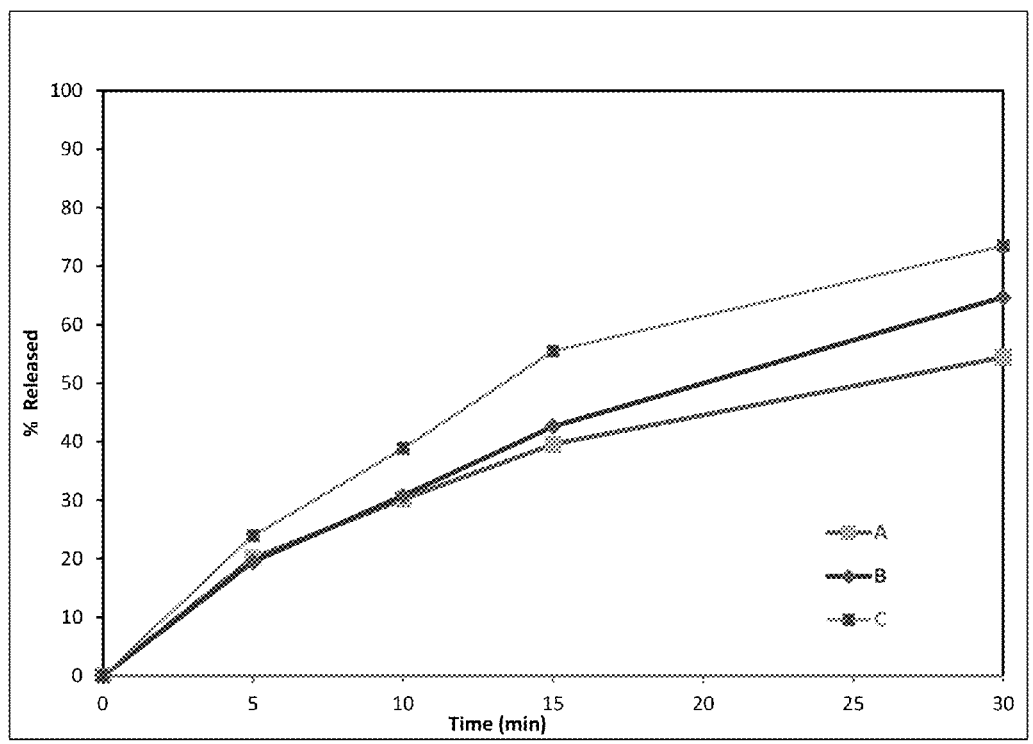
FIG. 7 depicts the dissolution profile of the oral transmucosal dosage form described in Example 5.

The dissolution of this oral transmucosal dosage form containing 7 mg of testosterone was tested using the Glass Bead Rotating Bottle Method, as described above. The results of this analysis are as follows in Table 10. They are shown in graphic form in FIG. 7.

TABLE 10

DISSOLUTION DATA
Percent Dissolved

| Time (min) | 90 mL Curve A | 150 mL Curve B | 250 mL Curve C |
|---|---|---|---|
| 0 | 0 | 0 | 0 |
| 5 | 20 | 19 | 24 |
| 10 | 30 | 31 | 39 |
| 15 | 40 | 43 | 55 |
| 30 | 54 | 65 | 74 |

Discussion of Results from Examples 1-5

The crystallinity of the active ingredient, testosterone, in the dosage forms prepared in Examples 1-5 was analyzed by evaluating the effect of volume of dissolution media on the dissolution rate of the dosage forms. Due to the low solubility of crystalline testosterone (~0.027 mg/mL in water at 37° C.), the release of crystalline testosterone is dependent on the volume of dissolution media. The higher the medium volume is, the higher the release of the drug observed.

Figure 8:
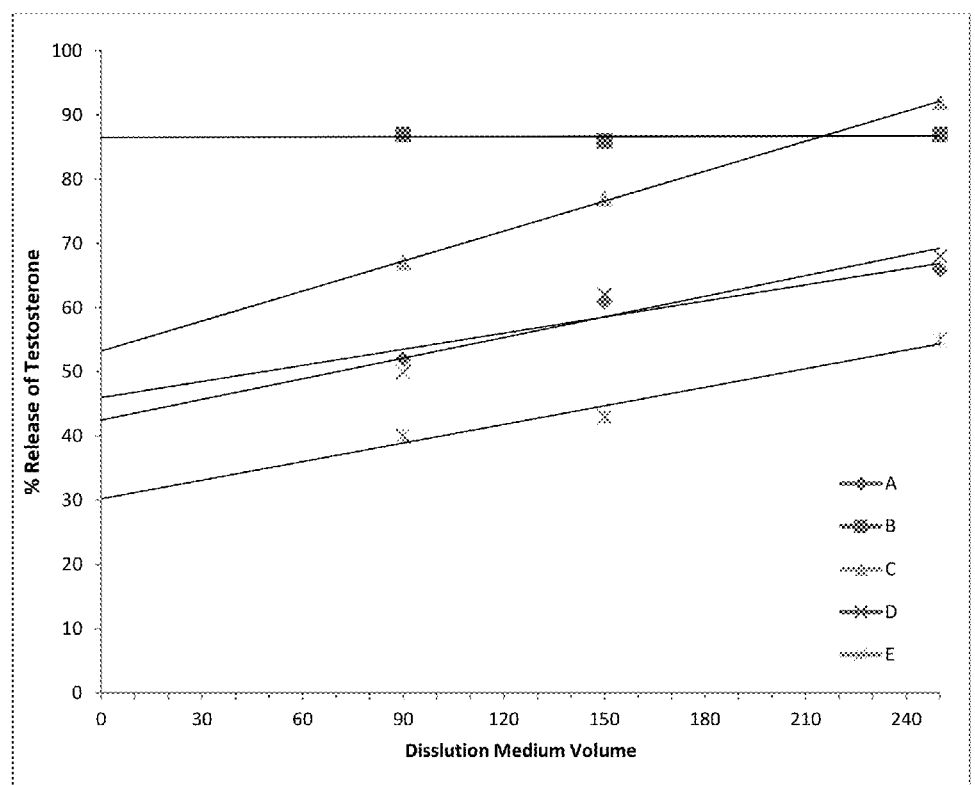
FIG. 8 depicts a graph showing the impact of dissolution medium volume on percentage of testosterone release at 15 minutes from testosterone oral transmucosal dosage forms.

The conventional dosage forms with no CIA (Example 3 and Example 4), or which contain a CIA but are prepared by dry mixing, which does not produce a monophasic primary vehicle (Example 5), contain crystalline testosterone and therefore show significant volume dependent release patterns, as seen in FIG. 8. Line A corresponds to Example 3, line B corresponds to Example 1, line C corresponds to Example 2, line D corresponds to Example 4 and line E corresponds to Example 5. These batches exhibit higher release in 250 ml of dissolution medium, and release drops as the volume of dissolution media decreases. The oral transmucosal dosage form with only a single CIA (Example 2) although exhibits a volume dependent release behavior, however the percent drug release of the single CIA system is much higher than that of the conventional dosage forms with no CIA (Examples 3 and 4) or that prepared by dry mix (Example 5) e.g. drug release from CIA formulation in 90 ml is higher than that from the crystalline formulation in 240 ml.

The result indicates a release rate of testosterone is faster for a molten single CIA system, as compared to drug release from the crystalline API in the conventional systems lacking a CIA. Moreover, the oral transmucosal dosage form of a molten monophasic combination CIA system comprising three CIA's, hydrophilic, lipophilic and amphiphilic, (Example 1) releases higher amount of drug than conventional systems lacking a CIA, and exhibits a release rate independent of the volume of dissolution media. This confirms that the drug testosterone in this dosage form (Example 1) has significantly reduced bonds between the drug molecules or reduced crystallinity, and is readily available for being solubilized and absorbed. The combination of three CIA's in a monophasic primary vehicle in Example 1 provides the highest percentage of release in the smallest dissolution volume, confirming the synergistic effect of the three CIAs on the dissolution rate of testosterone.

The crystallinity of the drug in the dosage form of Example 1 was analyzed by performing x-ray powder diffraction on a sample of testosterone in primary vehicle prepared according to Example 1. Samples of crystalline testosterone, and of the individual components of the primary vehicle, PEG-8000, hydrogenated vegetable oil and lauroyl polyoxyl-32 glycerides were also analyzed for comparison.

Approximately 50-100 mg of each sample was examined by X-ray powder diffractometry. XRPD analysis was performed using a Rigaku Mini Flex II X-ray diffractometer. The samples were scanned from 5-45° $2\theta$ using a scan rate of 1° $2\theta$/min and Cu target ($\lambda$=1.54 Angstroms). Equipment performance was checked using a NIST traceable Mica standard for peak position.

Figure 9:
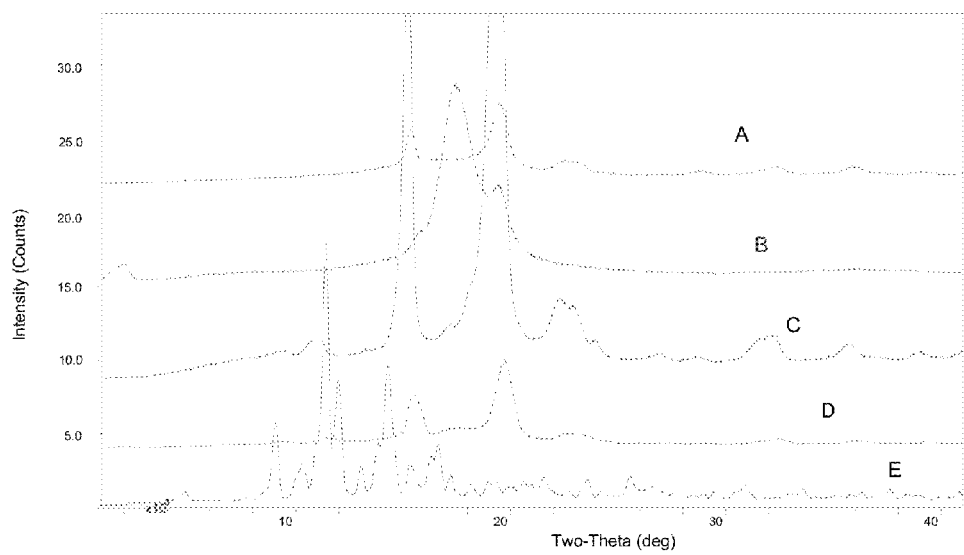
FIG. 9 depicts a chart showing x-ray diffractograms for samples of testosterone alone, and in primary vehicle prepared according to Example 1, and other primary vehicles.

The results of the analysis are shown in FIG. 9. In this figure, the curve marked with the letter "A" corresponds to lauroyl polyoxyl-32 glycerides. The curve marked with the letter "B" corresponds to hydrogenated vegetable oil. The curve marked with the letter "C" corresponds to polyethylene glycol 8000. The curve marked with the letter "D" corresponds to testosterone in a synergistic CIA system of lauroyl polyoxyl-32 glycerides, hydrogenated vegetable oil and polyethylene glycol 8000. The curve marked with the letter "E" corresponds to testosterone.

As evident from the XRPD diffractogram, testosterone is crystalline with well-defined peaks (FIG. 9, curve E). Curve D, which corresponds to testosterone in a synergistic CIA system of lauroyl polyoxyl-32 glycerides, hydrogenated vegetable oil and polyethylene glycol 8000, shows significantly decreased intensity of diffraction peaks, indicating the complete loss of crystallinity of the testosterone in the synergistic CIA system.

The ability of a CIA to reduce or eliminate the dependence of dissolution rate on dissolution media volume can also be significant because the dosage form of the invention is designed to be held in the mouth while releasing drug. The mouth contains a relatively small volume of saliva (dissolution medium), and this volume and the rate of production may vary in different people and under different conditions. Thus a dosage form that can provide improved dissolution and drug release that is independent of dissolution medium (saliva) volume, or that has reduced dependence on volume would be beneficial as it could provide a more consistent drug release rate from patient to patient and from dosing to dosing.

Example 6

An oral transmucosal dosage form comprising 0.5 mg of 17β-estradiol hemihydrate and three CIAs, having the following composition was prepared according to the process described below, as depicted in FIG. 1.

TABLE 11

| Item # | Ingredients | mg per dose |
|---|---|---|
| | Primary Vehicle with three CIAs | |
| 1 | 17β-Estradiol Hemihydrate | 0.5 |
| 2 | Polyethylene Glycol 8000 | 80 |
| 3 | Hydrogenated Vegetable Oil | 20 |
| 4 | Lauroyl polyoxyl-32 glycerides | 100 |
| | Secondary Vehicle | |
| 5 | Sucrose | 810 |
| 6 | Sorbitol | 810 |
| 7 | Xanthan Gum | 180 |
| | Lubricant | |
| 8 | Magnesium Stearate, NF | 3 |
| | Total | 2000 |

In a jacketed high shear mixer, polyethylene glycol 8000, hydrogenated vegetable oil and lauroyl polyoxyl-32 glycerides were heated to about 80° C. and mixed to obtain a monophasic molten mass. The 17β-estradiol hemihydrate was added to the molten mass and allowed to dissolve. The molten mass was then cooled and solidified. The solidified mixture was milled through a Fitzmill. The milled granules of the primary vehicle were blended with the secondary vehicle of sucrose, sorbitol and xanthan gum, and then lubricated with magnesium stearate using a V-Blender. The final blend was compressed into a lozenge using 0.68" round flat tooling with a target weight of 2 g.

Figure 10:
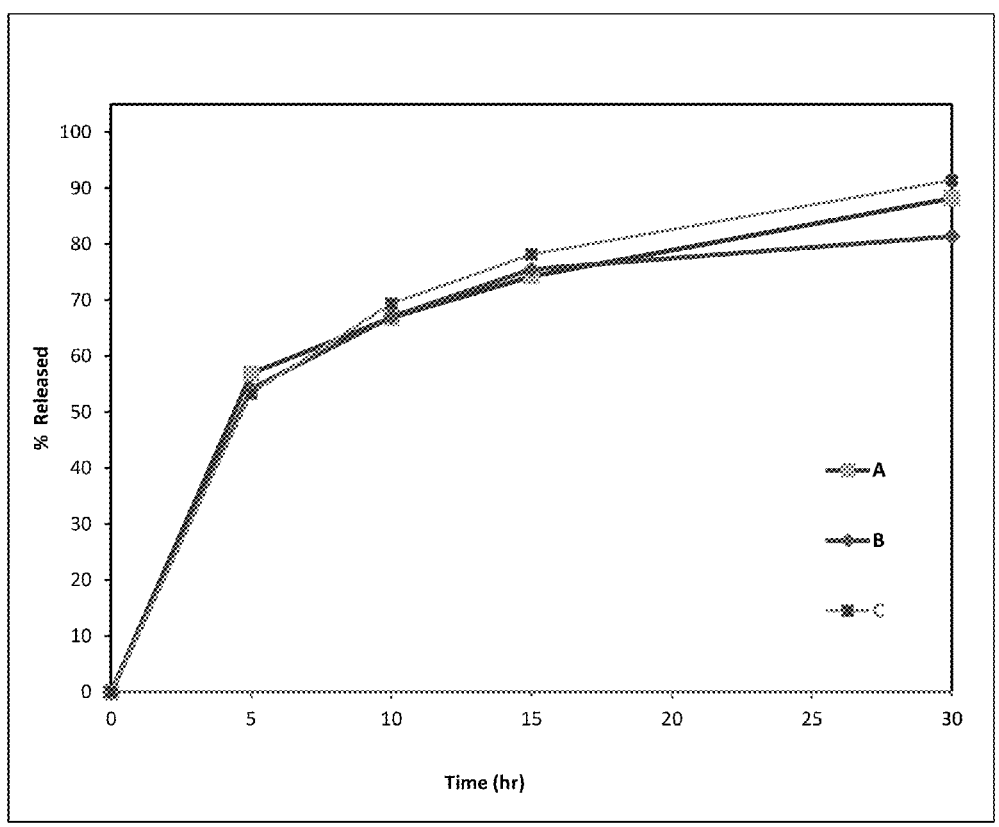
FIG. 10 depicts the dissolution profile of the oral transmucosal dosage form described in Example 6.

The dissolution of this oral transmucosal dosage form containing 0.5 mg of 17β-estradiol hemihydrate was tested using the Glass Bead. The results of this analysis are as follows in Table 12. They are shown in graphic form in FIG. 10.

TABLE 12

DISSOLUTION DATA
Percent Dissolved

| Time (min) | 90 mL Curve A | 150 mL Curve B | 250 mL Curve C |
|---|---|---|---|
| 0 | 0 | 0 | 0 |
| 5 | 57 | 54 | 53 |
| 10 | 67 | 67 | 69 |
| 15 | 74 | 76 | 78 |
| 30 | 88 | 81 | 91 |

Example 7

An oral transmucosal dosage form comprising 0.5 mg of 17β-estradiol hemihydrate and a single CIA, having the following composition was prepared according to the process described below.

TABLE 13

| Item # | Ingredients | mg per dose |
|---|---|---|
| | Primary Vehicle with one CIA | |
| 1 | 17β-Estradiol Hemihydrate | 0.5 |
| 2 | Polyethylene Glycol 8000 | 80 |
| | Secondary Vehicle | |
| 5 | Sucrose | 858.5 |
| 6 | Sorbitol | 859 |
| 7 | Xanthan Gum | 199 |
| | Lubricant | |
| 8 | Magnesium Stearate, NF | 3 |
| | Total | 2000 |

In a jacketed high shear mixer, polyethylene glycol 8000 was heated to about 80° C. to obtain a molten form. The 17β-estradiol hemihydrate was dissolved in the molten mass through mixing. The molten dispersion was then cooled and solidified. The solidified mixture was milled through a Fitzmill. The milled granules of the primary vehicle were blended with the secondary vehicle of sucrose, sorbitol and xanthan gum, and then lubricated with magnesium stearate using a V-Blender. The final blend was compressed into a lozenge using 0.68" round flat tooling with a target weight of 2 g.

Figure 11:
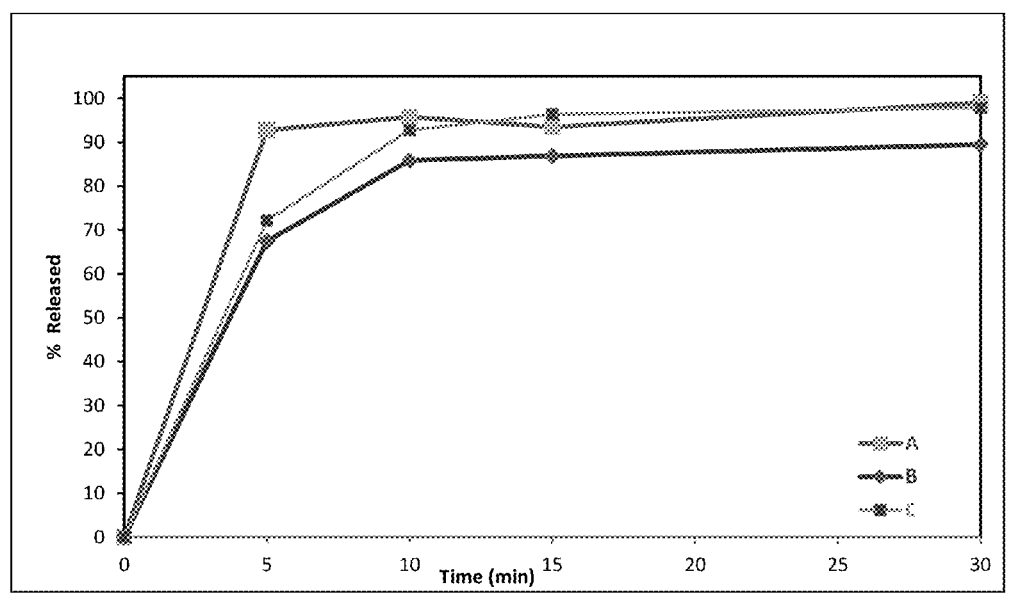
FIG. 11 depicts the dissolution profile of the oral transmucosal dosage form described in Example 7.

The dissolution of this oral transmucosal dosage form containing 17β-estradiol hemihydrate was tested using the Glass Bead Rotating Bottle Method, as described earlier. The results of this analysis are as follows in Table 14. They are shown in graphic form in FIG. 11.

TABLE 14

DISSOLUTION DATA
Percent Dissolved

| Time (min) | 90 mL Curve A | 150 mL Curve B | 250 mL Curve C |
|---|---|---|---|
| 0 | 0 | 0 | 0 |
| 5 | 93 | 67 | 72 |
| 10 | 96 | 86 | 93 |
| 15 | 94 | 87 | 96 |
| 30 | 99 | 90 | 98 |

Example 8

A conventional dosage form comprising 0.5 mg of 17β-estradiol hemihydrate having the following composition as shown in Table 15 was prepared according to the process described below, as depicted in FIG. 4. This composition, which lacks a CIA, was prepared for drug release comparison with embodiments of the oral transmucosal dosage forms of the invention, which contain one or more CIAs.

TABLE 15

| Item # | Ingredients | mg per dose |
|---|---|---|
| | Blending | |
| 1 | 17β-Estradiol Hemihydrate | 0.5 |
| 2 | Sucrose | 896.5 |
| 3 | Sorbitol | 900 |
| 4 | Xanthan Gum | 200 |

TABLE 15-continued

| Item # | Ingredients | mg per dose |
|---|---|---|
| | Lubricant | |
| 5 | Magnesium Stearate, NF | 3 |
| | Total | 2000 |

In a V-blender, 17β-estradiol hemihydrate was blended with sucrose, sorbitol and xanthan gum, and then lubricated with magnesium stearate. The final blend was compressed into a lozenge using 0.68" round flat tooling with a target weight of 2 g.

Figure 12:
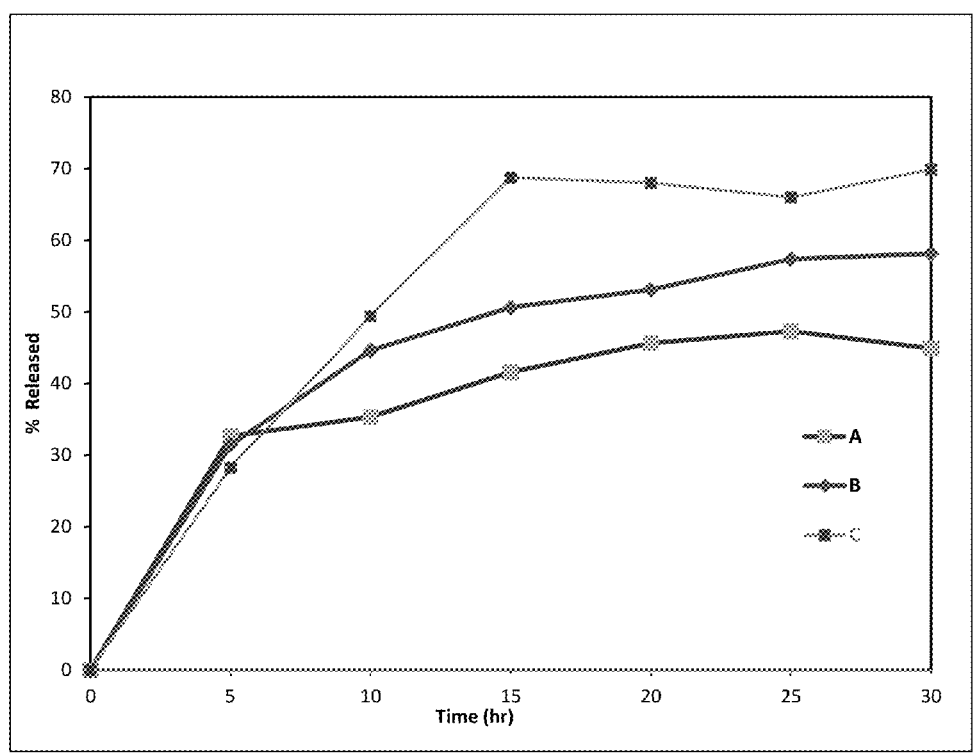
FIG. 12 depicts the dissolution profile of the oral transmucosal dosage form described in Example 8.

The dissolution of this oral transmucosal dosage form containing 0.5 mg of 17β-estradiol hemihydrate was tested using the Glass Bead Rotating Bottle Method, as described earlier. The results of this analysis are as follows in Table 16. They are shown in graphic form in FIG. 12.

TABLE 16

DISSOLUTION DATA
Percent Dissolved

| Time (min) | 90 mL Curve A | 150 mL Curve B | 250 mL Curve C |
|---|---|---|---|
| 0 | 0 | 0 | 0 |
| 5 | 33 | 31 | 28 |
| 10 | 35 | 45 | 49 |
| 15 | 42 | 51 | 69 |
| 20 | 46 | 53 | 68 |
| 25 | 47 | 57 | 66 |
| 30 | 45 | 58 | 70 |

Discussion of Results from Examples 6-8

The crystallinity of estradiol hemihydrate in the primary vehicle of Example 7, PEG-8000, was analyzed by performing x-ray powder diffraction on a sample of estradiol hemihydrate in primary vehicle prepared according to Example 7. Approximately 50-100 mg of the milled primary vehicle containing estradiol hemihydrate was examined by X-ray powder diffractometry. XRPD analysis was performed using a Rigaku Mini Flex II X-ray diffractometer. The samples were scanned from 5-45° 2θ using a scan rate of 1° 2θ/min and Cu target ($\lambda$=1.54 Angstroms). Equipment performance was checked using a NIST traceable Mica standard for peak position.

Figure 13:
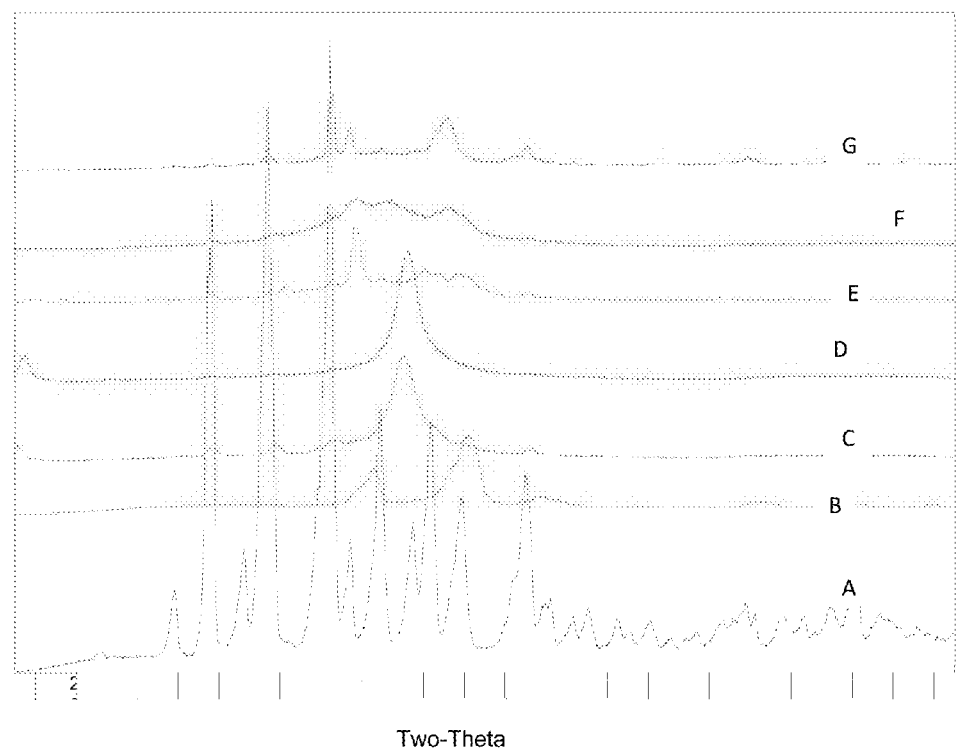
FIG. 13 depicts chart showing x-ray diffractograms for samples of estradiol alone, and in primary vehicle prepared according to Example 7, and other primary vehicles.

The crystallinity of estradiol hemihydrate alone, or in various other single CIA systems at a weight ratio of estradiol hemihydrate to CIA of 10 to 90, was also analyzed similarly by performing x-ray powder diffraction with a Rigaku Mini Flex II X-ray diffractometer. These other single CIA systems were lauroyl polyoxyl-32 glycerides, lauroyl macrogol-6 glycerides, cocoa butter, hydrogenated vegetable oil, and sucrose esters. The results of the analysis are shown in FIG. 13, in which A corresponds to estradiol hemihydrate alone, B corresponds to estradiol hemihydrate with polyethylene glycol 8000, C corresponds to estradiol hemihydrate with sucrose esters, D corresponds to estradiol hemihydrate with hydrogenated vegetable oil, E corresponds to estradiol hemihydrate with cocoa butter, F corresponds to estradiol hemihydrate with lauroyl macrogol-6 glycerides and G corresponds to estradiol hemihydrate with lauroyl polyoxyl-32 glycerides. As evident from the XRPD diffractogram, estradiol hemihydrate is crystalline with well-defined peaks (FIG. 13, curve A). Curves B to G, which corresponds to estradiol hemihydrate in a single CIA system, show significantly decreased intensity of diffraction peaks, indicating completely or substantially reduced crystal bonds between the molecules or reduced crystallinity of estradiol hemihydrate in these single CIA systems.

Due to the low solubility of crystalline 17β-estradiol hemihydrate (~2.2 μg/mL in water at 37° C.), the release of crystalline 17β-estradiol hemihydrate is dependent on the volume of dissolution media. The higher the dissolution medium volume is, the higher the amount of drug released.

Figure 14:
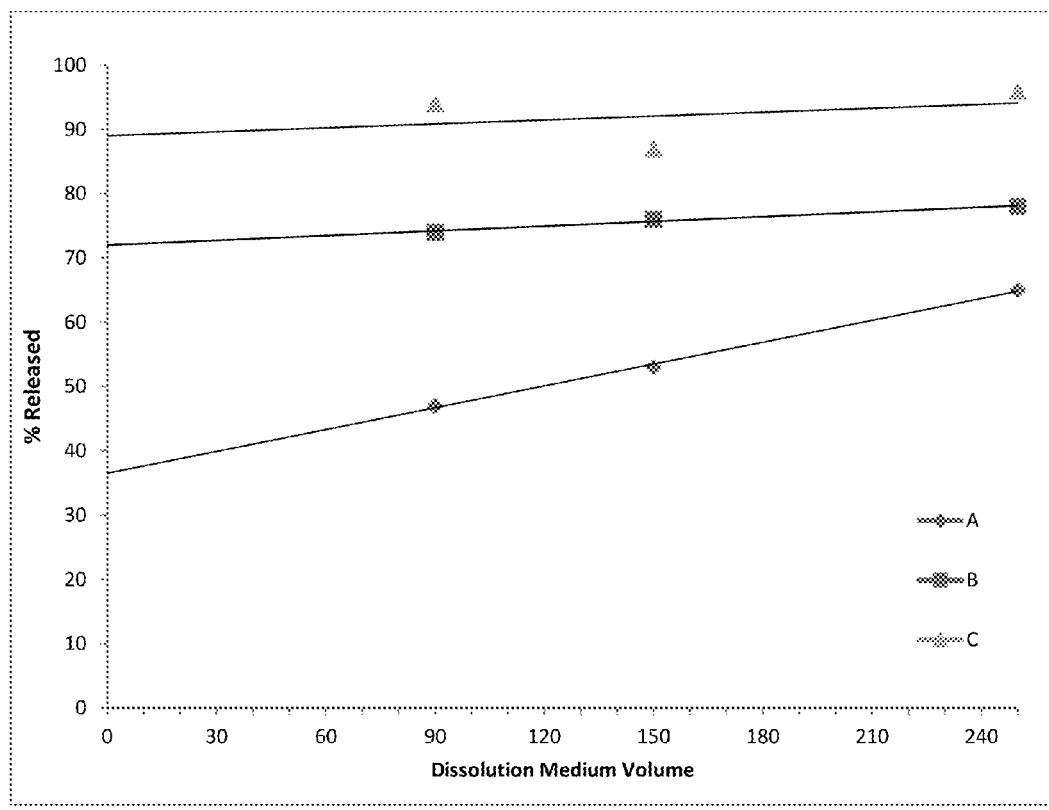
FIG. 14 depicts a graph showing the impact of dissolution medium volume on percentage of estradiol hemihydrate release at 15 minutes from estradiol hemihydrate oral transmucosal dosage forms.

A conventional dosage form having no primary vehicle or CIA (Example 8) contains crystalline 17β-estradiol hemihydrate shows significant volume dependent release patterns. This oral dosage form exhibits higher release in 250 ml and release drops as the volume of dissolution media decreases. In contrast, both the oral transmucosal dosage forms with three CIAs (hydrophilic, lipophilic and amphiphilic) (Example 6) and a single CIA (Example 7), release more drug, and exhibit a release rate independent of the volume of dissolution media. These results, are shown in FIG. 14, in which Line A corresponds to Example 8, line B corresponds to Example 6 and line C corresponds to Example. These results support the conclusion that the drug 17β-estradiol hemihydrate in these dosage forms (Examples 7) has the significantly or substantially reduced crystal bonds between molecules or reduced crystallinity, and is readily available for release. The lower drug release of Example 6 as compared to Example 7 is probably due to the slow dissolution of the lipophilic and amphiphilic CIAs in Example 6 as compared to the fast release of the hydrophilic CIA in Example 7.

Example 9

Evaluation of Decrystallization Ability of CIA Systems and Development of a Mathematic Model for Reduced Drug Crystallinity Assessment The heat of fusion ($\Delta H_f$) can be measured via Differential Scanning calorimetry (DSC). As measured using a DSC Q2000 from TA Instruments (New Castle, Del.), the crystalline testosterone has a $\Delta H_f$ value of about 102.4 J/g at its melting point of about 150° C. This data indicates that theoretical heat of fusion of a 100% crystalline testosterone is about 102.4 J/g.

To evaluate the ability of various single or combination CIA systems on testosterone, the heat of fusion ($\Delta H_f$) of testosterone was measured at about 150° C. for each molten sample of testosterone and CIA system using DSC. As a control, the heat of fusion ($\Delta H_f$) of testosterone was also measured for the heat treated (about 80° C.) sample of testosterone and a non-CIA of talc. Talc is an inert purified hydrated magnesium silicate with a melting point of 1500° C. The CIA systems evaluated include single agent systems such as polyethylene glycol 8000, Vitamin-E TPGS, lauroyl polyoxyl-32 glycerides, and hydrogenated vegetable oil, a binary CIA system of, by weight, 50% polyethylene glycol 8000 and 50% Vitamin-E TPGS, and a ternary CIA system of, by weight, 40% polyethylene glycol (PEG) 8000, 50% lauroyl polyoxyl 32 glycerides, and 10% hydrogenated vegetable oil. All single and combination CIA systems evaluated have melting points different from the melting point of testosterone, and all their melting points are below 100° C.

Figure 15:
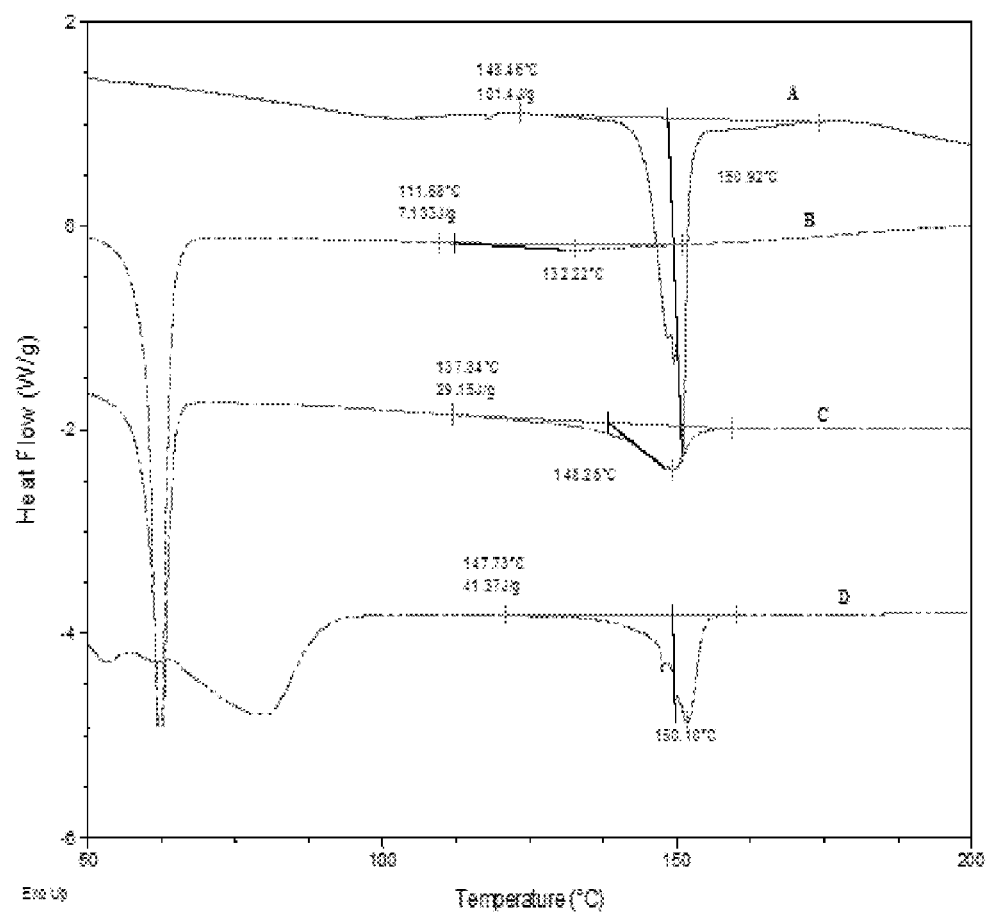
FIG. 15 depicts the DSC thermograms for different ratios of testosterone-PEG 8000 CIA systems.
Figure 16:
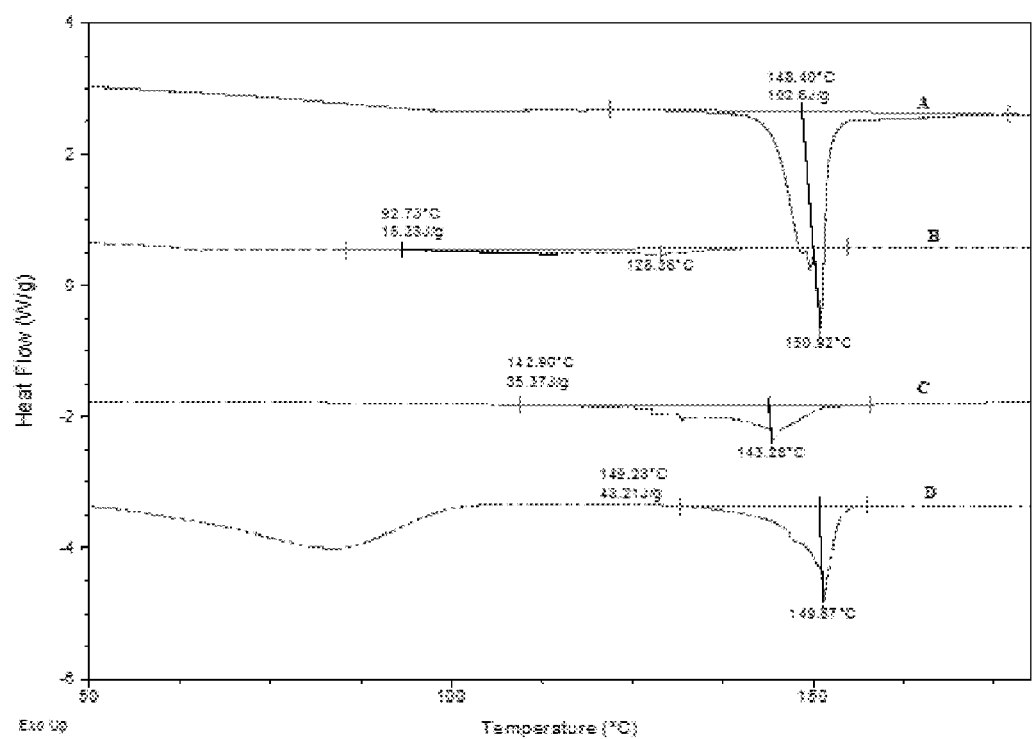
FIG. 16 depicts the DSC thermograms for different ratios of testosterone-vitamin E-TPGS CIA systems.
Figure 17:
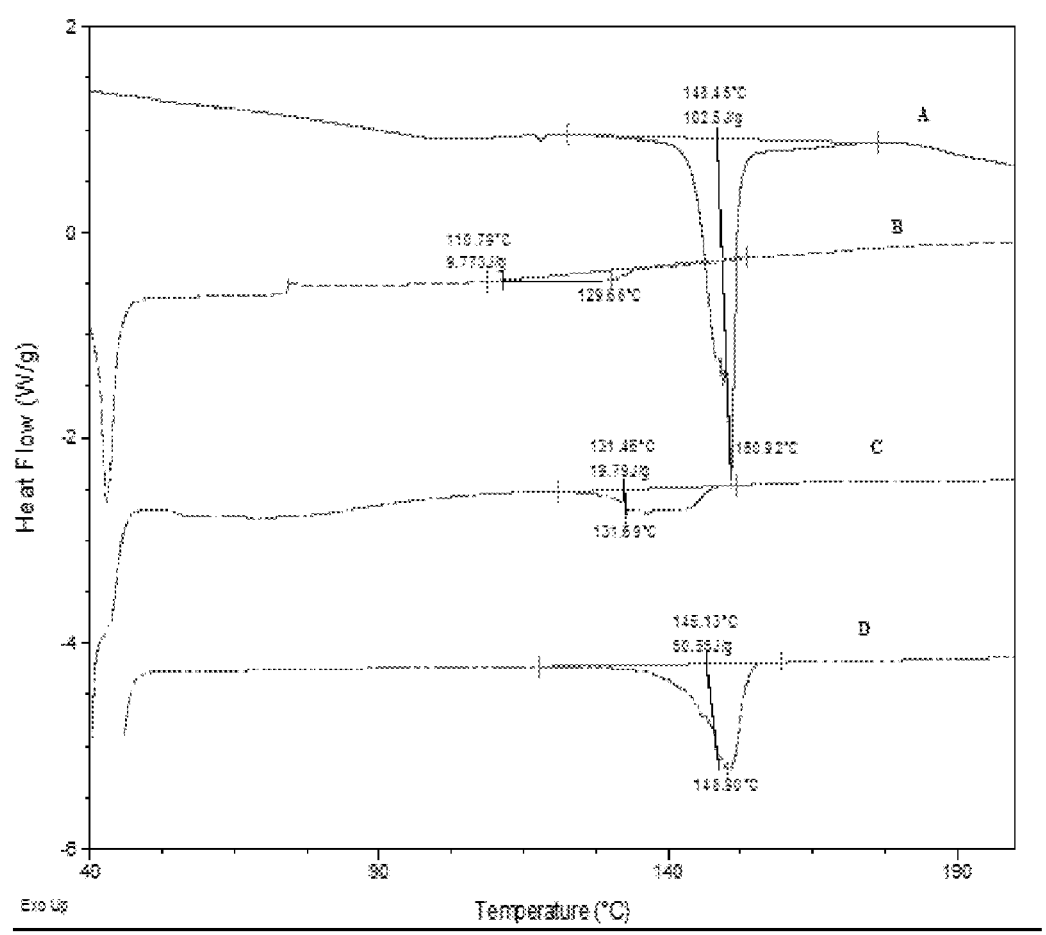
FIG. 17 depicts the DSC thermograms for different ratios of testosterone-lauroyl polyoxyl-32 glycerides CIA systems
Figure 18:
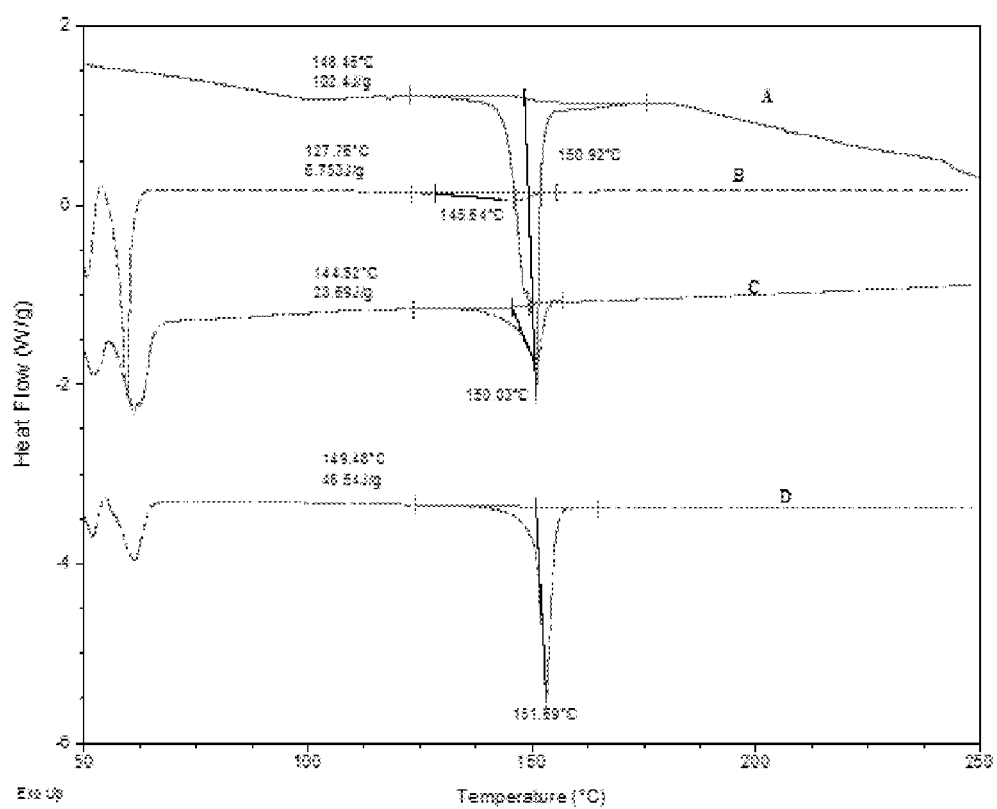
FIG. 18 depicts the DSC thermograms for testosterone-hydrogenated vegetable oil CIA systems.
Figure 19:
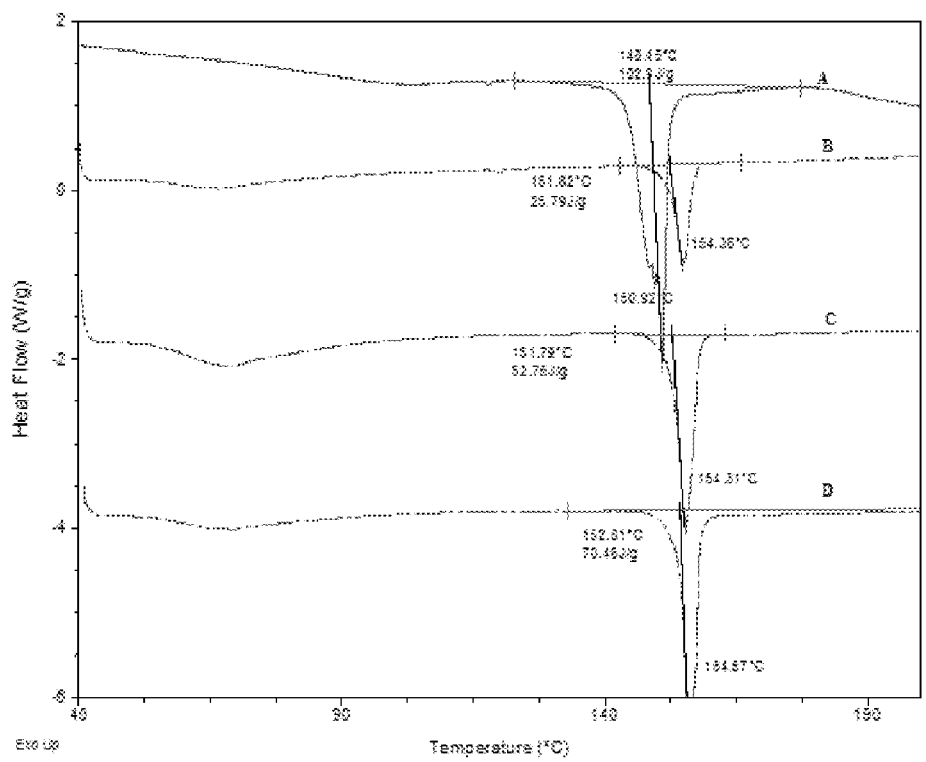
FIG. 19 depicts the DSC thermograms for testosterone-talc non-CIA mixture.

For each CIA or non-CIA system, three different weight ratios of testosterone to agent system namely 70:30, 50:50 and 30:70 were prepared. Each sample of testosterone and CIA system was mixed, heated and allowed to melt at about 80° C. using a water bath. Then the sample was cooled to room temperature and the heat of fusion ($\Delta H_f$) of testosterone was measured at about 150° C. using DSC. Similarly, each sample of testosterone and non-CIA talc was mixed and heated at about 80° C. using a water bath. Then the sample was cooled to room temperature and the heat of fusion ($\Delta H_f$) of testosterone was measured. The DSC thermogram for pure testosterone and testosterone with individual CIAs i.e. polyethylene glycol 8000, Vitamin-E TPGS, lauroyl polyoxyl-32 glycerides, and hydrogenated vegetable oil each with drug-CIA ratio of 70/30, 50/50 and 30/30 are given in FIGS. 15-18. In FIG. 15 A is pure testosterone, B is 30:70 of testosterone: PEG 8000, C is 50:50 of testosterone: PEG 8000 and D is 70:30 of testosterone: PEG 8000. In FIG. 16 A is pure testosterone, B is 30:70 of testosterone: vitamin E-TPGS, C is 50:50 of testosterone: vitamin E-TPGS and D is 70:30 of testosterone: vitamin E-TPGS. In FIG. 17 A is pure testosterone, B is 30:70 of testosterone: lauroyl polxyl-32 glycerides, C is 50:50 of testosterone: lauroyl polyoxyl glycerides and D is 70:30 of testosterone: lauroyl polyoxyl-32 glycerides. In FIG. 18, A is pure testosterone, B is 30:70 of testosterone: hydrogenated vegetable oil, C is 50:50 of testosterone: hydrogenated vegetable oil and D is 70:30 of testosterone: hydrogenated vegetable oil. FIG. 19 depicts the thermogram for testosterone/talc (non CIA) where A is pure testosterone, B is 30:70 of testosterone: talc, B is 50:50 of testosterone: talc and D is 70:30 of testosterone: talc.

Figure 20:
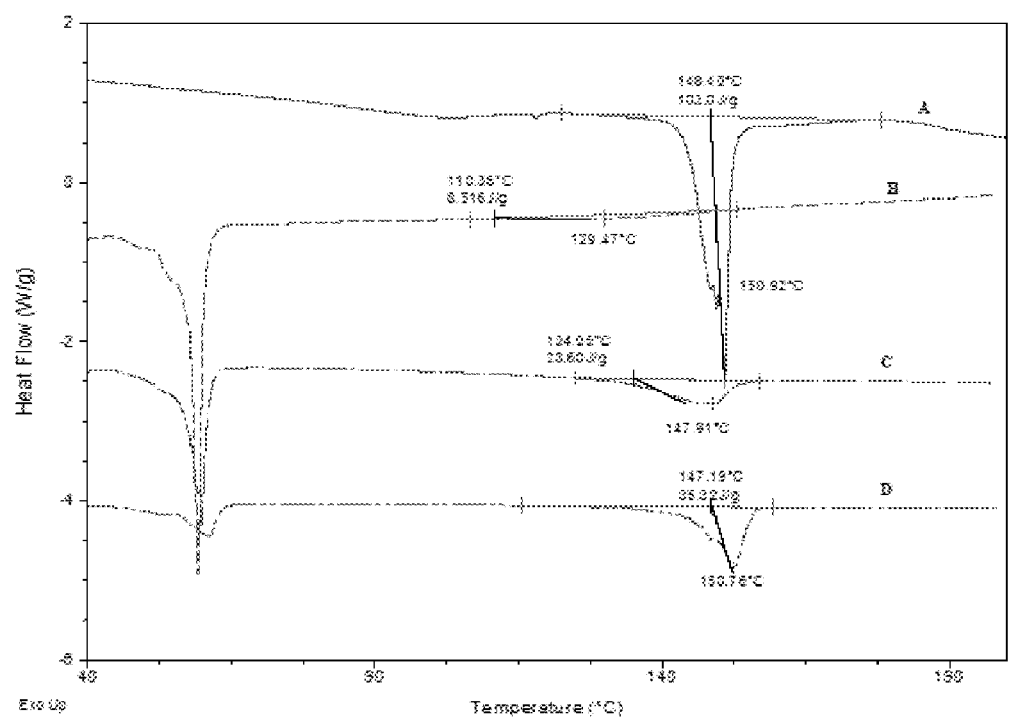
FIG. 20 depicts the DSC thermograms for testosterone-binary CIA systems.

The heat of fusion ($\Delta H_f$) of testosterone values of the single CIA systems such as PEG 8000 and Vitamin-E TPGS, and the binary CIA system of 50% PEG 8000 and 50% Vitamin-E TPGS, are described in Table 17. The heat of fusion ($\Delta H_f$) of testosterone for the heat treated sample of testosterone and the non-CIA talc is listed for comparison. FIG. 20 shows the thermogram for testosterone and binary decrystallization agent combination system in the ratio of 70:30, 50:50 and 30:70. Here the binary decrystallization agent is 1:1 combination of PEG 8000 and Vitamin-E TPGS. In FIG. 20, A is pure testosterone, B is 30:70 of testosterone: binary system, C is 50:50 of testosterone: binary system and D is 70:30 of testosterone: binary system.

TABLE 17

Heat of Fusion (J/g) of Various Single and Binary CIA Systems

| Fraction of CIA or Non-CIA Agent by Weight | Talc | Polyethylene glycol 8000 | Vitamin-E TPGS | Binary CIA System (50:50 w:w) Actual | Calculated |
|---|---|---|---|---|---|
| 0.3 | 70.5 | 41.4 | 43.2 | 35.3 | 42.3 |
| 0.5 | 52.8 | 29.2 | 35.3 | 23.6 | 32.25 |
| 0.7 | 25.8 | 7.1 | 15.3 | 8.5 | 11.2 |

For a system of a non-CIA and testosterone, as the fraction or percentage of the non-CIA increases, the $\Delta H_f$ value of testosterone decreases correspondingly. Moreover, the magnitude of $\Delta H_f$ drop matches with the percent weight decrease of testosterone in the system. This is due to unaltered crystallinity of testosterone in the system. As seen in Table 17, for talc, the percent drop of the heat of fusion matches with the percent weight decrease of testosterone in the system. For example, an about 30% drop of the weight of testosterone in the system, which corresponds to the 0.3 fraction or 30% of talc in the system, leads to an about 30% drop of the heat of fusion of testosterone, or a drop from 102.4 J/g to 70.5 J/g. This data confirms that talc is a non-CIA for testosterone and the testosterone in the talc system is unaffected in its degree of crystallinity.

In contrast, for a system of a CIA and testosterone, as the fraction or percentage of the CIA increases, the percent drop of $\Delta H_f$ is greater than the corresponding percent weight decrease of testosterone in the system. This is due to the decreased degree of crystallinity of testosterone in the system caused by the CIA. The heat of fusion of the testosterone having the reduced crystallinity is less than that of the theoretical heat of fusion for unaffected crystalline testosterone, which is about 102.4 J/g. As revealed in Table 17, for the single CIA system, such as polyethylene glycol 8000 and vitamin E-TPGS, the percent drop of the heat of fusion of testosterone is significantly higher than the corresponding percent weight drop of testosterone in the systems. For instance, an about 60% drop of heat of fusion of testosterone, or a drop of 102.4 J/g to 41.4 J/g was achieved by just a 0.3 fraction of PEG 8000 or a 30% weight drop of testosterone in the system. The data suggests that the single CIA such as polyethylene glycol 8000 and vitamin E-TPGS does have significant decrystallizing effect on testosterone. Due to the presence of these CIAs, testosterone has a reduced degree of crystallinity and hence requires less energy to get solubilized in aqueous environments then its crystalline counterpart.

Surprisingly, a synergistic decrystallization effect was found for the binary CIA system consisting of polyethylene glycol 8000 and vitamin E-TPGS. Based on the system composition and the individual contribution from each CIA, a theoretical heat of fusion of testosterone was calculated. However, as depicted in Table 17, the actual measured heat of fusion of testosterone was significantly less than the calculated mathematic contribution, i.e., the actual drop of heat of fusion of testosterone was more than the theoretical loss. For example, for the system of 30% binary CIA system and 70% testosterone, the theoretical calculated heat of fusion is 42.2 J/g, however, the actual measure heat of fusion of testosterone was 35.5 J/g. In other words, due to the 30% by weight addition of the combination CIA system, the decrease in heat of fusion for testosterone was much more than the decrease calculated mathematically given each individual CIA's contribution. This indicates that the binary CIA system of polyethylene glycol 8000 and vitamin E-TPGS has a synergistic decrystallization effect on testosterone.

Figure 21:
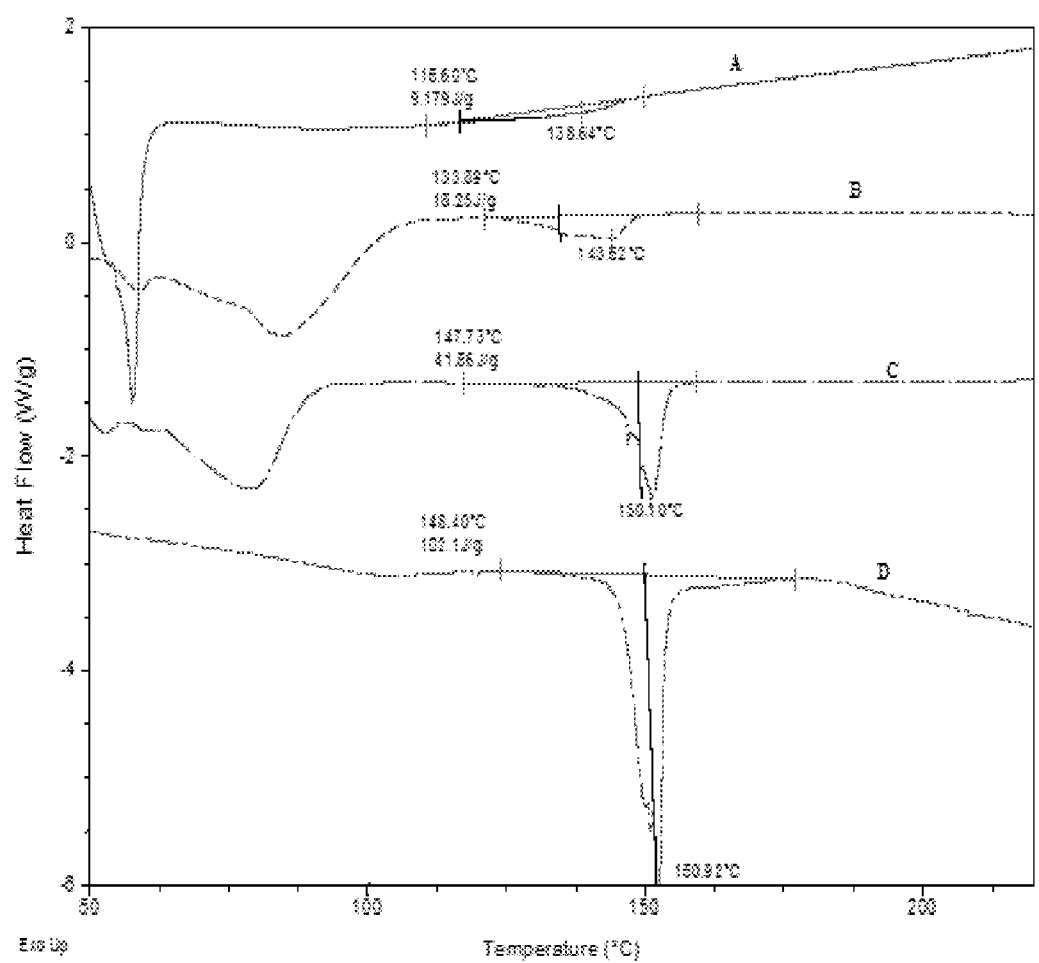
FIG. 21 depicts the DSC thermograms for testosterone-ternary CIA systems.

The heat of fusion ($\Delta H_f$) of testosterone values of the single CIA system such as PEG 8000, lauroyl polyoxyl-32 glycerides and hydrogenated vegetable oil, and the ternary CIA system of, by weight, 40% PEG 8000, 50% lauroyl polyoxyl 32 glycerides, and 10% hydrogenated vegetable oil, are described in Table 18. The DSC thermogram is shown in FIG. 21. In FIG. 21, A is 30:70 of testosterone: ternary system, B is 50:50 of testosterone: ternary system, C is 70:30 of testosterone: ternary system and D is pure testosterone. The heat of fusion ($\Delta H_f$) of testosterone value for the heat treated sample of testosterone and the non-CIA talc is listed again for comparison.

TABLE 18

Heat of Fusion (J/g) of Various Single and Ternary CIA Systems

| Fraction of CIA or Non-CIA Agent by Weight | Fraction of Testosterone by Weight | Talc | Polyethylene glycol 8000 | Lauroyl polyoxyl-32 glycerides | Hydrogenated Vegetable Oil | Ternary CIA System | |
|---|---|---|---|---|---|---|---|
| | | | | | | Actual | Theoretical |
| 0.3 | 0.7 | 70.5 | 41.4 | 50.6 | 46.5 | 41.9 | 46.6 |
| 0.5 | 0.5 | 52.8 | 29.2 | 19.8 | 23.7 | 18.3 | 24.0 |
| 0.7 | 0.3 | 25.8 | 7.1 | 9.8 | 6.8 | 9.2 | 8.5 |

As revealed in Table 18, for each single CIA system, such as PEG 8000, lauroyl polyoxyl-32 glycerides and hydrogenated vegetable oil, the percent drop of the heat of fusion of testosterone is significantly higher than the corresponding percent weight drop of testosterone in the systems. For instance, an about 50% drop of heat of fusion of testosterone, or a drop of 102.4 J/g to 50.6 J/g was achieved by just a 0.3 fraction of lauroyl polyoxyl-32 glycerides or a 30% weight drop of testosterone in the system. The data suggest that each of the single CIA such as PEG 8000, lauroyl polyoxyl-32 glycerides and hydrogenated vegetable oil does decrystallize testosterone. Due to the presence of these CIAs, testosterone has a reduced degree of crystallinity.

Furthermore surprisingly a synergistic decrystallization effect was found with a ternary CIA system of PEG-8000, lauroyl polyoxyl-32 glycerides and hydrogenated vegetable oil. Based on the system composition and the individual contribution from each CIA, a theoretical heat of fusion of testosterone was calculated. However, the actual measured heat of fusion of testosterone was found to be significantly less than the calculated mathematic contribution, i.e., the actual drop of heat of fusion of testosterone was more than the theoretical loss. For example, for the CIA system having a fraction of 0.5, the theoretical calculated heat of fusion is 24.0 J/g, however, the actual measure heat of fusion of testosterone was 18.3 J/g. In other words, due to the 50% by weight addition of the CIA system, the decrease of heat of fusion for testosterone is much more than the decrease that was expected mathematically given each individual CIA's contribution. This indicates that the ternary CIA system of PEG 8000, lauroyl polyoxyl-32 glycerides and hydrogenated vegetable oil shows a synergistic decrystallization effect on testosterone.

Figure 22:
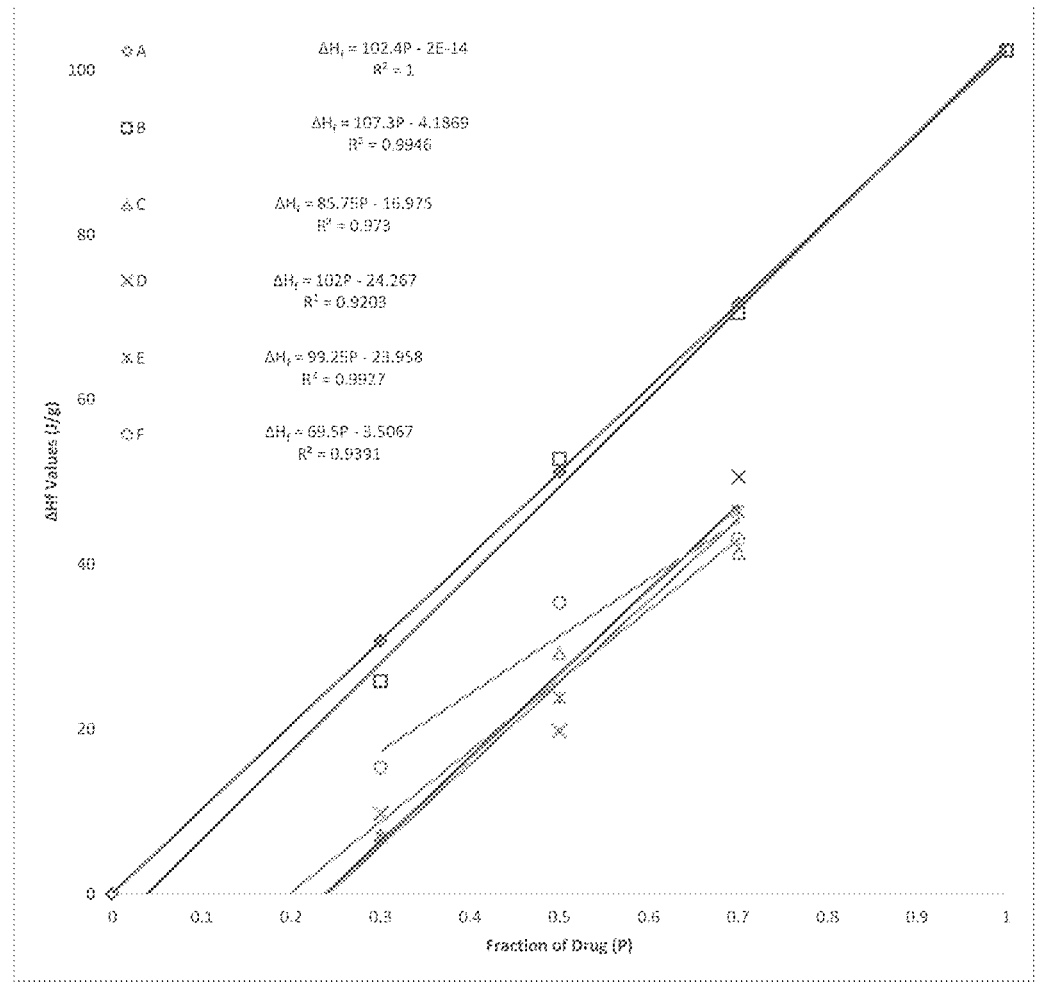
FIG. 22 depicts a graph showing the effect of various single CIAs on the heat of fusion for testosterone.
Figure 23:
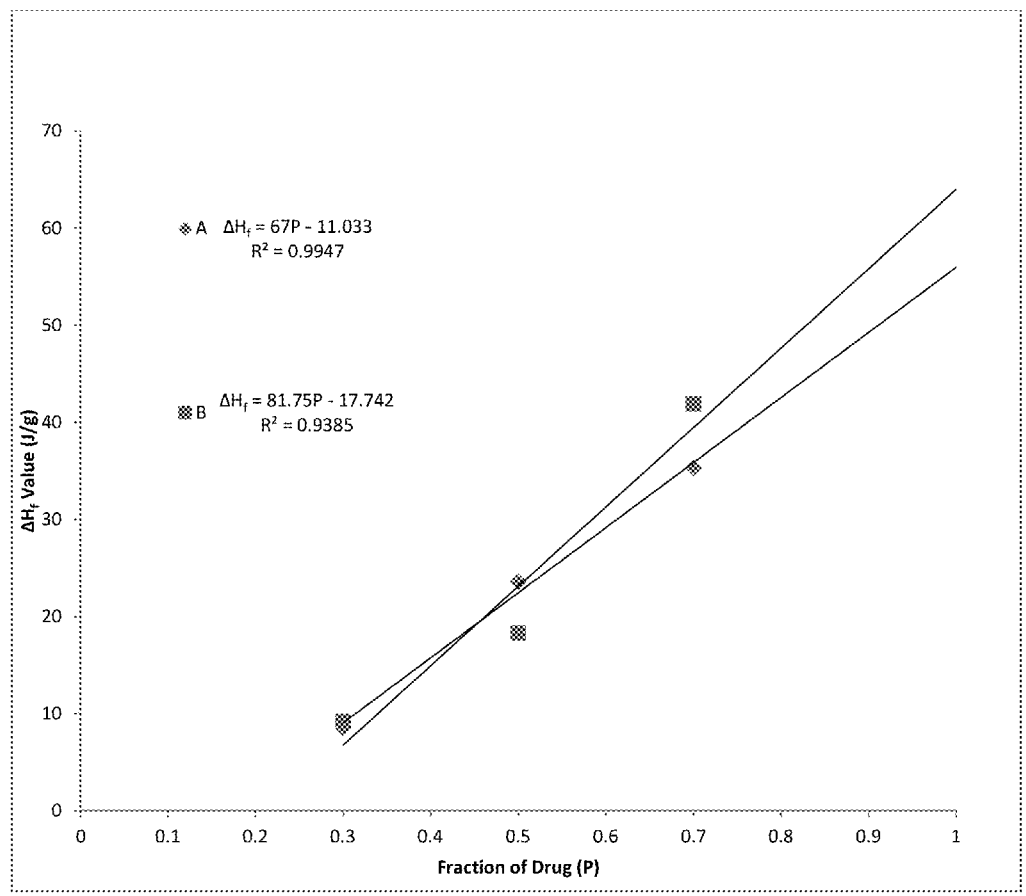
FIG. 23 depicts a graph showing the effects of binary and ternary CIA systems on the heat of fusion for testosterone.

The heat of fusion ($\Delta H_f$) of testosterone for various single CIA systems versus the fraction of drug was plotted in FIG. 22. The Y-axis is the $\Delta H_f$ (J/g) of testosterone with various single CIA systems. The X-axis is the fraction of testosterone in the system. In FIG. 22, line A corresponds to the arithmetically calculated theoretical value based on the decreasing weight ratio of testosterone of 100% crystallinity, line B corresponds to talc, line C corresponds to polyethylene glycol 8000, line D corresponds to lauroyl polyoxyl-32 glycerides, line E corresponds to hydrogenated vegetable oil and line F corresponds to Vitamin-E TPGS. FIG. 23 shows a plot of $\Delta H_f$ vs. fraction of testosterone in the system for binary and ternary system. Plot A represents PEG 8000/Vitamin-E TPGS (1:1), and plot B represents PEG/hydrogenated vegetable oil/lauroyl polyoxyl-32 glycerides (4:1:5) system.

Figure 24:
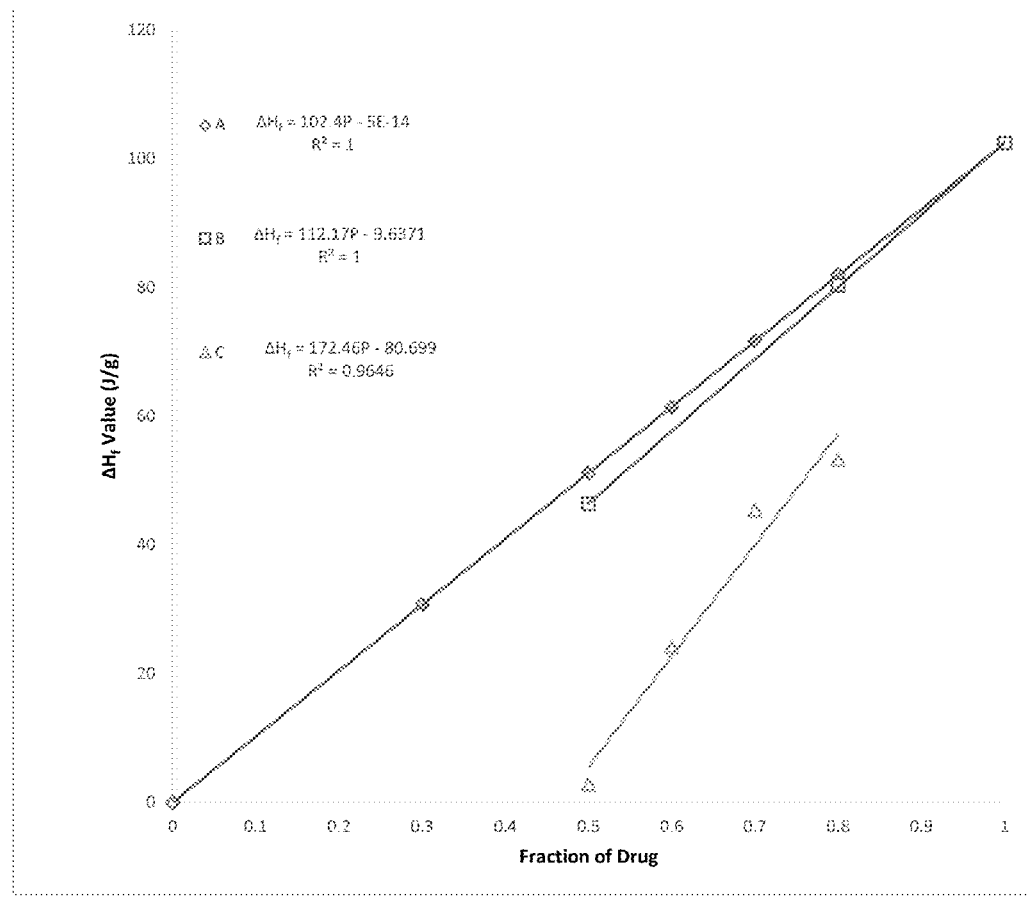
FIG. 24 depicts a graph showing the effect on heat of fusion of CIA-drug combination prepared by solvent evaporation process for testosterone.

A linear regression was performed to model the relationship between the heat of fusion and fraction of testosterone in the system for each CIA system. The linear regression of the plot of heat of crystallization ($\Delta H_f$) versus fraction of drug (P) in the CIA present in the system is given in equation 1.

$$\Delta H_f = m(P) + C \quad \text{(Eq. 1)}$$

Where m is the slope and C is the Y-intercept of the line ($\Delta H_f$ vs. P plot). The m and C values for the various CIA systems shown in FIGS. 22, 23 and 24 are provided in the following table:

TABLE 21 m and C values for different CIA systems

| CIA system | Slope (m) | Y-intercept (C) |
|---|---|---|
| Polyethylene glycol 8000 | 85.8 | −17.0 |
| Lauroyl polyoxyl-32 glycerides | 102.0 | −24.3 |
| Hydrogenated vegetable oil | 99.2 | −23.9 |
| Vitamin E-TPGS | 69.7 | −3.6 |
| Polyvinylpyrrolidone K-30 | 172.5 | −80.7 |
| Binary system | 67.0 | −11.0 |
| Ternary system | 81.7 | −17.7 |

If the fraction of the CIA in the system is Q, than P+Q=1 or P=(1−Q). The equation 1 can be rearranged as below (equation 2)

$$Q = 1 - (\Delta H_f/m) + (c/m) \quad \text{(Eq. 2)}$$

The fraction of CIA Q required to achieve $\Delta H_f=0$ i.e., complete decrystallization for a drug, is derived from equation 2 as below:

$$Q_{\Delta H_f=0} = 1 + (c/m) \quad \text{(Eq. 3)}$$

The term $Q_{\Delta H_f=0}$ in equation 3 is referred to as Decrystallization Potential in this invention. Thus the decrystallization potential of a CIA is a measure of its ability to decrystallize organic compound i.e., a drug of interest. It can be defined as the fraction of the CIA(s) in a system containing the drug to completely nullify its $\Delta H_f$. The decrystallization potential value of a CIA may vary from drug to drug or for a particular drug, variation in the CIA will have variation in decrystallization potential values.

The $\Delta H_f$ versus P plot for single, binary, and ternary CIAs with testosterone are shown in FIGS. 22 and 23. Based on the linear regression straight line, the slop (m), the intercept (C) values are utilized to calculate the decrystallization potential for the particular CIA for testosterone as given in Table 22.

TABLE 22

Decrystallization potential of several single, binary, and ternary CIAs for testosterone.

| CIA | Decrystallization potential value ($Q_{\Delta Hf=0}$) | CIA will achieve complete Decrystallization at a ratio of CIA/Testosterone |
|---|---|---|
| Polyvinylpyrrolidone K-30 | 0.53 | 0.53/0.47 |
| Lauroyl polyoxyl-32 glycerides | 0.76 | 0.76/0.24 |
| Hydrogenated vegetable oil | 0.76 | 0.76/0.24 |
| PEG-8000/Lauroyl polyoxyl-32 glycerides/ Hydrogenated vegetable oil (40/10/50) | 0.78 | 0.78/0.22 |
| PEG-8000 | 0.80 | 0.80/0.20 |
| PEG-8000/Vitamin-E TPGS (50/50) | 0.84 | 0.84/0.16 |
| Vitamin E TPGS | 0.95 | 0.95/0.05 |
| Talc | 1.00 | Not effective |

The lower the $Q\Delta_{Hf=0}$ value the lower the amount of CIA required to nullify the $\Delta H_f$ of a drug substance. In this invention a value of decrystallization potential is >0 and <1.0. A value of 1.0 or close to 1.0 indicates no decrystallization effect. The decrystallization potential value ($Q_{\Delta Hf=0}$) can be useful in identifying appropriate quantity of CIA in a formulation to achieve $\Delta H_f=0$ thereby obtaining a molecular dispersion that would facilitate drug dissolution and absorption. Additionally, the synergistic property of combined CIA system can exploited to achieve benefit of both the components. For example Vitamin-E TPGS exhibit weak decrystallization potential ($Q_{\Delta Hf=0}=0.95$) compare to PEG-8000 ($Q_{\Delta Hf=0}=0.80$). However, vitamin-E TPGS is more beneficial to maintain a high concentration of testosterone at the dissolving surface (without micro-environmental crystallization) thereby improving drug dissolution and absorption. A 50/50 combination of PEG-8000/vitamin-E TPGS with a $Q_{\Delta Hf=0}$ value of 0.84 could maximize the drug load for complete decrystallization as well as improving the dissolution and absorption potential of the formulation.

The $Q_{\Delta Hf=0}$ value can also be used to predict the effectiveness of combination CIA systems for a drug using the $Q_{\Delta Hf=0}$ values of their individual components and the ratios of those components in the particular system. For instance, the theoretically calculated value for the ternary system of PEG 8000: lauroyl polyoxyl-32 glycerides: hydrogenated vegetable oil (4:1:5) has a theoretical $Q_{\Delta Hf=0}$ value of $[(0.8\times0.4)+(0.76\times0.1)+(0.76\times0.5)]=0.776$ vs. the actual $Q_{\Delta Hf=0}$ value of 0.78. The binary system of Vitamin-E TPGS: PEG 8000 (1:1) has a theoretical $Q_{\Delta Hf=0}$ value of $[0.95\times0.5)+(0.8\times0.5)]=0.875$ vs. the actual 0.84. Thus the equation to identify the $Q_{\Delta Hf=0}$ for a combination system containing component a, b, c n can be represented by, $$Q_{(\Delta Hf=0)a,b,c...n} = \Sigma(Q_{(\Delta Hf=0)a,b,c...n} \times f_{a,b,c...n}) \quad \text{(Eq. 4)}$$

As described above, this invention provides a method of using DSC data of individual CIAs to design potential combination systems between said agents. Some CIAs may offer desirable drug absorption properties but with poor decrystallization ability (high $Q_{\Delta Hf=0}$ value). They can be combined with one or more CIAs with a low $Q_{\Delta Hf=0}$ value to decrease the decrystallizing potential of the combination system. So, the $Q_{\Delta Hf=0}$ value of individual components can be used to predict the $Q_{\Delta Hf=0}$ values of feasible combination systems that maximize the drug absorption in vivo.

The linear regression equation (Eq. 1) can be utilized to estimate the fraction of testosterone in the system for each single or combination CIA. Thus, this information can be used to design a dosage form comprising a drug having a desired degree of the reduced crystallinity, such as a completely decrystallized drug, such as testosterone. For example, the CIA system of PEG 8000, lauroyl polyoxyl-32 glycerides and hydrogenated vegetable oil were design in the primary vehicle of Example 1 as described in Table 1 and Example 2 as depicted in Table 3. Moreover, the primary vehicle comprising a single or combination CIA designed by this method contains a completely decrystallized drug. For instance, as evident from the XRPD diffractogram shown in FIG. 9, the testosterone in the synergistic CIA system of lauroyl polyoxyl-32 glycerides, hydrogenated vegetable oil and polyethylene glycol 8000, shows significantly decreased intensity of diffraction peaks, indicating the complete loss of crystallinity of the testosterone in the synergistic CIA system.

The linear regression equation (Eq. 1) can also be used to design partially decrystallized individual or combination systems. The desired $\Delta Hf$ values can be input into Eq. 1 to result in the fraction of drug, hence the fraction of CIA that will be required. For example, if 50% decrystallization (i.e. 50% $\Delta H_f$ value of original) of testosterone is desired then the fraction of testosterone used (P) for PEG 8000 will be calculated in the following way:

$$102.4 \times 0.5 = 85.75P - 16.975$$

or, $$P = 0.795$$

The same can be applied to any single or combination CIA systems where the linear regression of fraction of drug vs. the $\Delta H_f$ values is available.

In addition, the decrystallizing ability of a hydrophilic CIA polyvinylpyrrolidone (PVP) copolymer on testosterone was evaluated via the heat of fusion ($\Delta H_f$) measurement. In this case, sample of testosterone PVP system was prepared via a solvent evaporation method. Five different weight ratios of testosterone to PVP namely 20:80, 30:70, 40:60, 50:50 and 70:30 were prepared. Each sample of testosterone and PVP were mixed and dissolved in isopropyl alcohol (IPA). The testosterone-PVP solid dispersion sample was then obtained by drying the testosterone/PVP solution in an oven and its heat of fusion ($\Delta H_f$) was measured via DSC. Moreover, as a control, samples of testosterone and the non-CIA talc were also evaluated. Two different weight ratios of testosterone to talc namely 80:20 and 50:50 were prepared. Each sample of testosterone and talc were mixed and soaked in isopropyl alcohol (IPA) to dissolve testosterone. The testosterone-talc sample was then obtained by drying the testosterone/talc IPA dispersion in the oven and its heat of fusion ($\Delta H_f$) was measured via DSC.

The heat of fusion ($\Delta H_f$) of testosterone values of the single CIA system of PVP are described in Table 23. The heat of fusion ($\Delta H_f$) of testosterone value for the IPA treated sample of testosterone and the non-CIA talc is listed for comparison.

TABLE 23

Heat of Fusion PVP CIA system

| Fraction of CIA or Non-CIA Agent by Weight | Fraction of Testosterone by Weight | Heat of Fusion (J/g) Actual | | Theoretical |
|---|---|---|---|---|
| | | PVP | Talc | |
| 0 | 1 | — | — | 102.4 |
| 0.2 | 0.8 | 53.2 | 80.3 | 81.9 |
| 0.3 | 0.7 | 45.4 | — | 71.7 |
| 0.4 | 0.6 | 24.2 | — | 61.4 |
| 0.5 | 0.5 | 2.8 | 46.4 | 51.2 |
| 0.7 | 0.3 | 0 | — | 30.7 |

As revealed in Table 23, for the single CIA system of PVP, the percent drop of the heat of fusion of testosterone is significantly higher than the corresponding percent weight drop of testosterone in the systems. For instance, an about 50% drop of heat of fusion of testosterone, or a drop of 102.4 J/g to 53.2 J/g was achieved by just a 0.2 fraction of PVP or a 20% weight drop of testosterone in the system. The data indicates that the single CIA PVP does decrystallize testosterone. Due to the presence of PVP, testosterone exhibits low crystallinity and more disordered in the system, thereby the system would facilitate dissolution and absorption.

The heat of fusion (ΔHf) of testosterone in various single CIA systems of PVP was plotted in FIG. 24. The Y-axis is the ΔHf (J/g) of testosterone of various single CIA systems. The X-axis is the fraction of testosterone in the system. In FIG. 24, line A corresponds to the arithmetically calculated theoretical value based on the decreasing weight ratio of testosterone of 100% crystallinity, line B corresponds to talc, and line C corresponds to PVP. A linear regression was performed to model the relationship between the heat of fusion ($\Delta H_f$) and fraction of testosterone (P) in the system. The data fits a model that can be represented satisfactorily by Eq. 1.

Example 10

Solubility of Testosterone in Molten CIA Systems

The process of solubilization for a crystalline drug is also a process of breaking the crystal bonds between the drug molecules and transforming the drug from highly organized, lattice-like structures to a disordered molecular form. Thus when a crystalline drug is completely dissolved in a solvent, it exists in that solvent in a form of a completely or substantially reduced degree of crystallinity or in a non-crystalline form. In addition to the mathematical model developed to predict the decrystallization ability of the CIA system, the capacity or the limit of a CIA to completely decrystallize a drug, such as testosterone, i.e., the solubility of testosterone in a CIA was also determined.

Testosterone solubility in various molten single CIA systems, such as polyethylene glycol 8000, oleic acid and vitamin E-TPGS were measured. Moreover, a simplex-centroid design was carried out to evaluate the impact of various combination CIA systems on testosterone solubility. The experimental design and results are reported in Table 24.

In each solubility study, a molten solvent of single or combination CIA was prepared by heating and melting the CIA system using a water bath. An excess quantity of testosterone was added and mixed with each CIA system until a precipitation of un-dissolved testosterone was observed. The melt suspension was mixed for at least another 30 minutes while maintaining the CIA's molten state. The supernatant of the melt mixtures were sampled and analyzed for testosterone concentration using a HPLC method.

Discussion:

As depicted in Table 24, testosterone has a solubility of about 175.9 mg/gm in molten polyethylene glycol 8000, about 58.3 mg/gm in molten oleic acid and about 78.9 mg/gm in molten vitamin E-TPGS.

Surprisingly, a synergistic solubilization effect was found for the molten combination CIA systems. The actual solubility of testosterone in the molten CIA combinations was significantly higher than the theoretical values expected based on the individual solubility contribution from each CIA.

Thus, the single CIA such as polyethylene glycol 8000, oleic acid or vitamin E-TPGS has the ability of maintaining testosterone in its molecular form (decrystallized) in solidified molten system dispersed in the CIA. Moreover, combining CIAs of polyethylene glycol 8000, oleic acid or vitamin E-TPGS produces a synergistic effect on the solubility of testosterone in the molten mass solid state thereby higher concentration of molecular dispersion of the drug in the CIA systems.

Figure 25:
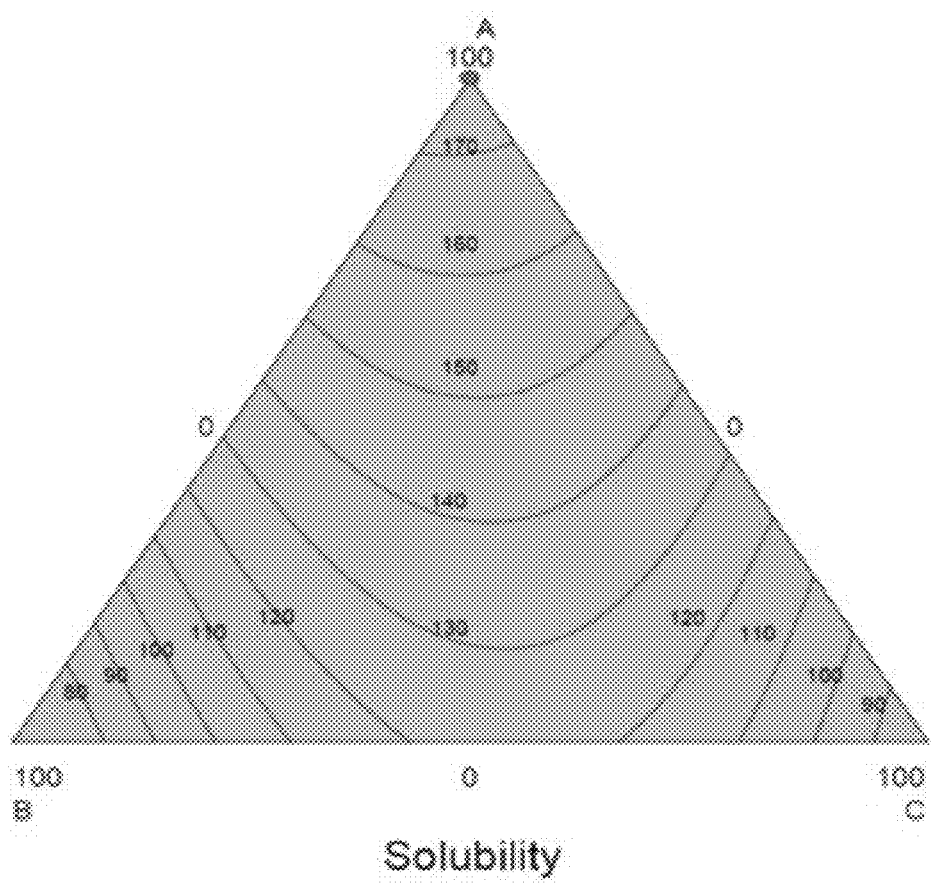
FIG. 25 depicts a-contour plot generated using Design-Expert® software for the solubility of testosterone in polyethylene glycol 8000, vitamin E-TPGS, and/or oleic acid, as described in Example 13(a).

The highest synergy in solubilization (80%) was observed for a molten mixture of oleic acid and vitamin E-TPGS combination (50:50 w:w). The solubility equation for testosterone generated from solubility values using the simplex-centroid design system of polyethylene glycol, oleic acid and vitamin E-TPGS is:

Solubility=175.9a+58.3b+78.9c+76.4ab+42.0ac+
220.0bc+144.9abc    (Eq. 5)

where "a, b and c" refers to proportions of polyethylene glycol 8000, oleic acid and vitamin E-TPGS respectively in the system. A contour plot generated from the testosterone solubility values using Design-Expert® Software is depicted in FIG. 25. In this figure, apex A corresponds to polyethylene glycol 8000, apex B corresponds to oleic acid and apex C corresponds to vitamin E-TPGS.

TABLE 24

| Molten CIA Composition | | | Solubility of Testosterone in CIA | |
|---|---|---|---|---|
| Polyethylene glycol 8000 (%) | Oleic Acid (%) | Vitamin E-TPGS (%) | Actual (mg/gm) | Theoretical (mg/gm) |
| 100 | 0 | 0 | 175.9 | — |
| 0 | 100 | 0 | 58.3 | — |
| 0 | 0 | 100 | 78.9 | — |
| 50 | 50 | 0 | 136.2 | 117.1 |
| 50 | 0 | 50 | 137.9 | 127.4 |
| 0 | 50 | 50 | 123.6 | 68.6 |
| 33.3 | 33.3 | 33.3 | 136.6 | 104.4 |

Additional simplex-centroid design was carried out for the molten combination CIA system of polyethylene glycol 8000, vitamin E-TPGS and lauroyl polyoxyl-32 glycerides. The experimental design and results are reported in Table 25.

Again, a synergistic solubilization effect was found for the molten combinations of CIAs. The actual solubility of testosterone in the molten CIA combinations was significantly higher than the theoretical values expected based on the individual solubilizing contribution from each CIA.

Thus, the single CIA such as lauroyl polyoxyl-32 glycerides demonstrates the ability of maintaining testosterone in its molecular form (decrystallized) in solidified molten system of the CIA. Moreover, combining CIAs of polyethylene glycol 8000, vitamin E-TPGS or lauroyl polyoxyl-32 glycerides produces a synergistic effect on the solubility of testosterone in the molten mass thereby solid state molecular dispersion of the CIA systems.

Figure 26:
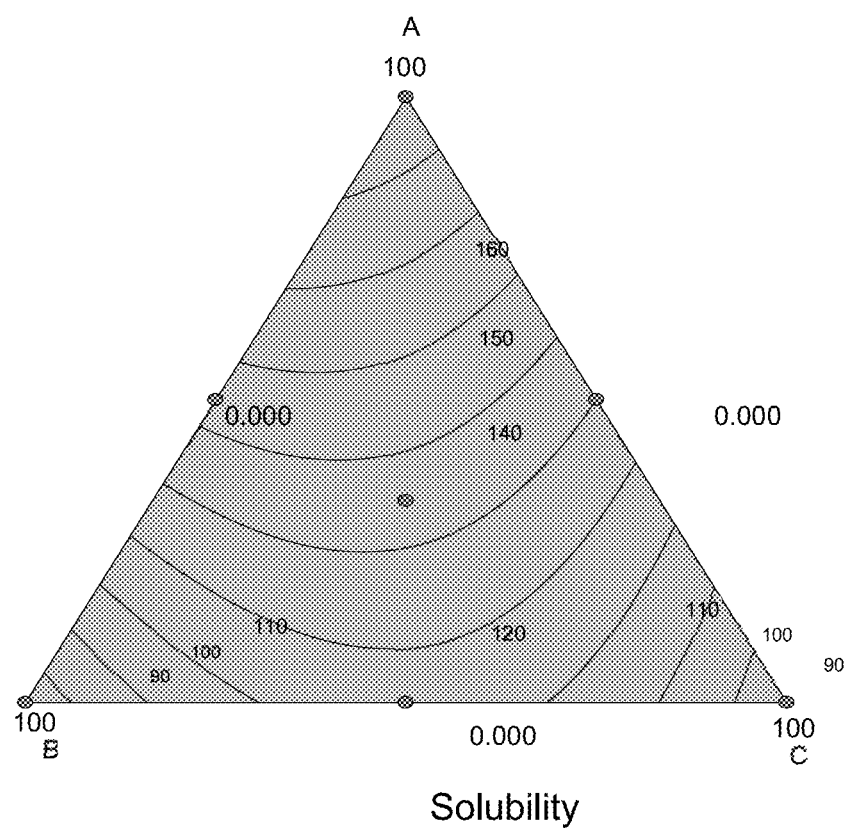
FIG. 26 depicts a contour plot generated using Design-Expert® software for the solubility of testosterone in polyethylene glycol 8000, vitamin E-TPGS, and/or lauroyl polyoxyl-32 glycerides as described in Example 13(b)

The solubility equation for testosterone generated from solubility values using the simplex-centroid design system of polyethylene glycol, vitamin E-TPGS and lauroyl polyoxyl-32 glycerides is:

$$\text{Solubility} = 178.4a + 82.7b + 81.6c + 54.9ab - 0.09ac + 130.1bc \quad \text{(Eq. 6)}$$

where "a, b and c" refers to proportions of polyethylene glycol, vitamin E-TPGS and lauroyl polyoxyl-32 glycerides respectively in the system. A contour plot generated from the testosterone solubility values using Design-Expert® Software is depicted in FIG. 26. In this figure, apex A corresponds to polyethylene glycol 8000, apex B corresponds to vitamin E-TPGS and apex C corresponds to lauroyl polyoxyl-32 glycerides.

TABLE 25

| Molten CIA Composition | | | Solubility of Testosterone in CIA | |
|---|---|---|---|---|
| Polyethylene glycol 8000 (%) | Vitamin E TPGS (%) | Lauroyl polyoxyl-32 glycerides (%) | Actual (mg/gm) | Theoretical (mg/gm) |
| 100 | 0 | 0 | 178.4 | — |
| 0 | 100 | 0 | 82.7 | — |
| 0 | 0 | 100 | 81.6 | — |
| 50 | 50 | 0 | 144.2 | 130.6 |
| 50 | 0 | 50 | 129.9 | 130.0 |
| 0 | 50 | 50 | 114.6 | 82.2 |
| 33.3 | 33.3 | 33.3 | 134.9 | 114.1 |

Example 11

Testosterone Solubility in Aqueous Media Containing Various CIAs

This invention also involved the ability of various CIAs to maintain testosterone in its molecular level in solution state or to solubilize testosterone in an aqueous media was evaluated. For each CIA, such as polyethylene glycol 8000, vitamin E-TPGS, lauroyl polyoxyl-32 glycerides and oleic acid, various media of Simulated Saliva Fluid (SSF) containing different concentrations of CIA, such as 0%, 0.25%, 5%, 10% and 20% were prepared. Excess quantity of testosterone was added to each aqueous medium and the sample was shaken overnight. Then the sample was filtered through a 0.45 µm polyvinylidene fluoride (PVDF) and the filtrate was analyzed by HPLC.

TABLE 26

Solubility of Testosterone in Various Concentrations of CIA Containing SSF (µg/mL)

| Percentage of CIA in System | Polyethylene Glycol | Vitamin E-TPGS | Lauroyl Polyoxyl-32 Glycerides | Oleic Acid |
|---|---|---|---|---|
| 0 | 24.2 | 24.2 | 24.2 | 24.2 |
| 0.25 | 28.1 | 60.8 | — | — |
| 0.5 | 27.8 | 90.1 | — | — |
| 5 | 32 | 600 | 358 | 27 |
| 10 | 45 | 1210 | 694 | 29 |
| 20 | 69.4 | 2250 | 1348 | 29 |
| Saturated CIA Solution* | 1600 | 4190 | 2370 | — |

*The saturated CIA solution represents 1.73 g/mL of polyethylene glycol, 0.53 g of vitamin E TPGS and 0.34 g/mL of lauroyl polyoxyl-32 glycerides in SSF.

Discussion

Figure 27:
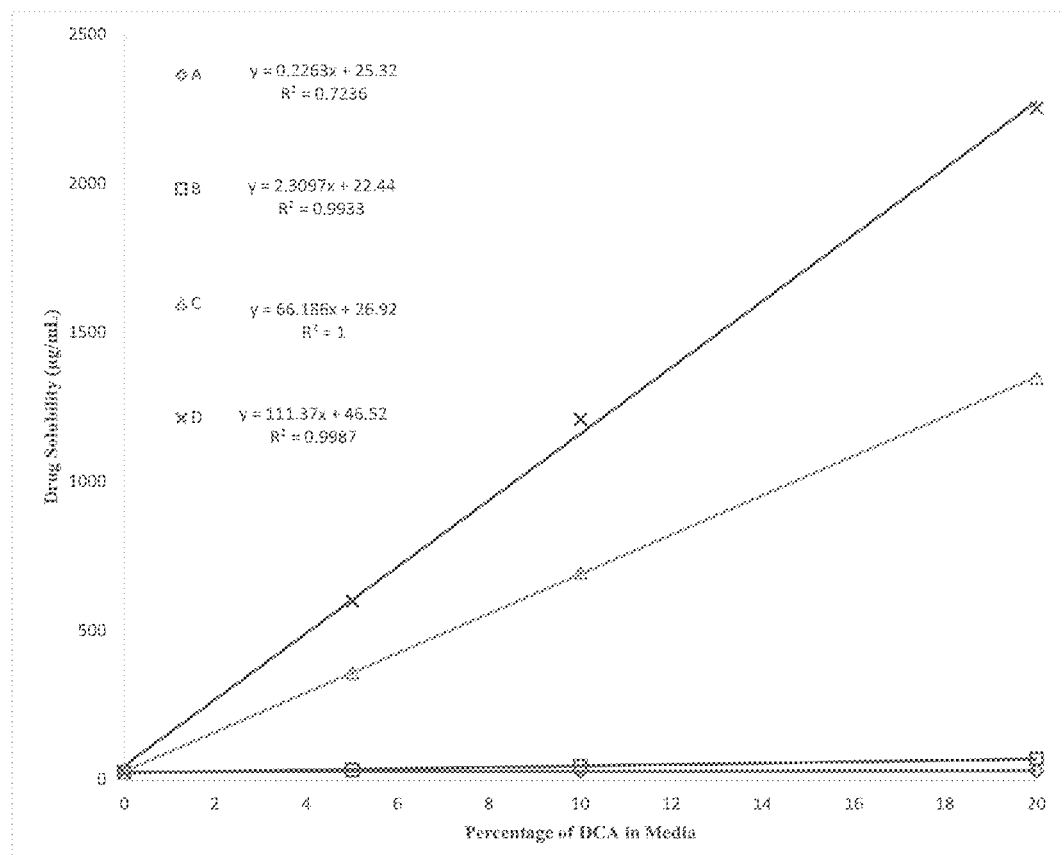
FIG. 27 depicts plots of testosterone solubility versus CIA concentration with the corresponding linear regression curve and equation.

Testosterone solubility in various concentrations of CIAs such as polyethylene glycol, vitamin E-TPGS, lauroyl polyoxyl-32 glycerides and oleic acid in SSF are given in Table 26. Plots of testosterone solubility versus CIA concentration up to 20% along with the corresponding linear regression curve and equation are depicted in FIG. 27 where aqueous solubility of testosterone in SSF with varying concentrations of oleic acid, polyethylene glycol 8000, lauroyl polyoxyl-32 glycerides and vitamin E-TPGS is represented by A, B, C and D respectively. The data from oleic acid was not conclusive as oleic acid itself is not soluble in SSF. A gradual increase in solubility due to increase in concentration of both vitamin E-TPGS and lauroyl polyoxyl-32 glycerides were observed. Surprisingly at the saturated concentrations for CIAs a significant increase in drug solubility was observed in case of polyethylene glycol. The order of solubility at saturated CIA concentrations in aqueous media of SSF was vitamin E-TPGS>lauroyl polyoxyl-32 glycerides>polyethylene glycol.

This data indicates that in the physiological media such as SSF where drug absorption from transmucosal dosage form takes place, the CIAs such as polyethylene glycol, vitamin E-TPGS and lauroyl polyoxyl-32 glycerides can help maintain the insoluble drugs such as testosterone in its molecular level at a high concentration in solution state without any possibility of precipitation thereby improving potentials of absorption and bioavailability.

Thus CIA systems not only have the ability of maintaining insoluble drug such as testosterone in decrystallized molecular form in solid state, it can also help maintain the insoluble drug in its molecular level at a high concentration in solution state in the physiological media simulated saliva fluid (SSF) without any possibility of precipitation. This is significant because dissolution in an aqueous environment is a prerequisite for drug absorption in vivo.

Thus, the CIA containing dosage form of the invention offers an advantage over existing dosage forms in that the dosage form of the invention solubilizes even poorly soluble drugs during manufacturing of the dosage form, maintains the drug in its molecular form in the solid dosage form, and can ensure the drug remains fully in molecular form (solution), minimizing precipitation, in vivo. The ability of CIA(s) to maintain molecular dispersion of the drug in the dosage form thereby facilitating the release of the drug in an environment rich with the CIA preventing precipitation of poorly soluble drugs thereby improving bioavailability and therapeutic effectiveness.

Example 12

In Vitro Diffusion Studies of Testosterone from Various CIA Systems across Polysulfone Membrane A molten solvent of various CIA systems as specified in Table 27 was prepared by heating and melting each CIA system using a water bath. Testosterone was added, mixed and dissolved until clear melt dispersion was obtained. Then sorbitol (or sorbitol/menthol) powder was incorporated with continuous mixing to obtain homogenous granules. Subsequently, the granules were allowed to cool to room temperature and passed through a #30 mesh screen.

TABLE 27

| | Sample No. | | | | | |
|---|---|---|---|---|---|---|
| | # 48A & 54A | # 49A & 55A | # 50A & 56A | # 51A & 57A | # 52A & 58A | # 53A & 59A |
| Ingredients in Melt Dispersion | | | | | | |
| Testosterone | 0.05 g | 0.05 g | 0.05 g | 0.05 g | 0.05 g | 0.05 g |
| Vitamin E-TPGS | — | 0.95 g | — | 0.95 g | 0.95 g | 0.95 g |
| Polyethylene glycol | 0.95 g | — | — | — | — | — |
| Lauroyl polyoxyl-32 glycerides | — | — | 0.95 g | — | — | — |
| Oleic acid | — | — | — | 0.20 g | 0.20 g | — |
| Lecithin | — | — | — | — | 0.05 g | — |
| Granulation | | | | | | |
| Sorbitol | 6.0 g | 6.0 g | 6.0 g | 6.0 g | 6.0 g | 6.0 g |
| Menthol | — | — | — | — | — | 0.05 g |
| Total | 7.0 g | 7.0 g | 7.0 g | 7.2 g | 7.25 g | 7.05 g |

The various testosterone CIA systems were evaluated to determine testosterone diffusion ability across a polymer (polysulfone) membrane with an opening diameter of 0.45 μm using Franz diffusion cell apparatus at 37° C. Donor cell medium was 2 mL Simulated Saliva Fluid (SSF) (pH 7.4). Receptor cell medium was 7 mL Phosphate Buffered Saline (PBS) solution with 4% or 20% Bovine Serum Albumin (BSA). A dose of 2 mg testosterone was loaded into the donor cell for each testosterone CIA system. Albumin was incorporated in the receptor cell medium because testosterone is present in the blood circulation mainly in protein bound (96%) format. In males, about 44% is bound to Sex Hormone Binding Globulin (SHBG), 50% to albumin and 2-3% 'free' (Ref.: Manni A, Pardrige W M, Cefalus W, Nisula B C, Bardin C W: Bioavailability of albumin-bound testosterone. J Clin Endocrinol Metab 61:705, 1985.). Serum albumin concentration is typically about 40 g/L or 4%. Diffusion experiments across polymer membranes were conducted using both the typical BSA concentration (4%) and a high BSA concentration (20%). The high concentration was evaluated because this high BSA concentration (20%) was used for the permeability study across NHu-3D EpiOral buccal epithelial mucosal tissue to minimize testosterone retention in the epithelial cells.

Figure 28:
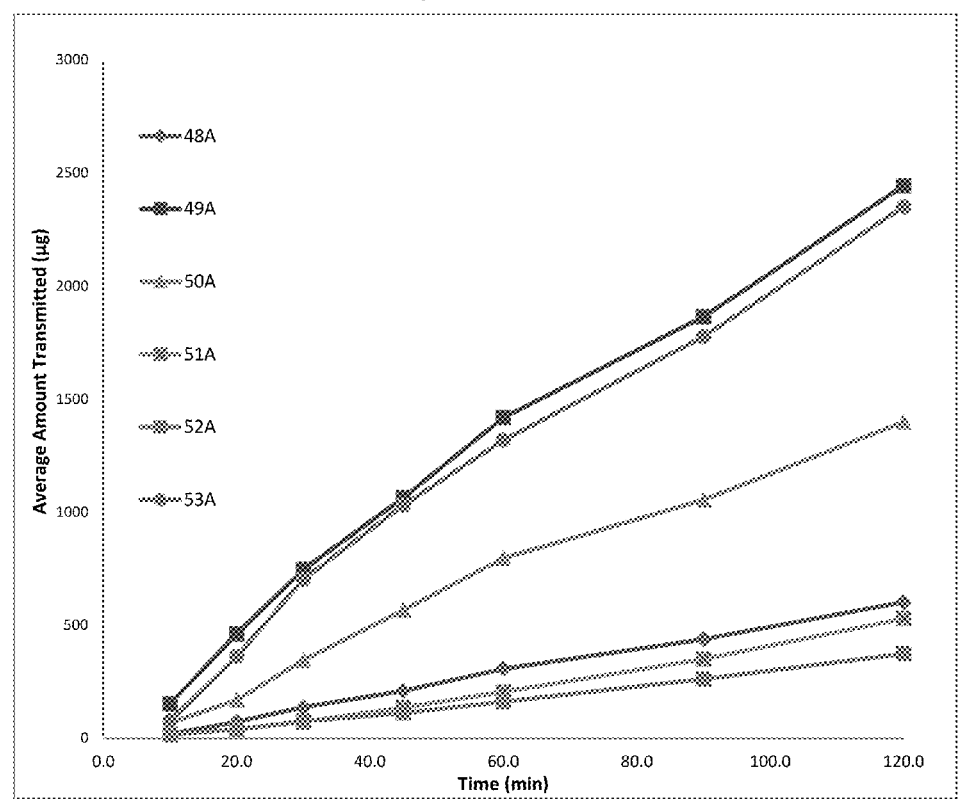
FIG. 28 depicts a graph corresponding to diffusion profiles of various testosterone CIA systems evaluated for testosterone diffusion across 0.45 μm polysulfone membranes with 4% BSA receptor cell medium.

Discussion I:

The diffusion data and profiles of various testosterone CIA systems across the polysulfone membrane with 4% BSA in the receiver cell are given in Table 28, and the graph corresponding to these profiles are shown in FIG. 28. The testosterone/vitamin E-TPGS CIA system (#49A) showed the highest diffusion ability or flux (691.3 μg/cm$^2$/hr) of all the testosterone CIA systems. The addition of menthol in the vitamin E-TPGS CIA system (#53A) did not change this high diffusion ability (665.0 vs. 691.3 μg/cm$^2$/hr). However, the incorporation of oleic acid and a combination of oleic acid and lecithin in the testosterone vitamin E-TPGS CIA systems (#51A and #52A) greatly reduced the testosterone diffusion ability; the diffusion flux value of these two systems was 149.6 μg/cm$^2$/hr and 105.6 μg/cm$^2$/hr respectively. The CIA with the second highest testosterone diffusion ability was the testosterone lauroyl polyoxyl-32 glycerides system (#50A) with a diffusion flux value is 395.8 μg/cm$^2$/hr. The testosterone polyethylene glycol system (#48A) exhibited diffusion ability or flux lower than that of the testosterone lauroyl polyoxyl-32 glycerides system (#50A) and the testosterone vitamin E-TPGS CIA system (#53A).

The rank of testosterone diffusion ability across the polysulfone membrane with 4% BSA in the receiver cell in various CIA systems is in order of its solubility in the corresponding aqueous CIA solutions. The testosterone solubility is the highest in the saturated vitamin E-TPGS, followed by the saturated lauroyl polyoxyl-32 glycerides and the saturated polyethylene glycol solution. The higher the testosterone solubility in the aqueous CIA solution, the higher the diffusion ability of the testosterone from the corresponding CIA system. The diffusion data suggest that the ability of CIA systems to solubilize and maintain a drug in solution in aqueous system can influence drug diffusion ability across the membrane.

TABLE 28

Testosterone Diffusion Across Polysulfone Membrane with 4% BSA, in Receiver Cell Medium
Average Amount Transmitted (ug)

| Time (min) | 48A | 49A | 50A | 51A | 52A | 53A |
|---|---|---|---|---|---|---|
| 10 | 19 | 152 | 67 | 16 | 15 | 76 |
| 20 | 72 | 462 | 169 | 40 | 40 | 361 |
| 30 | 137 | 746 | 345 | 72 | 74 | 703 |
| 45 | 209 | 1064 | 566 | 136 | 111 | 1030 |
| 60 | 307 | 1418 | 796 | 205 | 161 | 1318 |
| 90 | 438 | 1864 | 1054 | 350 | 261 | 1776 |
| 120 | 602 | 2443 | 1399 | 529 | 373 | 2350 |
| Flux (μg/cm$^2$/hr) | | | | | | |
| | 170.2 | 691.3 | 395.8 | 149.6 | 105.6 | 665.0 |

Figure 29:
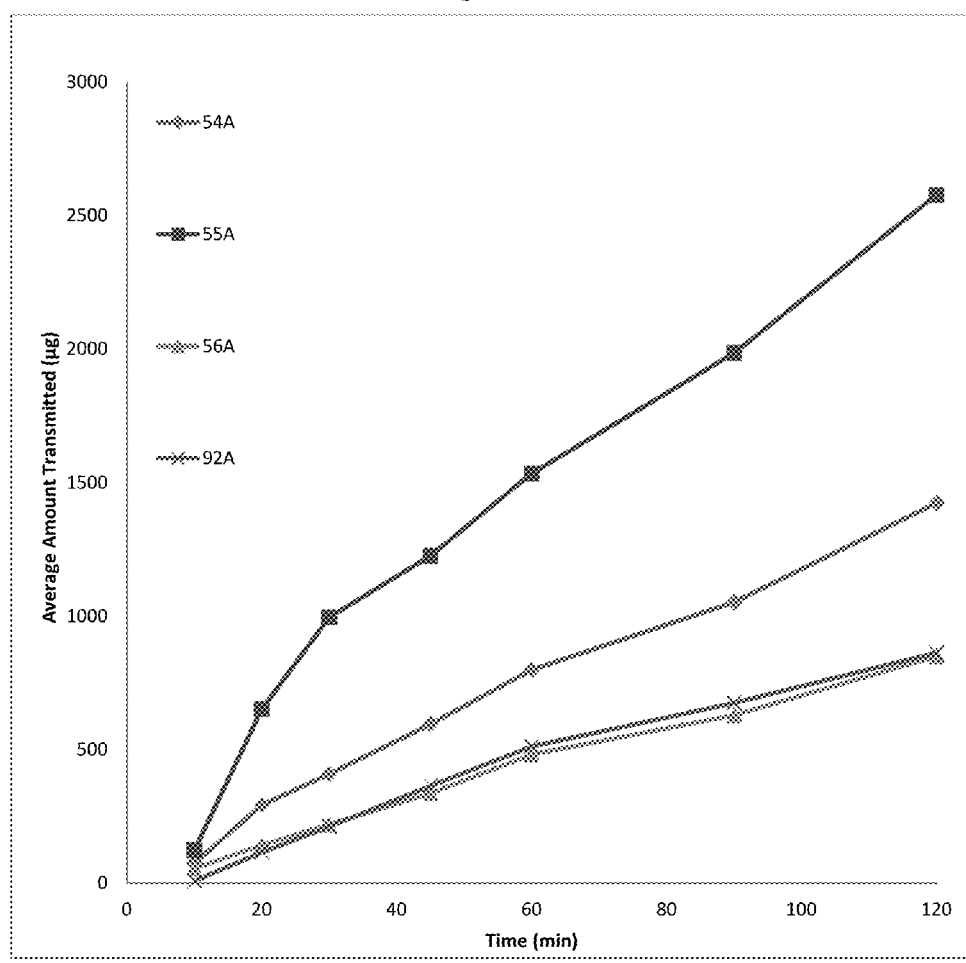
FIG. 29 depicts a graph corresponding to diffusion profiles of various testosterone CIA systems evaluated for testosterone diffusion across a 0.45 μm polysulfone membrane with 20% BSA receptor cell medium.
Figure 30:
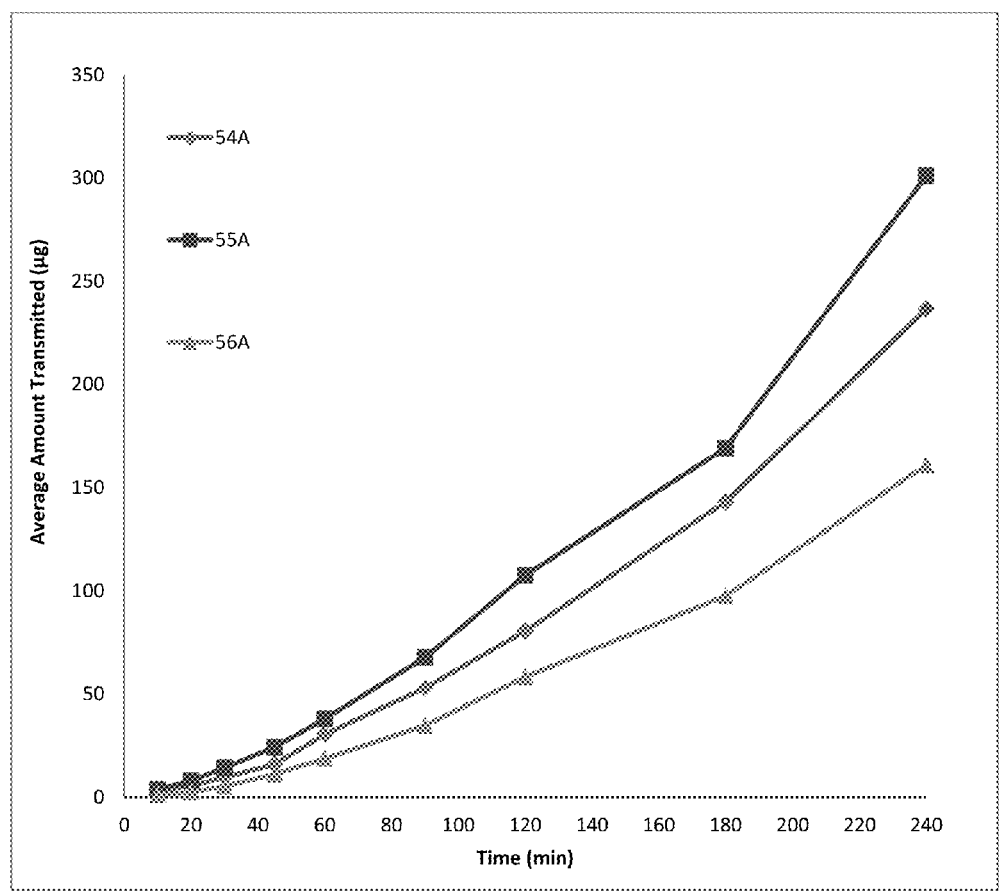
FIG. 30 depicts curves corresponding to diffusion profiles of various testosterone CIA systems evaluated for testosterone diffusion across cell cultured NHu-3D oral buccal epithelial mucosal tissue with 20% BSA receptor cell medium.
Figure 31:
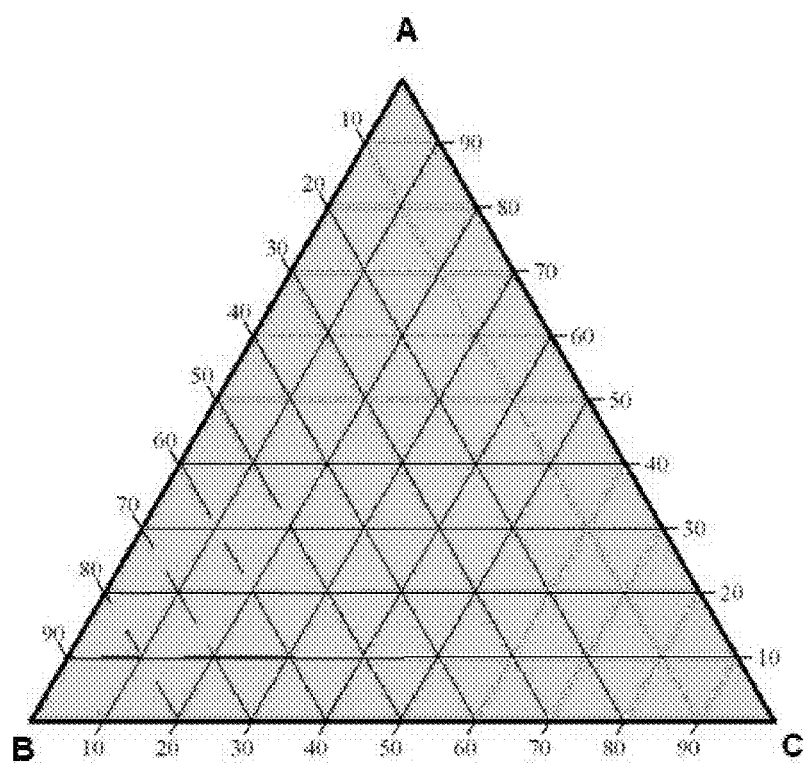
FIG. 31 depicts a ternary phase diagram for polyethylene glycol 8000, vitamin E-TPGS, and lauroyl polyoxyl-32 glycerides.
Figure 32:
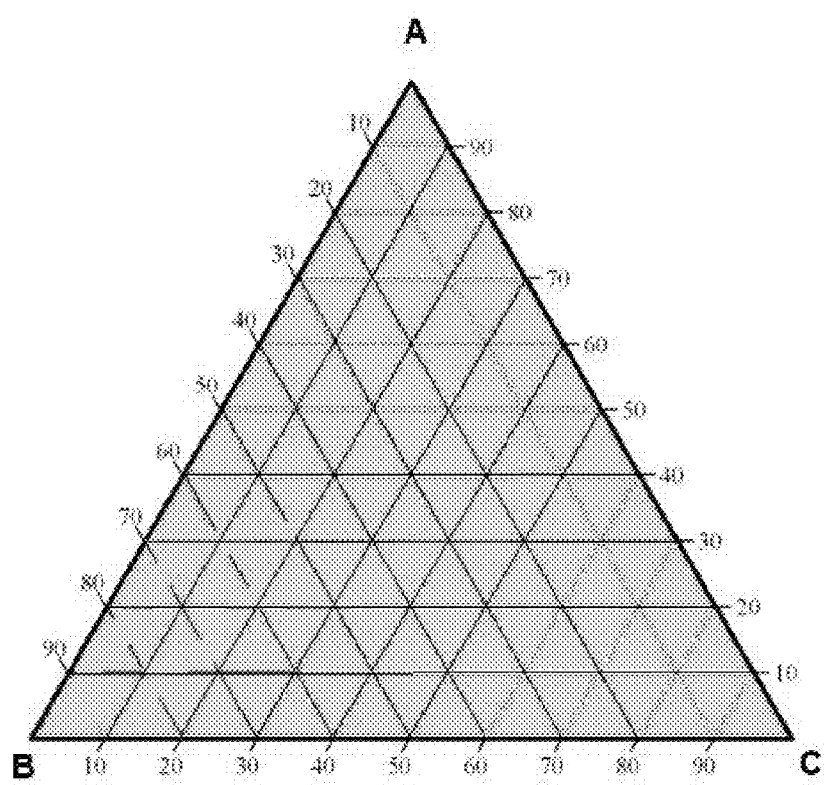
FIG. 32 depicts a ternary phase diagram for polyethylene glycol 8000, oleic acid and vitamin E-TPGS.
Figure 33:
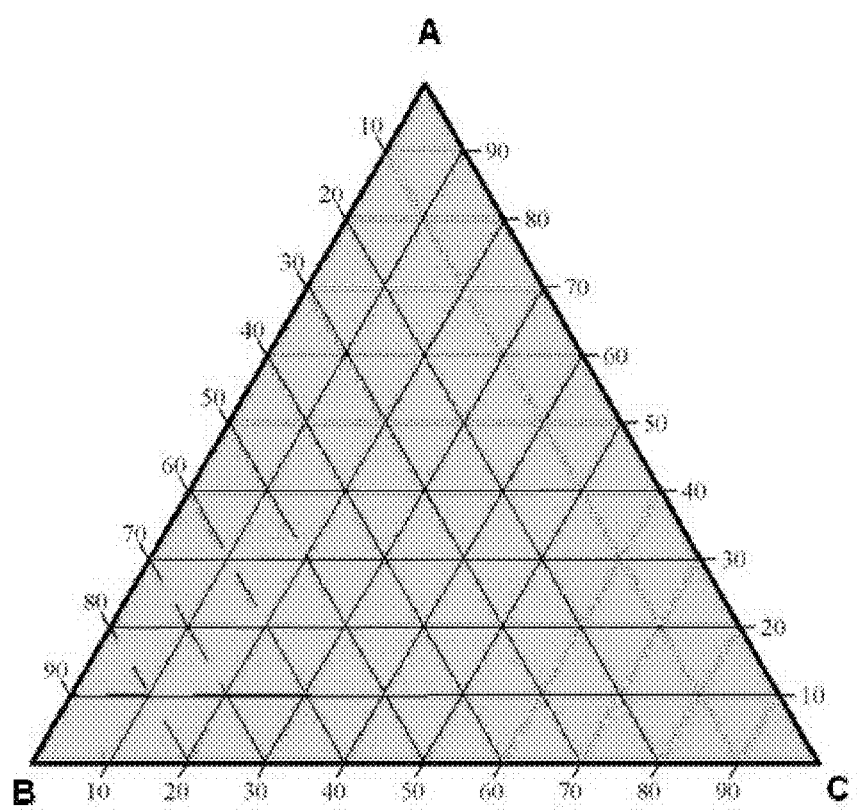
FIG. 33 depicts a ternary phase diagram for polyethylene glycol 8000, lauric acid, and vitamin E-TPGS.
Figure 34:
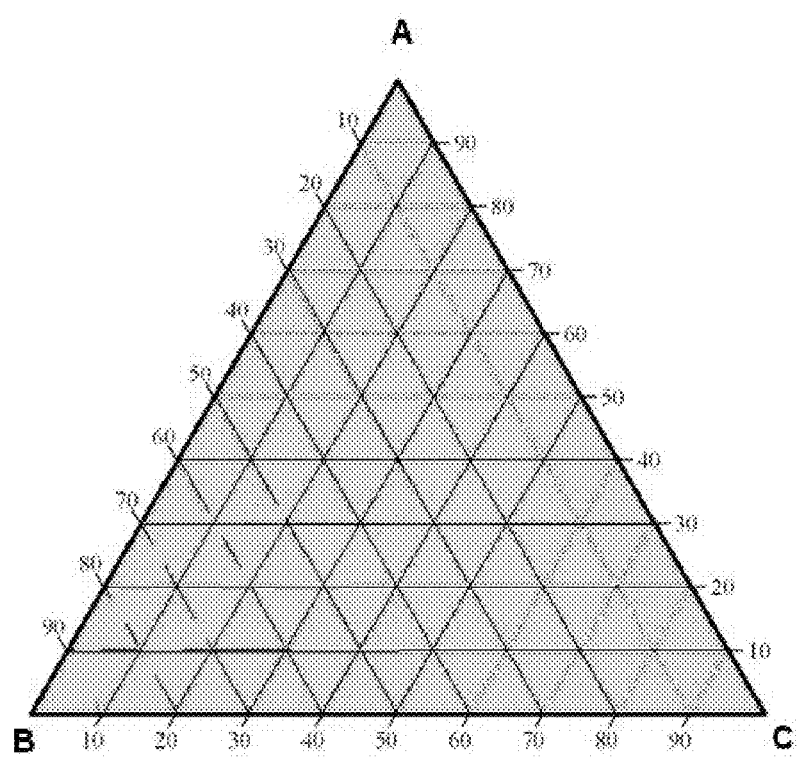
FIG. 34 depicts a ternary phase diagram for polyethylene glycol 8000, oleic acid, and lauroyl polyoxyl-32 glycerides.
Figure 35:
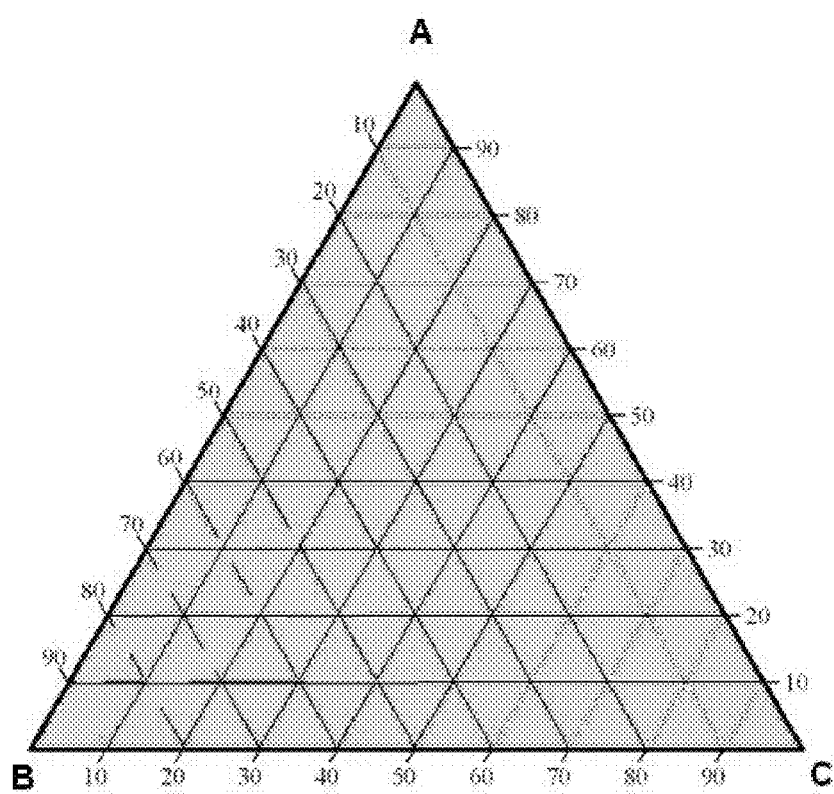
FIG. 35 depicts a ternary phase diagram for polyethylene glycol 8000, lauric acid, and lauroyl polyoxyl-32 glycerides.
Figure 36:
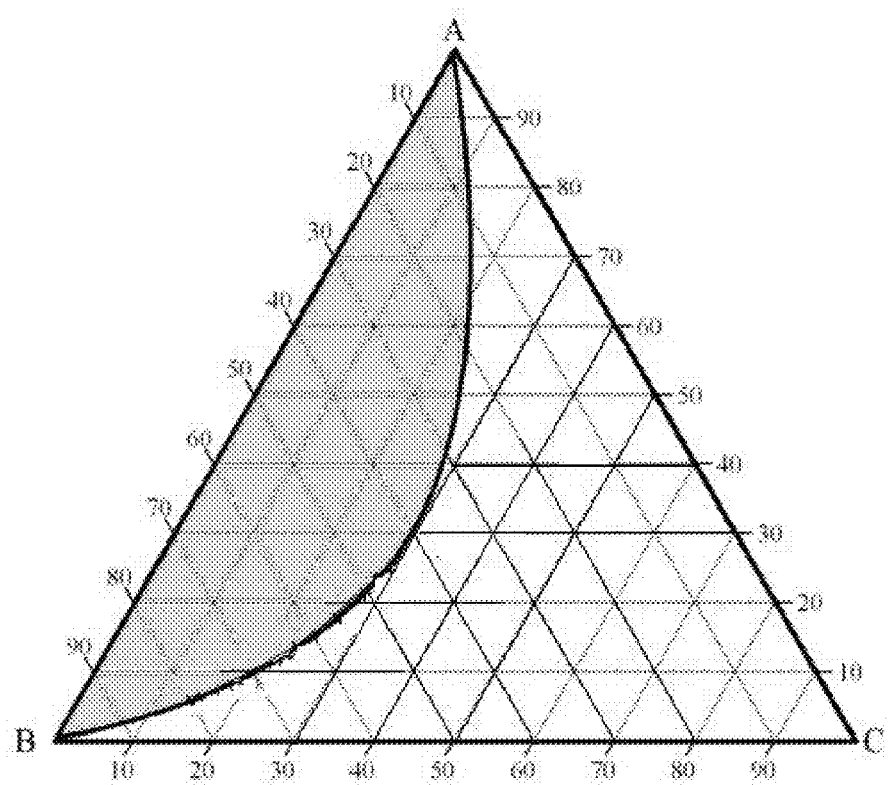
FIG. 36 depicts a ternary phase diagram for polyethylene glycol 8000, oleic acid, and lecithin.
Figure 37:
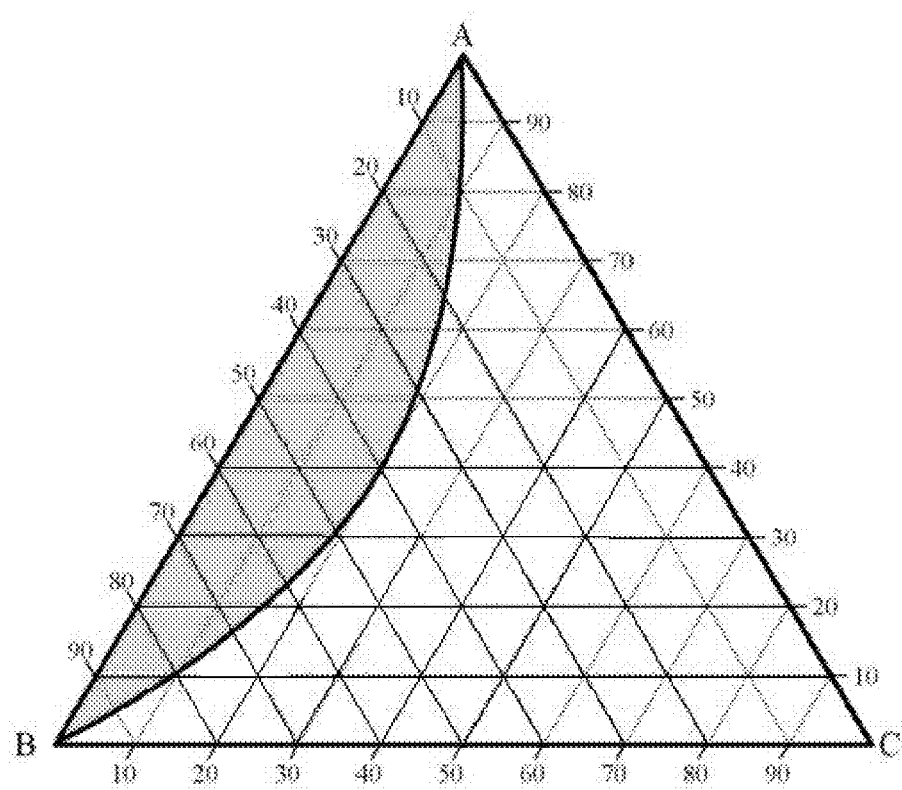
FIG. 37 depicts a ternary phase diagram for polyethylene glycol 8000, lauric acid, and lecithin.
Figure 38:
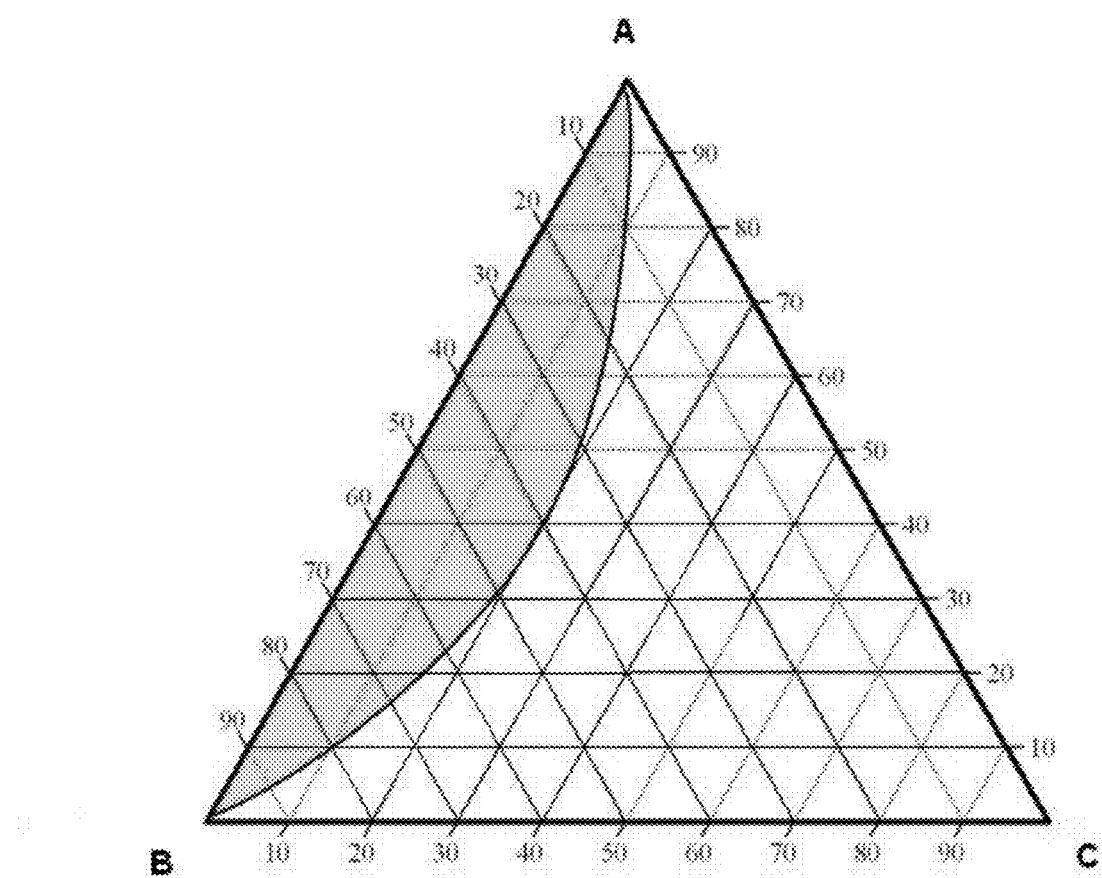
FIG. 38 depicts a ternary phase diagram for polyethylene glycol 8000, lauroyl polyoxyl-32 glycerides, and hydrogenated vegetable oil.
Figure 39:
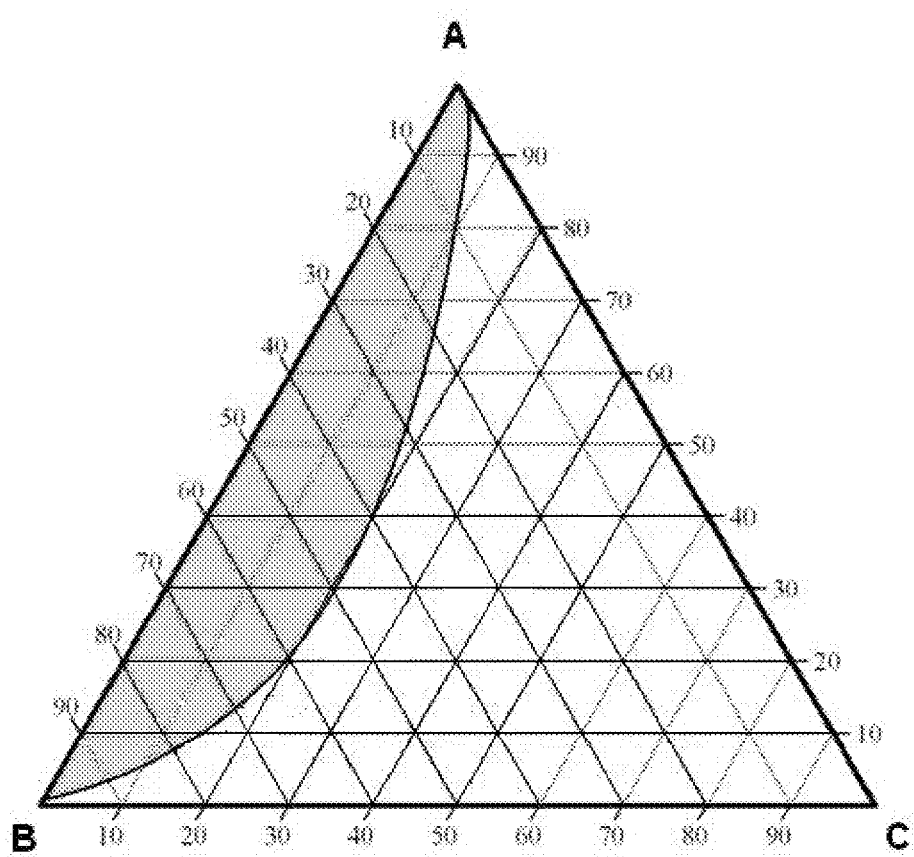
FIG. 39 depicts a ternary phase diagram for polyethylene glycol 8000, lauroyl polyoxyl-32 glycerides, and cocoa butter.
Figure 40:
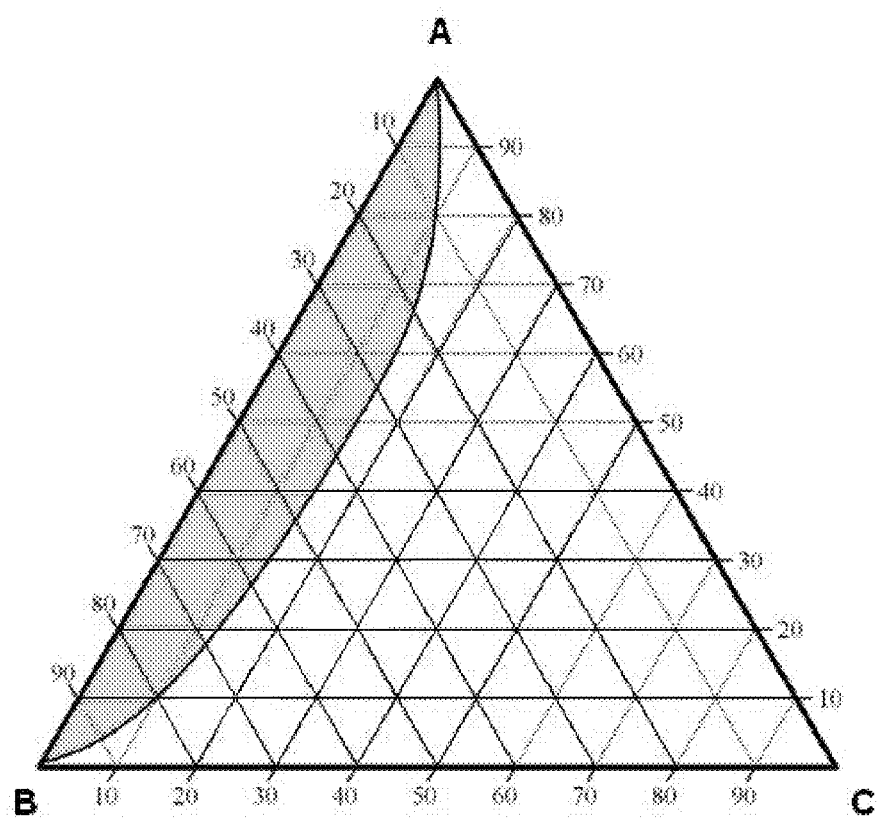
FIG. 40 depicts a ternary phase diagram for polyethylene glycol 8000, vitamin E-TPGS, and cocoa butter.
Figure 41:
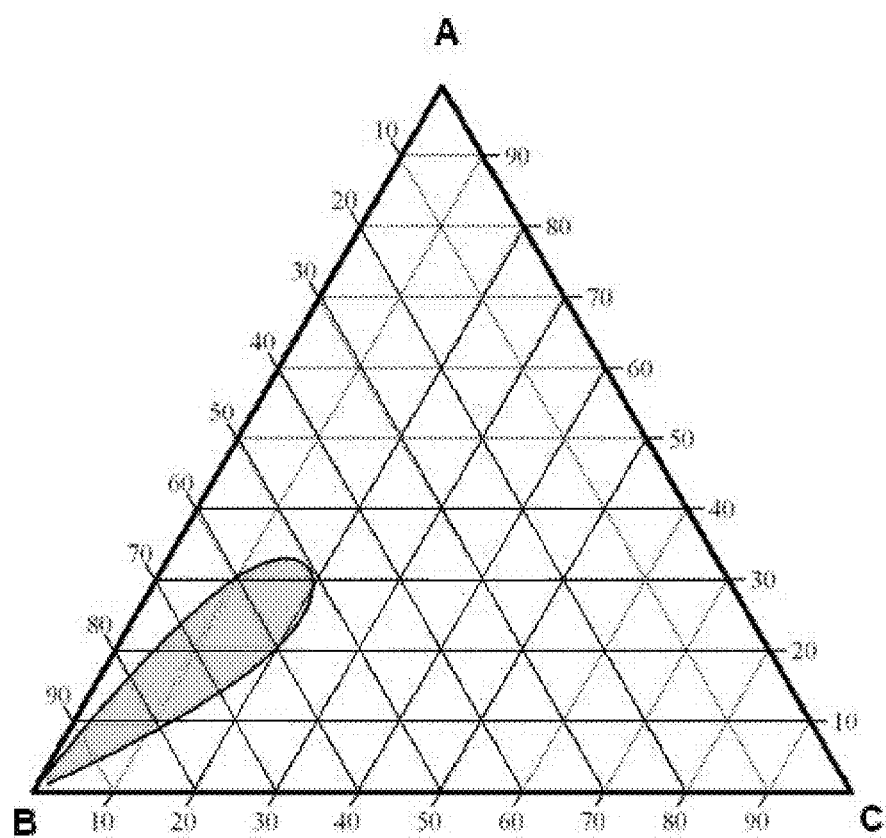
FIG. 41 depicts a ternary phase diagram for polyethylene glycol 8000, lauroyl polyoxyl-32 glycerides, and lauroyl macrogol-6 glycerides.
Figure 42:
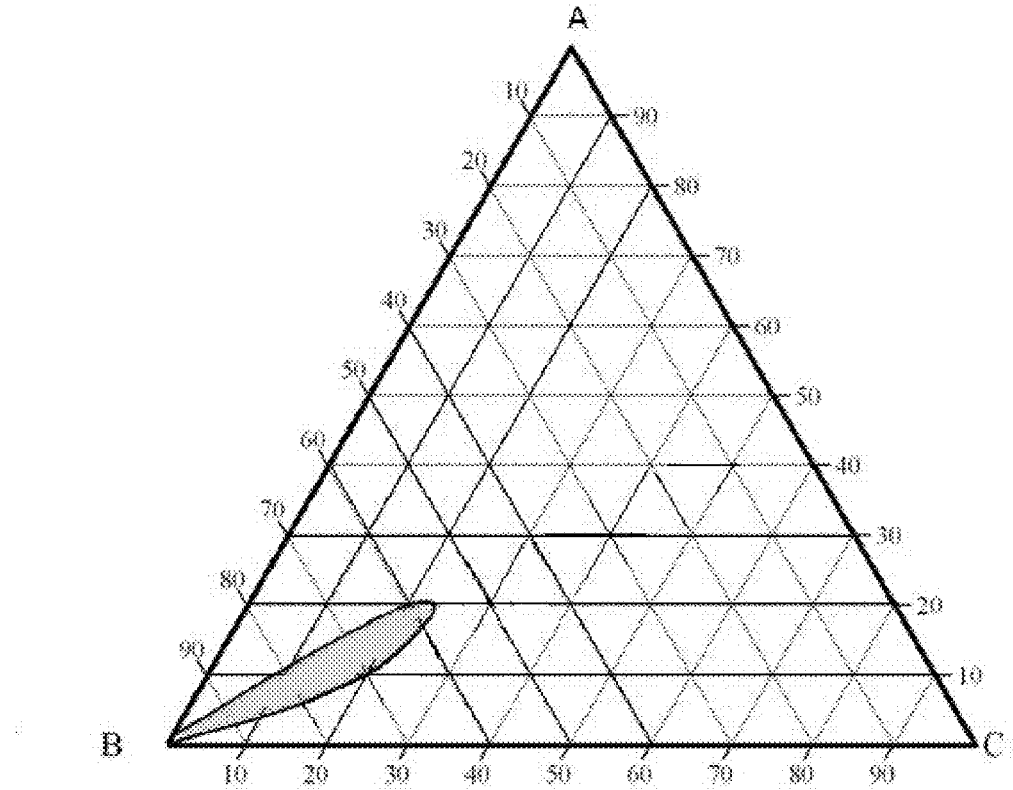
FIG. 42 depicts a ternary phase diagram for polyethylene glycol 8000, sucrose esters, and cocoa butter.
Figure 43:
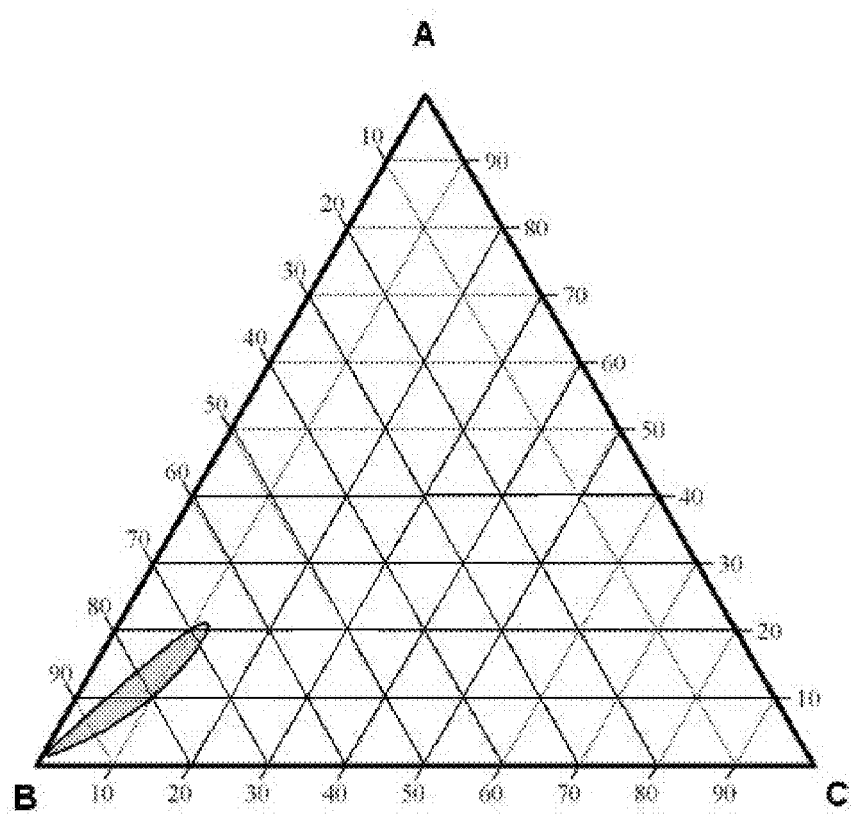
FIG. 43 depicts a ternary phase diagram for polyethylene glycol 8000, lauroyl macrogol-6 glycerides, and hydrogenated vegetable oil.

Discussion II:

The diffusion data and profiles of various testosterone CIA systems across the polysulfone membrane with 20% BSA in the receiver cell are given in Table 29, and the graph corresponding to these profiles are shown in FIG. 29. The testosterone/vitamin E-TPGS CIA system (#55A) showed the highest diffusion ability or flux (729 μg/cm$^2$/hr) among all the testosterone CIA systems, possibly due to the testosterone superior solubility in the aqueous solution of vitamin E-TPGS.

Interestingly, the diffusion ability or flux of the testosterone/vitamin E-TPGS CIA system (#55A) is about three times fold of that of a physical mixture of testosterone and vitamin E-TPGS (#92A). The diffusion flux of the physical mixture of testosterone and vitamin E-TPGS (#92A) is only about 244.1 μg/cm$^2$/hr. In theory, the testosterone solubility is the same in the aqueous solution of a fixed concentration of vitamin E-TPGS, regardless of the physical states of vitamin E-TPGS, i.e., being as a part of the melt dispersion/CIA system or being as part of the physical mixture. Hence, the significant increase in the diffusion flux for the testosterone/vitamin E-TPGS CIA system (#55A) is due to the difference in the physical states of testosterone. The molecular level of testosterone in solid state in vitamin E-TPGS molten CIA system (#55A) is essential to improve the diffusion ability as compared to the crystalline or the un-decrystallized state of testosterone in the physical mixture of testosterone and vitamin E-TPGS (#92A).

This indicates that the ability of a CIA, such as vitamin E-TPGS to decrystallize or dissolve a drug, such as testosterone, in molten state and maintain the drug in its molecular level in solid state is as crucial as its ability to help maintain the drug in its molecular level in aqueous solution, preventing precipitation. Hence both the abilities of an agent e.g. its decrystallization potential and its ability to maintain high concentration of poorly soluble drug in aqueous phase without precipitation are essential for improvement in diffusion across a permeable membrane thereby absorption and bioavailability.

Surprisingly, the permeation of testosterone is higher from the polyethylene glycol system than from the lauroyl polyoxyl-32 glycerides system despite the lower aqueous solubility contribution from the polyethylene glycol system. The testosterone diffusion flux across the polysulfone membrane was 729 µg/cm$^2$/hr from the vitamin E-TPGS system, 402.8 µg/cm$^2$/hr from the polyethylene glycol system and 240.6 µg/cm$^2$/hr from the lauroyl polyoxyl-32 glycerides system. Also it was surprisingly observed that polyethylene glycol diffusion ability with 20% BSA in the donor cell was higher than lauroyl polyoxyl-32 glycerides. Also noted that the lauroyl polyoxyl-32 glycerides system exhibited lower diffusion in 4% BSA than in 20% BSA in donor cell.

TABLE 29

Testosterone Diffusion Across Polysulfone with Membrane 20% BSA Receiver Cell Medium

| Time (min) | 54A | 55A | 56A | 92A |
|---|---|---|---|---|
| Average Amount Transmitted (µg) | | | | |
| 10 | 76 | 124 | 54 | 9 |
| 20 | 292 | 652 | 143 | 115 |
| 30 | 409 | 996 | 219 | 212 |
| 45 | 595 | 1226 | 337 | 364 |
| 60 | 798 | 1534 | 481 | 512 |
| 90 | 1052 | 1985 | 629 | 675 |
| 120 | 1423 | 2576 | 849 | 863 |
| Flux (µg/cm$^2$/hr) | | | | |
| | 402.8 | 729.0 | 240.6 | 244.1 |

Example 13

In Vitro Permeability Studies of Testosterone from Various CIA Systems across EpiOral Buccal Epithelial Mucosal Tissue NHu-3D The various testosterone CIA systems specified in Table 27 were evaluated to determine testosterone permeability across a 3-dimentional, highly differentiated human buccal epithelial cell cultured EpiOral tissue (MatTek Corporation) using Franz diffusion cell apparatus at 37° C. Donor cell medium was 2 mL SSF (pH 7.4). Receptor cell medium was 7 mL PBS solution with 20% BSA to diminish testosterone retention in the epithelial cells and to facilitate testosterone transportation from intracellular fluid into the receptor medium. A dose of 2 mg testosterone was loaded into the donor cell for each testosterone CIA system The diffusion data and profiles of various testosterone CIA systems across the cell cultured NHu-3D oral buccal epithelial mucosal tissue are given in Table 30, and values corresponding to this data are graphically represented in FIG. 30.

Discussion:

MatTek's EpiOral tissues consist of normal, human-derived epithelial cells. The tissues are cultured on specially prepared cell culture inserts using serum free medium. Morphologically, the tissue models closely parallel native buccal human tissues, thus providing a useful in vitro membrane system to assess drug permeability across human oral transmucosal membrane.

The testosterone vitamin E-TPGS CIA system (#55A) showed the highest permeation ability or flux (42.6 µg/cm$^2$/hr) among all the testosterone CIA systems, possibly due to the ability of the CIA vitamin E-TPGS to maintain testosterone in its decrystallized molecular form in solid state in the formulation melt dispersion of vitamin E-TPGS as well as the ability of the CIA vitamin E-TPGS to maintain high concentration of testosterone in its molecular form in aqueous solution state in the aqueous environment containing vitamin E-TPGS.

The order of diffusion for formulation containing various CIAs observed is vitamin E-TPGS>polyethylene glycol>lauroyl polyoxyl-32 glycerides. For drugs with a major in-vivo absorption mechanism of passive diffusion, such as testosterone, the greater diffusion can lead to a greater permeability or a higher bioavailability. The increased permeability of formulation with CIA system across the human EpiOral epithelial mucosal tissue, thus the testosterone CIA systems bear a great potential of improving testosterone bioavailability across the human transmucosal membrane.

Surprisingly, the permeation of testosterone was higher from the polyethylene glycol system than from the lauroyl polyoxyl-32 system despite its lower solubility in the aqueous solution of polyethylene glycol. Moreover, this data is in line with the diffusion data across the polysulfone membrane with 20% BSA in the receptor medium. Testosterone permeation flux across the oral buccal epithelial mucosal tissue was 42.6 µg/cm$^2$/hr from the vitamin E-TPGS system, 33.5 µg/cm$^2$/hr from the polyethylene glycol system and 22.8 µg/cm$^2$/hr from the lauroyl polyoxyl-32 glycerides system.

TABLE 30

Diffusion Data and Profile for Testosterone CIA Systems across NHu-3D Oral Buccal Epithelial Mucosal Tissue

| Time (min) | 54A | 55A | 56A |
|---|---|---|---|
| Average Amount Transmitted (µg) | | | |
| 10 | 3 | 4 | 1 |
| 20 | 6 | 8 | 3 |
| 30 | 10 | 14 | 5 |
| 45 | 16 | 24 | 11 |
| 60 | 30 | 38 | 19 |
| 90 | 53 | 68 | 35 |
| 120 | 81 | 108 | 58 |
| 180 | 143 | 169 | 98 |
| 240 | 237 | 301 | 161 |
| Flux (µg/cm$^2$/hr) | | | |
| | 33.5 | 42.6 | 22.8 |

The permeation across the human mucosal membrane due to CIA was in the order of vitamin E-TPGS>polyethylene glycol>lauroyl polyoxyl-32 glycerides. This data is in line with the diffusion across the polysulfone membrane with 20% BSA as the receptor medium. The diffusion across the polysulfone membrane with 20% BSA as the receptor medium due to CIA was also in the order of vitamin E-TPGS>polyethylene glycol>lauroyl polyoxyl-32 glycerides. Thus there is a correlation between the diffusion data through the polysulfone membrane with 20% BSA as the receptor medium and the permeability data through the human mucosal membrane with 20% BSA as the receptor medium.

As discovered, the diffusion flux through the polysulfone membrane of testosterone/vitamin E-TPGS CIA system is about three folds of that of a physical mixture of testosterone and vitamin E-TPGS. Thus it can be postulated that the permeation flux through the human mucosal membrane of the testosterone/vitamin E-TPGS CIA system is significantly higher than that of a physical mixture of testosterone and vitamin E-TPGS. In addition, it can be postulated that the permeation enhancement across the human mucosal membrane due to CIA is in the order of vitamin E-TPGS>polyethylene glycol>lauroyl polyoxyl-32 glycerides. This indicates that the testosterone in various CIA systems improves testosterone permeability across the human oral/buccal mucosa and the CIA systems can be utilized in the design of a transmucosal dosage form to obtain optimum permeation property and increased bioavailability.

Thus, the CIA containing dosage form of this invention offers an advantage over existing dosage forms in that the dosage form of the invention creates molecular dispersion of poorly soluble drugs during manufacturing of the dosage form, maintains the drug in its molecular form in the solid dosage form, facilitate the drug release and retain its molecular form in the physiological aqueous media and thus improves the drug permeability through mucosa membrane. Any improvement in mucosal permeation improves transmucosal absorption in vivo, drug bioavailability and, ultimately therapeutic effectiveness.

Example 14

Phase Diagrams

The ability of various mixtures of CIAs (a hydrophilic CIA, a lipophilic CIA and an amphiphilic CIA) to form monophasic systems was evaluated. Several different weight ratios of three different CIAs were prepared as follows. Samples of about 1 gram of a combination of the three different CIAs at a particular weight ratio was mixed, heated and allowed to melt at melting point temperature in a water bath. The temperature of the mixture was maintained at the melting point temperature for at least 15 minutes. Then the samples were cooled to room temperature by placing them in ice cold water bath for at least 1 hour. The samples were visually evaluated for any phase separation during the holding time at high temperature and after cooling and solidification at 37° C. and room temperature. A sample was classified as a monophasic if it formed a single phase system in the molten state at high temperatures and a solidified homogenous mass without any phase separation during cooling and at 37° C. and at room temperature. The results were used to prepare ternary phase diagrams, which are depicted in FIGS. 31-43.

Table 31, below, describes which mixtures of CIAs were used to create each phase diagram in these figures. The shaded area presented on each of FIGS. 23-35 represents the monophasic systems or samples.

TABLE 31

| FIG. No. | Apex and Component |
|---|---|
| 31 | A Polyethylene glycol 8000<br>B Vitamin E-TPGS<br>C Lauroyl polyoxyl-32 glycerides |
| 32 | A Polyethylene glycol 8000<br>B Oleic Acid<br>C Vitamin E-TPGS |
| 33 | A Polyethylene glycol 8000<br>B Lauric Acid<br>C Vitamin E-TPGS |
| 34 | A Polyethylene glycol 8000<br>B Oleic Acid<br>C Lauroyl polyoxyl-32 glycerides |
| 35 | A Polyethylene glycol 8000<br>B Lauric Acid<br>C Lauroyl polyoxyl-32 glycerides |
| 36 | A Polyethylene glycol 8000<br>B Oleic Acid<br>C Lecithin |
| 37 | A Polyethylene glycol 8000<br>B Lauric Acid<br>C Lecithin |
| 38 | A Polyethylene glycol 8000<br>B Lauroyl polyoxyl-32 glycerides<br>C Hydrogenated vegetable oil |
| 39 | A Polyethylene glycol 8000<br>B Lauroyl polyoxyl-32 glycerides<br>C Cocoa butter |
| 40 | A Polyethylene glycol 8000<br>B Vitamin E-TPGS<br>C Cocoa butter |
| 41 | A Polyethylene glycol 8000<br>B Lauroyl polyoxyl-32 glycerides<br>C Lauroyl macrogol-6 glycerides |
| 42 | A Polyethylene glycol 8000<br>B Sucrose esters<br>C Cocoa butter |
| 43 | A Polyethylene glycol 8000<br>B Lauroyl macrogol-6 glycerides<br>C Hydrogenated vegetable oil |

Discussion

The oral transmucosal dosage form of the invention can comprise a solid monophasic primary vehicle. A solid monophasic primary vehicle as used herein refers to a vehicle that forms a single phase system in at high temperature and a solidified homogenous mass without any phase separation during cooling and at 37° C. and room temperature. As the term is used herein, the monophasic primary vehicle in the dosage form may be a solid solution, a solid microemulsion or a solid emulsion.

In some embodiments, the solid monophasic primary vehicle is a single CIA system, comprising a hydrophilic CIA, a lipophilic CIA or an amphiphilic CIA. In some embodiments, the solid monophasic primary vehicle is a binary CIA system, comprising a hydrophilic CIA and an amphiphilic CIA, or a lipophilic CIA and an amphiphilic CIA, or a hydrophilic CIA and a lipophilic CIA. In some embodiments, the solid monophasic primary vehicle is a ternary CIA system, comprising a hydrophilic CIA, a lipophilic CIA and an amphiphilic CIA. In other embodiments, the solid monophasic system may contain more than three CIAs.

The relative amounts of three different CIAs can be represented in a ternary phase diagram according to the Gibbs' phase rule of one, two or three phases. These points combine to form regions with boundaries between them, which represent the "phase behavior" of the system at constant temperature and pressure.

In FIGS. 31-43, the compositions that fall within the shaded areas in the phase diagrams represent monophasic mixtures of the components specified as appropriate for apexes A, B and C of the phase diagram. Thus, for mixtures of three different CIAs, a ternary phase diagram can be used to guide the selection of CIAs when a monophasic primary vehicle is desired.

All of the various embodiments or options described herein can be combined in any and all variations. While the invention has been particularly shown and described with reference to some embodiments thereof, it will be understood by those skilled in the art that they have been presented by way of example only, and not limitation, and various changes in form and details can be made therein without departing from the spirit and scope of the invention. Thus, the breadth and scope of the present invention should not be limited by any of the above-described exemplary embodiments, but should be defined only in accordance with the following claims and their equivalents.

All documents cited herein, including journal articles or abstracts, published or corresponding U.S. or foreign patent applications, issued or foreign patents, or any other documents, are each entirely incorporated by reference herein, including all data, tables, figures, and text presented in the cited documents.

What is claimed is:

1. An oral transmucosal dosage form comprising
   (a) a primary vehicle comprising
      (i) a crystallization inhibition agent (CIA), selected from the group consisting of
         I. a hydrophilic CIA selected from the group consisting of one or more polyethylene glycols (PEG) having a molecular weight ≥2000 which is solid at room temperature, polyvinylpyrrolidone (PVP), vinylpyrrolidone-vinyl acetate co-polymers, polyvinyl caprolactum-polyvinyl acetate-polyethylene glycol graft co-polymers, synthetic copolymers of ethylene oxide and propylene oxide, hydroxyl propyl cellulose, hydroxyl propyl methyl cellulose, polyethylene oxide, disaccharides, trioses, tetroses, sugar, trisaccharides, tetrasaccharides, oligosaccharides, polysaccharides, maltodextrin, polyols, or mixtures thereof;
         II. a lipophilic CIA selected from the group consisting of oleic acid, a hydrogenated vegetable oil, cocoa butter, carnauba wax; beeswax; or mixtures thereof;
         III. an amphiphilic CIA selected from the group consisting of polyethylene glycol glycerides, vitamin E-TPGS (d-alpha tocopherol polyethylene glycol 1000 succinate), mono-, di-, and tri-esters of sucrose with fatty acids, lecithin or mixtures thereof;
         IV. or any combination of I-III; and
      (ii) an estrogen
      wherein the estrogen is combined with the CIA to form the primary vehicle, and
      wherein the CIA reduces the crystallinity of the estrogen by at least 50% as measured by DSC relative to essentially pure estrogen not combined with the CIA; and
   (b) a secondary vehicle comprising
      (i) a hydrophilic water soluble component, and
      (ii) a texturizing agent,
   wherein said oral transmucosal dosage form weighs about 250 mg to about 5000 mg, said oral transmucosal dosage form erodes in about 5 to about 60 minutes, but does not disintegrate, and said oral transmucosal dosage form is solid at 37° C.

2. An oral transmucosal dosage form of claim 1, wherein said oral transmucosal dosage form comprises the drug having at least a 95% reduction in crystalinity.

3. The method of claim 1, wherein the estrogen is selected from the group consisting of conjugated estrogents, 17 β-estradiol, estradiol acetate, and estradiol hemihydrates.

4. The dosage form of claim 1, wherein the primary vehicle comprises at least 2 CIAs.

5. The dosage form of claim 1, wherein the primary vehicle comprises at least 2 CIAs, wherein the CIAs are selected from the group consisting of:
   a hydrophilic crystallization inhibition agent;
   a lipophilic crystallization inhibition agent; and
   an amphiphilic crystallization inhibition agent.

6. The oral dosage form of claim 1, wherein the primary vehicle comprises a binary crystallization inhibition agent system, wherein the binary crystallization inhibition agent system is monophasic.

7. The oral dosage form of claim 1, wherein the primary vehicle comprises a ternary crystallization inhibition agent system, wherein the ternary crystallization inhibition agent system is monophasic.

8. The oral transmucosal dosage form of claim 1, wherein said primary vehicle is monophasic.

9. The oral transmucosal dosage form of claim 1, wherein said dosage form erodes at a rate of about 5 mg/min to about 500 mg/min.

10. The oral transmucosal dosage form of claim 1, wherein at least 40% of the estrogen is released from said dosage form within 5 minutes, as measured using the glass bead rotating bottle method with 150 ml SSF.

11. The oral transmucosal dosage form of claim 1, further comprising a progestin.

12. The oral transmucosal dosage form of claim 11, wherein the progestin is selected from the group consisting of progesterone, and norgestimate, and levonorgestrel.

13. The oral transmucosal dosage form of claim 1, wherein said estrogen is in free base form.

14. The transmucosal dosage form of claim 1, wherein the dosage form is packaged in a moisture and/or oxygen barrier polymer film blister package.

15. The oral transmucosal dosage form of claim 1, wherein the CIA is molten when combined with the estrogen.

16. The oral transmucosal dosage form of claim 1, wherein the CIA and the estrogen is solubilized in a solvent or mixture of solvents.

17. An oral transmucosal dosage form comprising
   (a) a primary vehicle comprising
      (i) a crystallization inhibition agent (CIA), selected from the group consisting of
         I. a hydrophilic CIA selected from the group consisting of one or more polyethylene glycols (PEG) having a molecular weight ≥2000 which is solid at room temperature, polyvinylpyrrolidone (PVP), vinylpyrrolidone-vinyl acetate co-polymers, polyvinyl caprolactum-polyvinyl acetate-polyethylene glycol graft co-polymers, synthetic copolymers of ethylene oxide and propylene oxide, hydroxyl propyl cellulose, hydroxyl propyl methyl cellulose, polyethylene oxide, disaccharides, trioses, tetroses, sugar, trisaccharides, tetrasaccharides, oligosaccharides, polysaccharides, maltodextrin, polyols, or mixtures thereof;

II. a lipophilic CIA selected from the group consisting of oleic acid, a hydrogenated vegetable oil, cocoa butter, carnauba wax; beeswax; or mixtures thereof;

III. an amphiphilic CIA selected from the group consisting of polyethylene glycol glycerides, vitamin E-TPGS (d-alpha tocopherol polyethylene glycol 1000 succinate), mono-, di-, and tri-esters of sucrose with fatty acids, lecithin or mixtures thereof;

IV. or any combination of I-III; and (ii) an estrogen wherein the estrogen is combined with the CIA to form the primary vehicle, and wherein the CIA reduces the crystallinity of the estrogen by at least 50% as measured by DSC relative to essentially pure estrogen not combined with the CIA; and (b) a secondary vehicle comprising
(i) a hydrophilic water soluble component, and
(ii) a texturizing agent, wherein the CIA reduces the crystallinity of the estrogen by at least a 50% reduction in crystallinity as measured by & DSC thermogram relative to a dosage form not comprising a CIA but otherwise substantially identical in composition.

18. A method of making an oral transmucosal dosage form comprising the steps of
i) providing a crystallization inhibition agent selected from the group consisting of
   I. a hydrophilic CIA selected from the group consisting of one or more polyethylene glycols (PEG) having a molecular weight ≥2000 which is solid at room temperature, polyvinylpyrrolidone (PVP), vinylpyrrolidone-vinyl acetate co-polymers, polyvinyl caprolactum-polyvinyl acetate-polyethylene glycol graft co-polymers, synthetic copolymers of ethylene oxide and propylene oxide, hydroxyl propyl cellulose, hydroxyl propyl methyl cellulose, polyethylene oxide, disaccharides, trioses, tetroses, sugar, trisaccharides, tetrasaccharides, oligosaccharides, polysaccharides, maltodextrin, polyols, or mixtures thereof;
   II. a lipophilic CIA selected from the group consisting of oleic acid, a hydrogenated vegetable oil, cocoa butter, carnauba wax, beeswax, or mixtures thereof;
   III. an amphiphilic CIA selected from the group consisting of polyethylene glycol glycerides, vitamin E-TPGS (d-alpha tocopherol polyethylene glycol 1000 succinate), mono-, di-, and tri-esters of sucrose with fatty acids, lecithin or mixtures thereof;
   IV. or any combination of I-III;
ii) applying heat to melt said crystallization inhibition agent, and mixing to create a molten mixture;
iii) adding an estrogen to said molten mixture, and mixing estrogen and said molten mixture;
iv) cooling said molten mixture and milling said molten mixture to form a powder primary vehicle;
v) adding a secondary vehicle to said powder primary vehicle and mixing; and
vi) compressing said secondary vehicle and powder primary vehicle into an oral transmucosal dosage form, wherein said transmucosal dosage form is about 250 mg to about 5000 mg, erodes in about 5 to about 60 minutes, but does not disintegrate, and is solid at 37° C., wherein the secondary vehicle comprises
(i) a hydrophilic water soluble component; and
(ii) a texturizing agent; and wherein the CIA reduces the crystallinity of the estrogen by at least 50% as measured by DSC relative to essentially pure estrogen not combined with the CIA.

19. A method of making an oral transmucosal dosage form comprising:
i) mixing an estrogen with one or more crystallization inhibition agent(s); selected from the group consisting of
   I. a hydrophilic CIA selected from the group consisting of one or more polyethylene glycols (PEG) having a molecular weight ≥2000 which is solid at room temperature, polyvinylpyrrolidone (PVP), vinylpyrrolidone-vinyl acetate co-polymers, polyvinyl caprolactum-polyvinyl acetate-polyethylene glycol graft co-polymers, synthetic copolymers of ethylene oxide and propylene oxide, hydroxyl propyl cellulose, hydroxyl propyl methyl cellulose, polyethylene oxide, disaccharides, trioses, tetroses, sugar, trisaccharides, tetrasaccharides, oligosaccharides, polysaccharides, maltodextrin, polyols, or mixtures thereof;
   II. a lipophilic CIA selected from the group consisting of oleic acid, a hydrogenated vegetable oil, cocoa butter, carnauba wax, beeswax, or mixtures thereof;
   III. an amphiphilic CIA selected from the group consisting of polyethylene glycol glycerides, vitamin E-TPGS (d-alpha tocopherol polyethylene glycol 1000 succinate), mono-, di-, and tri-esters of sucrose with fatty acids, lecithin or mixtures thereof;
   IV. or any combination of I-III;
(ii) solubilizing the mixture of (i) in a solvent or a mixture of solvents;
(iii) mixing the solution of (ii) with secondary vehicle;
(iv) evaporating the solvent(s), forming a combination of estrogen and crystallization inhibition agent(s) mixed uniformly with secondary vehicle, which will act as the primary blend;
(v) milling the primary blend to form a powder;
(vi) mixing the powder from the previous step with additional secondary vehicle; and
(vii) compressing said blend from step (vi) into an oral transmucosal dosage form;

wherein said transmucosal dosage from is about 250 mg to about 5000 mg, erodes in about 5 to 60 minutes, but does not disintegrate and is solid at 37° C.

wherein the secondary vehicle comprises
(i) a hydrophilic water soluble component, and
(ii) a texturizing agent, and wherein the CIA reduces the crystallinity of the estrogen by at least 50% as measured by DSC relative to essentially pure estrogen not combined with the CIA.

* * * * *